(12) United States Patent
Gudmundsson et al.

(10) Patent No.: US 7,199,120 B2
(45) Date of Patent: Apr. 3, 2007

(54) PYRAZOLO-PYRIDINE DERIVATIVES AS ANTIHERPES AGENTS

(75) Inventors: Kristjan Gudmundsson, Durham, NC (US); Brian A Johns, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 449 days.

(21) Appl. No.: 10/496,358

(22) PCT Filed: Nov. 20, 2002

(86) PCT No.: PCT/US02/37052

§ 371 (c)(1),
(2), (4) Date: May 20, 2004

(87) PCT Pub. No.: WO03/050120

PCT Pub. Date: Jun. 19, 2003

(65) Prior Publication Data

US 2004/0248903 A1   Dec. 9, 2004

Related U.S. Application Data

(60) Provisional application No. 60/339,585, filed on Dec. 11, 2001.

(51) Int. Cl.
C07D 471/04 (2006.01)
A61K 31/44 (2006.01)

(52) U.S. Cl. .................. 514/235.8; 514/275; 544/122; 544/295; 544/331

(58) Field of Classification Search ................ 544/122, 544/295, 331; 514/235.8, 275
See application file for complete search history.

(56) References Cited

U.S. PATENT DOCUMENTS

| | | |
|---|---|---|
| 4,576,952 A | 3/1986 | Hurst et al. |
| 4,621,089 A | 11/1986 | Ward et al. |
| 4,670,432 A | 6/1987 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |
| 6,207,675 B1 | 3/2001 | Carry et al. |
| 6,919,352 B2 | 7/2005 | Chamberlain et al. |
| 6,962,914 B2 | 11/2005 | Gudmundsson et al. |
| 7,030,134 B2 | 4/2006 | Gudmundsson et al. |
| 7,034,030 B2 | 4/2006 | Alberti et al. |
| 7,087,618 B2 | 8/2006 | Chamberlain et al. |
| 7,109,209 B2 | 9/2006 | Alberti et al. |

FOREIGN PATENT DOCUMENTS

| | | |
|---|---|---|
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| WO | EP 0 364 204 A1 | 10/1989 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96/34866 | 11/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |

(Continued)

OTHER PUBLICATIONS

Vane, J. et al. "Towards a Better Aspirin." Nature, vol. 367, Jan. 20, 1994, pp. 215-216.

(Continued)

*Primary Examiner*—Deepak Rao
(74) *Attorney, Agent, or Firm*—Lorie Ann Morgan

(57) ABSTRACT

The present invention provides compounds of formula (I):

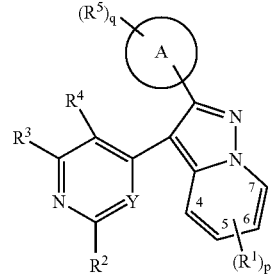

wherein all variables are as defined herein, pharmaceutical compositions containing the same, processes for preparing the same and their use as pharmaceutical agents.

27 Claims, No Drawings

FOREIGN PATENT DOCUMENTS

| | | |
|---|---|---|
| WO | WO 02 18382 | 3/2000 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02/16359 | 2/2002 |
| WO | WO 02/18382 | 3/2002 |
| WO | WO 02 48147 | 6/2002 |
| WO | WO 02/048148 | 6/2002 |
| WO | WO 02 066481 | 8/2002 |
| WO | WO 03/00682 | 1/2003 |

OTHER PUBLICATIONS

Carter, J. et al. "Recently Reported Inhibitors of Cyclooxygenase-2." Exp. Opin. Ther. Patents (1998), 8(1), pp. 21-29.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

PYRAZOLO-PYRIDINE DERIVATIVES AS ANTIHERPES AGENTS

CROSS REFERENCES TO RELATED APPLICATIONS

This application is a 371 Application of PCT/US02/37052, filed 20 Nov. 2002, which claims priority to U.S. Application Ser. No. 60/339,585, filed 11 Dec. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 50% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

VZV is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin's lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome and multiple sclerosis.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

U.S. Pat. No. 5,498,774 and European Patent No. 0 404 190 to Mitsudera et al., relates to condensed heterocyclic compounds of the general formula (I):

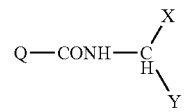

wherein Q is a condensed heterocyclic group having a nitrogen atom in the bridgehead which is unsubstituted or substituted, X is a hydrogen atom or a group attached through C, O, S or N, and Y is an electron attractive group; or its salt which is useful as an agricultural chemical.

BRIEF SUMMARY OF THE INVENTION

According to a first aspect of the invention there is provided a compound of formula (I):

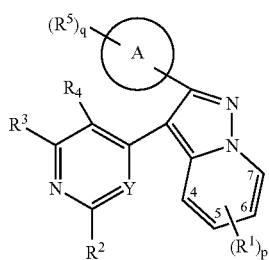

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Ay, —C(O)$NHR^{10}$Het, —C(S)$NR^9R^{11}$, —C(NH)$NR^7R^8$, —C(NH)$NR^7$Ay, —S(O)$_n R^9$, —S(O)$_n$Ay, —S(O)$_n$Het, —S(O)$_2 NR^7R^8$, —S(O)$_2 NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—C(O)$R^9$, —$R^{10}$O—C(O)Ay, —$R^{10}$O—C(O)Het, —$R^{10}$O—S(O)$_n R^9$, —$R^{10}OR^9$, —$R^{10}$C(O)$R^9$, —$R^{10}CO_2R^9$, —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}$NHC(NH)$NR^9R^{11}$, cyano, nitro and azido;

or two adjacent $R^1$ groups together with the carbon atoms to which they are bonded form a cycloalkyl or a 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, —C(O)$R^9$, —$CO_2R^9$, —C(O)$NR^9R^{11}$, —C(S)$NR^9R^{11}$, —C(NH)$NR^9R^{11}$, —$SO_2R^{10}$, —$SO_2NR^9R^{11}$, —$R^{10}$cycloalkyl, —$R^{10}OR^9$, —$R^{10}$C(O)$R^9$, —$R^{10}CO_2R^9$, —$R^{10}$C(O)$NR^9R^{11}$, —$R^{10}$C(S)$NR^9R^{11}$, —$R^{10}$C(NH)$NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}$NHC(NH)$NR^9R^{11}$;

each $R^9$ and $R^{11}$ are the same or different and are independently selected from the group consisting of H, alkyl, cycloalkyl, —$R^{10}$cycloalkyl, —$R^{10}$OH, —$R_{10}(OR^{10})_w$ wherein w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

Y is N or CH;

$R^2$ is selected from the group consisting of halo, alkyl, alkenyl, cycloalkyl, cycloalkenyl, Ay, Het, —$OR^7$—OAy, —OHet, —$OR^{10}$Het, —S(O)$_n R^9$, —S(O)$_n$Ay, —S(O)$_n$Het, —S(O)$_n NR^7R^8$, —$NR^7R^8$, —NHHet, —$NHR^{10}$Ay, —$NHR^{10}$Het, —$R^{10}NR^7R^8$ and —$R^{10}NR^7$Ay;

n is 0, 1 or 2;

$R^3$ and $R^4$ are the same or different and are each independently selected from the group consisting of H, halo, alkyl, alkenyl, cycloalkyl, Ay, Het, —$OR^7$, —OAy, —C(O)$R^7$, C(O)Ay, —$CO_2R^7$, —$CO_2$Ay, —$SO_2NHR^9$, —$NR^7R^8$, —$NR^7$Ay, —NHHet, —$NHR^{10}$Het, —$R^{10}$cycloalkyl, —$R^{10}OR^7$, —$R^{10}$OAy, —$R^{10}NR^7R^8$ and —$R^{10}NR^7$Ay;

Ring A is a 5–10 membered heterocyclic or heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Het, —C(S)$NR^9R^{11}$, —C(NH)$NR^7R^8$, —C(NH)$NR^7$Ay, —S(O)$_n R^9$, —S(O)$_2 NR^7R^8$, —S(O)$_2 NR^7$Ay, —$NR^7R^8$, —$NR^7$Ay, —NHHet, —$NHR^{10}$Ay, —$NHR^{10}$Het, —$R^{10}$ cycloalkyl, —$R^{10}$Het, —$R^{10}OR^9$, —$R^{10}$C(O)$R^9$, —$R^{10}CO_2R^9$, —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}$NHC(NH)$NR^9R^{11}$, cyano, nitro and azido;

wherein when Y is CH, $R^3$ is not —$NR^7$Ay;

or a pharmaceutically acceptable salt, solvate or physiologically functional derivative thereof.

According to a second aspect, the present invention provides a pharmaceutical composition comprising a compound of formula (I). The pharmaceutical composition may further comprise a pharmaceutically acceptable carrier or diluent. The pharmaceutical composition may further comprise an antiviral agent. In one embodiment, the pharmaceutical composition further comprises an antiviral agent selected from the group consisting of aciclovir and valaciclovir.

According to a third aspect, the present invention provides a method for the prophylaxis or treatment of a herpes viral infection in an animal. The method comprises administering to the animal a therapeutically effective amount of a compound of formula (I) or a pharmaceutically acceptable salt, solvate or physiologically functional derivative thereof. The herpes viral infection may be selected from the group consisting of herpes simplex virus 1, herpes simplex virus 2, cytomegalovirus, Epstein Barr Virus, herpes zoster virus, human herpes virus 6, human herpes virus 7 and human herpes virus 8.

According to a fourth aspect, the present invention provides a method for the prophylaxis or treatment of a condition or disease associated with a herpes viral infection in an animal, comprising administering to the animal a therapeutically effective amount of a compound of formula (I) or a pharmaceutically acceptable salt, solvate or physiologically functional derivative thereof.

According to a fifth aspect, the present invention provides a process for preparing a compound of formula (I) wherein Y is N and $R^3$ and $R^4$ are H. The process comprises reacting a compound of formula (IX):

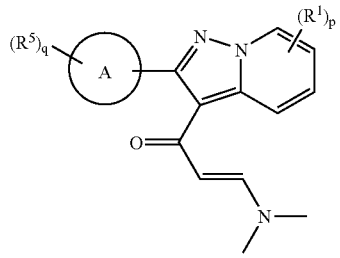

with a compound of formula (X):

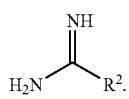

According to a sixth aspect, the present invention provides a process for preparing a compound of formula (I) wherein Y is N; $R^3$ is selected from the group consisting of of H, alkyl, cycloalkyl, alkenyl, Ay, Het, $-OR^7$, $-OAy$, $-C(O)R^7$, $C(O)Ay$, $-CO_2R^7$, $-CO_2Ay$, $-SO_2NHR^9$, $-NR^7R^8$ (where $R^7$ and $R^7$ are not H), $-NR^7Ay$ (where $R^7$ is not H), $-R^{10}$cycloalkyl, $-R^{10}OR^7$, $-R^{10}OAy$, $-R^{10}NR^7R^8$ and $-R^{10}NR^7Ay$; and $R^4$ is H. The process comprises reacting a compound of formula (XVI):

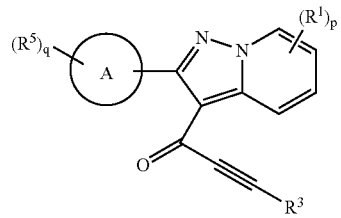

with a compound of formula (X):

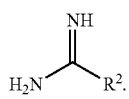

According to a seventh aspect, the present invention provides a process for preparing a compound of formula (I) wherein Y is N. The process comprises reacting a compound of formula (XX):

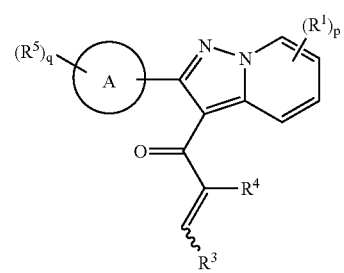

with a compound of formula (X):

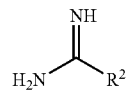

followed by oxidative aromatization.

According to an eighth aspect, the present invention provides a process for preparing a compound of formula (I). The process comprises reacting a compound of formula (XXII):

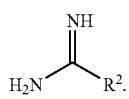

wherein $X^1$ is chloro, bromo or iodo;

with a compound of formula (XXIV):

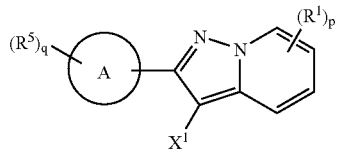

wherein $M^2$ is $-B(OH)_2$, $-B(Ra)_2$, $-B(Ra)_2$, $-Sn(Ra)_3$, Zn-halide, ZnRa, or Mg-halide halide where Ra is alkyl or cycloalkyl and halide is halo.

According to a ninth aspect, the present invention provides a process for preparing a compound according of formula (I). The process comprises reacting a compound of formula (XXIX):

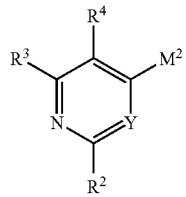

with a 1-aminopyridinium salt of formula (XXX):

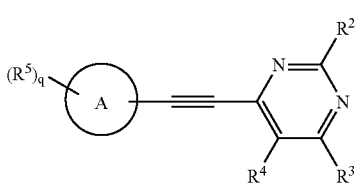

wherein Z- is a counter ion.

According to a tenth aspect, the present invention provides a process for preparing a compound of formula (I). The process comprises reacting a compound of formula (XXXVI):

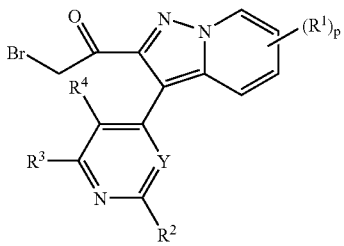

XXXVI with a suitable ring forming reagent.

In another aspect, the present invention provides a radiolabeled compound of formula (I) or a salt, solvate or physiologically functional derivative thereof. In one embodiment, the present invention provides a tritiated compound of formula (I) or a pharmaceutically acceptable salt, solvate or physiologically functional derivative thereof.

In another aspect, the present invention provides a compound of formula (I) for use in therapy.

In yet another aspect, the present invention provides a compound of formula (I) for use in the prophylaxis or treatment of a herpes viral infection.

In another aspect, the present invention provides a pharmaceutical composition for use in the prophylaxis or treatment of a herpes viral infection in an animal, such as a human, comprising a compound of formula (I).

In yet another aspect, the present invention provides a compound of formula (I) for use in the prophylaxis or treatment of a condition or disease associated with a herpes viral infection in an animal, such as a human.

In yet another aspect, the present invention provides a pharmacuetical composition for use in the prophylaxis or treatment of a condition or disease associated with a herpes viral infection in an animal, comprising a compound of formula (I).

In yet another aspect, the present invention provides the use of a compound of formula (I) for the preparation of a medicament for the prophylaxis or treatment of a herpes viral infection in an animal, such as a human.

In yet another aspect, the present invention provides the use of a compound of formula (I) for the preparation of a medicament for the prophylaxis or treatment of a condition or disease associated with a herpes viral infection in an animal, such as a human.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as compounds of formula (IX), (XVI), (XX), (XXII), (XXIX) and (XXXVI), the phrase "a compound of formula (number)" means a compound having that formula or a pharmaceutically acceptable salt, solvate or physiologically functional derivative thereof.

As used herein, the terms "alkyl" and "alkylene" refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" and "alkylene" also include substituted alkyl and substituted alkylene. The alkyl or alkylene groups may be optionally substituted with one or more substituents selected from the group consisting of mercapto, nitro, cyano, and halo. Perhaloalkyl, such as trifluoromethyl is one particular alkyl group.

As used herein, the term "cycloalkyl" refers to a non-aromatic carbocyclic ring having from 3 to 8 carbon atoms (unless otherwise specified) and no carbon—carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may be optionally substituted on any available carbon with one or more substituents selected from the group consisting of mercapto, nitro, cyano, halo, and alkyl.

As used herein, the term "alkenyl" refers to straight or branched hydrocarbon chains containing from 2 to 8 carbon atoms and at least one and up to three carbon—carbon double bonds. Examples of "alkenyl" as used herein include, but are not limited to ethenyl and propenyl. "Alkenyl" also includes substituted alkenyl. The alkenyl groups may be optionally substituted one any available carbon with one or more substituents selected from the group consisting of mercapto, nitro, cyano, halo, and alkyl.

As used herein, the term "cycloalkenyl" refers to a non-aromatic carbocyclic ring having from 3 to 8 carbon atoms (unless otherwise specified) and up to 3 carbon—carbon double bonds. "Cycloalkenyl" includes by way of example cyclobutenyl, cyclopentenyl and cyclohexenyl. "Cycloalkenyl" also includes substituted cycloalkenyl. The cycloalkenyl may be optionally substituted on any available carbon with one or more substituents selected from the group consisting of mercapto, nitro, cyano, halo, and alkyl.

As used herein, the term "alkynyl" refers to straight or branched hydrocarbon chains containing from 2 to 8 carbon atoms and at least one and up to three carbon—carbon triple bonds. Examples of "alkynyl" as used herein include, but are not limited to ethynyl and propynyl. "Alkynyl" also includes substituted alkynyl. The alkynyl groups may be optionally substituted on any available carbon with one or more substituents selected from the group consisting of mercapto, nitro, cyano, and halo.

The term "halo" or "halogen" refers to fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substituted aryl. Aryl rings may be optionally substituted with substituents selected from the group consisting of halo, alkyl (including perhaloalkyl, e.g., perfluoroalkyl), alkenyl, cycloalkyl, cycloalkenyl, alkoxy, amino, hydroxy, alkylhydroxy, alkylamine, carboxy, carboxamide, sulfonamide, Het, amidine, cyano, nitro and azido. Preferred aryl groups according to the invention include but are not limited to phenyl and substituted phenyl.

The term "heterocyclic" or "heterocycle" refers to monocyclic saturated or unsaturated non-aromatic groups and fused bicyclic non-aromatic groups, having the specified number of members (e.g. carbon and heteroatoms N and/or O and/or S) and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic group may be optionally substituted with substituents selected from the group consisting of halo, alkyl (including perhaloalkyl, e.g., perfluoroalkyl), alkenyl, cycloalkyl, cycloalkenyl, perfluoroalkyl, alkoxy, amino, hydroxy, alkylhydroxy, alkylamine, carboxy, carboxamide, sulfonamide, Het, amidine, cyano, nitro and azido. Preferred heterocyclic groups according to the invention include but are not limited to substituted and unsubstituted tetrahydrofuran, pyrrolidine, piperidine, morpholine, thiomorpholine and piperazine, and substituted variants thereof.

The term "heteroaryl" refers to aromatic monocyclic groups and aromatic fused bicyclic groups having the specified number of members (e.g. carbon and heteroatoms N and/or O and/or S) and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl group may be optionally substituted with substituents selected from the group consisting of halo, alkyl (including perhaloalkyl, e.g., perfluoroalkyl), alkenyl, cycloalkyl, cycloalkenyl, perfluoroalkyl, alkoxy, amino, hydroxy, alkylhydroxy, alkylamine, carboxy, carboxamide, sulfonamide, Het, amidine, cyano, nitro and azido. Preferred heteroaryl groups according to the invention include but are not limited to substituted and unsubstituted pyridine, furan, thiophene, pyrrole, imidazole, pyrazole, oxazole, thiazole and pyrimidine, and substituted variants thereof.

The term "members" (and variants thereof e.g., "membered") in the context of heterocyclic and heteoraryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

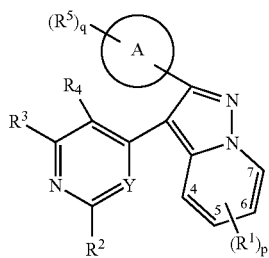

I wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —$C(O)R^9$, —$C(O)$Ay, —$C(O)$Het, —$CO_2R^9$, —$C(O)NR^7R^8$, —$C(O)NR^7$Ay, —$C(O)NHR^{10}$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—$C(O)R^9$, —$R^{10}$O—$C(O)$Ay, —$R^{10}$O—$C(O)$Het, —$R^{10}$O—$S(O)_nR^9$, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido;
or two adjacent $R^1$ groups together with the carbon atoms to which they are bonded form a cycloalkyl or a 5- or 6-membered heterocyclic group containing 1 or 2 heteroatoms;
each $R^7$ and $R^8$ are the same or different and are independently selected from the group consisting of H, alkyl, alkenyl, cycloalkyl, cycloalkenyl, —$C(O)R^9$, —$CO_2R^9$, —$C(O)NR^9R^{11}$, —$C(S)NR^9R^{11}$, —$C(NH)NR^9R^{11}$, —$SO_2R^{11}$, —$SO_2NR^9R^{11}$, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$;
each $R^9$ and $R^{11}$ are the same or different and are independently selected from the group consisting of H, alkyl, cycloalkyl, —$R^{10}$cycloalkyl, —$R^{10}$OH, —$R_{10}(OR^{10})_w$ wherein w is 1–10, and —$R^{10}NR^{10}R^{10}$;
each $R^{10}$ is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
Y is N or CH;
$R^2$ is selected from the group consisting of halo, alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)_nNR^7R^8$, —$NR^7R^8$, —NHHet, —$NHR^{10}$Ay, —$NHR^{10}$Het, —$R^{10}NR^7R^8$ and —$R^{10}NR^7$Ay;
n is 0, 1 or 2;
$R^3$ and $R^4$ are the same or different and are each independently selected from the group consisting of H, halo, alkyl, alkenyl, cycloalkyl, Ay, Het, —$OR^7$, —OAy, —$C(O)R^7$, $C(O)$Ay, —$CO_2R^7$, —$CO_2$Ay, —$SO_2NHR^9$, —$NR^7R^8$, —$NR^7$Ay, —NHHet, —$NHR^{10}$Het, —$R^{10}$cycloalkyl, —$R^{10}OR^7$, —$R^{10}$OAy, —$R^{10}NR^7R^8$ and —$R^{10}NR^7$Ay;
Ring A is a 5–10 membered heterocyclic or heteroaryl group;
q is 0, 1, 2, 3, 4 or 5; and
each $R^5$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —$C(O)R^9$, —$C(O)$Ay, —$C(O)$Het, —$CO_2R^9$, —$C(O)NR^7R^9$, —$C(O)NR^7$Ay, —$C(O)NHR^{10}$Het, —$C(S)NR^9R^{11}$, —$C(NH)NR^7R^8$, —C(NH)NR$^7$Ay, —S(O)$_n$R$^9$ —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Het, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido;

wherein when Y is CH, R$^3$ is not —NR$^7$Ay;

or a pharmaceutically acceptable salt, solvate or physiologically functional derivative thereof.

In one embodiment, the compounds of formula (I) are defined wherein p is 0, 1 or 2. More particularly, p is 1 or 2. In one embodiment of the present invention, the compounds of formula (I) are defined wherein p is 1. In one embodiment of the present invention, the compounds of formula (I) are defined wherein p is 2.

R$^1$ may be located at any of the C-4, C-5, C-6 and/or C-7 positions on the pyrazolopyridine ring.

In one embodiment of the invention wherein p is 1 or more, at least one R$^1$ contains an aryl, heterocyclic or heteroaryl moiety (e.g., at least one R$^1$ is selected from the group consisting of Ay, Het, —OAy, —OR$^{10}$Ay, —OHet, —OR$^{10}$Het, —C(O)Ay, —C(O)Het, —C(O)NR$^7$Ay, —C(O)NHR$^{10}$Ay, —C(O)NHR$^{10}$Het, —C(NH)NR$^7$Ay, —S(O)Ay, —S(O)$_n$Het, —S(O)$_2$NR$^7$Ay, —NR$^7$Ay, —NHHet, —NHR$^{10}$Ay, —NHR$^{10}$Het, —R$^{10}$Ay, —R$^{10}$Het, —R$^{10}$O—C(O)Ay, —R$^{10}$O—C(O)Het, —R$^{10}$C(O)NR$^7$Ay, —R$^{10}$C(O)NHR$^{10}$Het and —R$^{10}$NR$^7$Ay, or any subset thereof). In another embodiment, compounds of formula (I) are defined wherein at least one R$^1$ contains a heterocyclic or heteroaryl moiety (e.g., at least one R$^1$ is selected from the group consisting of Het, —OHet, —OR$^{10}$Het, —C(O)Het, —C(O)NHR$^{10}$Het, —S(O)$_n$Het, —NHHet, —NHR$^{10}$Het, —R$^{10}$Het, —R$^{10}$O—C(O)Het and —R$^{10}$C(O)NHR$^{10}$Het, or any subset thereof. In yet another embodiment, the compounds of formula (I) are defined wherein no R$^1$ contains an aryl, heterocyclic or heteroaryl moiety (e.g., each R$^1$ is the same or different and is independently selected from the group consisting of halo, alkyl, alkenyl, alkynyl, cycloalkyl, cycloalkenyl, —OR$^7$, —C(O)R$^9$, —CO$_2$R$^9$, —C(O)NR$^7$R$^8$, —C(S)NR$^9$R$^{11}$, —C(NH)NR$^7$R$^8$, —S(O)$_n$R$^9$, —S(O)$_2$NR$^7$R$^8$, —NR$^7$R$^8$, —R$^{10}$cycloalkyl, —R$^{10}$O—C(O)R$^9$, —R$^{10}$O—S(O)$_n$R$^9$, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NHC(NH)NR$^9$R$^{11}$, cyano, nitro and azido; or any subset thereof). In another embodiment, no R$^1$ contains a heteroaryl or heterocyclic moiety but may contain an aryl moiety (e.g., each R$^1$ is the same or different and is independently selected from the group consisting of halo, alkyl, alkenyl, alkynyl, cycloalkyl, cycloalkenyl, Ay, —OR$^7$, —OAy, —OR$^{10}$Ay, —C(O)R$^9$, —C(O)Ay, —CO$_2$R$^9$, —C(O)NR$^7$R$^8$, —C(O)NR$^7$Ay, —C(O)NHR$^{10}$Ay, —C(S)NR$^9$R$^{11}$, —C(NH)NR$^7$R$^8$, —C(NH)NR$^7$Ay, —S(O)$_n$R$^9$, —S(O)$_n$Ay, —S(O)$_2$NR$^7$R$^8$, —S(O)$_2$NR$^7$Ay, —NR$^7$R$^8$, —NR$^7$Ay, —NHR$^{10}$Ay, —R$^{10}$cycloalkyl, —R$^{10}$Ay, —R$^{10}$O—C(O)R$^9$, —R$^{10}$O—C(O)Ay, —R$^{10}$O—S(O)$_n$R$^9$, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido, or any subset thereof.)

One class of compounds of formula (I) includes those compounds defined wherein two adjacent R$^1$ groups together with the carbon atoms to which they are bonded form a cycloalkyl or a 5- or 6-membered heterocyclic group containing 1 or 2 heteroatoms. By "two adjacent R$^1$ groups" is meant that two R$^1$ groups are bonded to adjacent carbon atoms. When two adjacent R$^1$ groups together with the carbon atoms to which they are bonded form a cycloalkyl or a 5- or 6-membered heterocyclic group having 1 or 2 heteroatoms, each R$^1$ group may be the same or different and is selected from the group consisting of alkyl, —OR$^7$, —NR$^7$R$^8$, and —S(O)$_n$R$^9$. For example, in one embodiment two adjacent R$^1$ groups are —OR$^7$ and together with the carbon atoms to which they are bonded, they form a heterocyclic group such as:

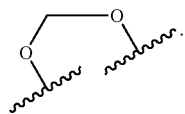

In another embodiment, two adjacent R$^1$ groups are alkyl and together with the carbon atoms to which they are bonded, they form a cycloalkyl group such as:

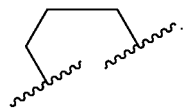

In another embodiment two adjacent R$^1$ groups are defined as —OR$^7$ and —NR$^7$R$^8$ respectively and together with the carbon atoms to which they are bonded, they form a heterocyclic group such as:

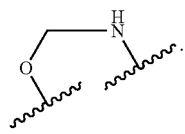

In another embodiment two adjacent R$^1$ groups are defined as —S(O)$_n$R$^9$ and —NR$^7$R$^8$ respectively and together with the carbon atoms to which they are bonded, they form a heterocyclic group such as:

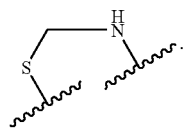

From these examples, additional embodiments can be readily ascertained by those skilled in the art In one particular embodiment, two adjacent R$^1$ groups together with the carbon atoms to which they are bonded do not form a cycloalkyl or a 5- or 6-membered heterocyclic group containing 1 or 2 heteroatoms.

In one embodiment, each R$^1$ is the same or different and is independently selected from the group consisting of halo, alkyl, Ay, Het, —OR$^7$, —OAy, —C(O)Het, —CO$_2$R$^9$, —C(O)NR$^7$R$^8$, —C(O)NR$^7$Ay, —C(O)NHR$^{10}$Het, —S(O)$_n$R$^9$, —NR$^7$R$^8$, —NR$^7$Ay, —NHHet, —NHR$^{10}$Ay, —NHR¹⁰Het, —R¹⁰OR⁹, cyano, nitro and azido, or any subset thereof. More particularly, each $R^1$ is the same or different and is independently selected from the group consisting of halo, alkyl, Ay, Het, —OR⁷, —C(O)Het, —C(O)NR⁷R⁸, —C(O)NHR¹⁰Het, —S(O)$_n$R⁹, —NR⁷R⁸, —NR⁷Ay, —NHHet, —NHR¹⁰Ay, —NHR¹⁰Het, —R¹⁰OR⁹ and cyano, or any subset thereof. In one particular embodiment wherein p is 1 or more, each $R^1$ is the same or different and is independently selected from the group consisting of halo, alkyl, Het, —OR⁷, —C(O)NR⁷R⁸, —S(O)$_n$R⁹, —NR⁷R⁸, —NR⁷Ay and —NHHet, or any subset thereof. In one embodiment, $R^1$ is —NR⁷R⁸.

More specifically, particular compounds of formula (I) are defined wherein p is 1 or more and each $R^1$ is the same or different and is independently selected from the group consisting of halo, alkyl, —NH₂, —NH-alkyl, —NH-cycloalkyl, —N(alkyl)(alkyl), phenyl, Het, —O-alkyl, —N(alkyl)-O-alkyl, —NHAy, —C(O)NH₂, —C(O)NH(alkyl), —C(O)N(alkyl)(alkyl) and —S-alkyl, or any subset thereof. More particularly, $R^1$ is selected from the group consisting of —NH-alkyl, —NH-cycloalkyl and pyrrolidone, or any subset thereof.

Specific examples of some particular $R^1$ groups are selected from the group consisting of Cl, methyl, ethyl, propyl, isopropyl, butyl, isobutyl, trifluoromethyl, —NH₂, —NH-methyl, —N(CH₃)₂, —NH-cyclopentyl, —NH-cyclopropyl, —NH-isopropyl, —NH-butyl, —NH-phenyl, —N(CH₂)₂OCH₃, pyrrolidine, methoxy, ethoxy, propoxy, isopropoxy, butoxy, thiomethoxy, thioethoxy, thioisopropoxy, and pyrrolidine, or any subset thereof.

In one embodiment, $R^7$ and $R^8$ are each the same or different and are each independently selected from the group consisting of H, alkyl, cycloalkyl, —C(O)R⁹, —R¹⁰-cycloalkyl, —R¹⁰R⁹, —R¹⁰NR⁹R¹¹ and —R¹⁰CO₂R⁹, or any subset thereof. More particularly, $R^7$ and $R^8$ are each the same or different and are each independently selected from the group consisting of H, alkyl, cycloalkyl, and —R¹⁰-cycloalkyl, or any subset thereof. In one embodiment, $R^7$ and $R^8$ are each the same or different and are each independently selected from the group consisting of H, alkyl and cycloalkyl.

The group —R¹⁰(OR¹⁰)$_w$ in the definition of $R^9$ and $R^{11}$ refers to a PEG-like chain. In one embodiment, $R^9$ and $R^{11}$ are each the same or different and are each independently selected from the group consisting of H, alkyl, cycloalkyl, and —R¹⁰-cycloalkyl, or any subset thereof. More particularly, $R^9$ and $R^{11}$ are each the same or different and are each independently selected from the group consisting of H and alkyl.

In one embodiment, $R^{10}$ is alkyl or cycloalkyl. In one embodiment, $R^{10}$ is alkyl. In another embodiment, the compounds of formula (I) include those compounds defined where $R^2$ does not contain an aryl, heterocyclic or heteroaryl moiety (or in one embodiment, $R^2$ does not contain a heterocyclic or heteroaryl moiety but may contain an aryl moiety). A particular embodiment includes those compounds of formula (I) where $R^2$ does contain an aryl, heterocyclic or heteroaryl moiety. Based on the guidance given above for $R^1$, one skilled in the art can readily determine the list of appropriate groups defining $R^2$ which contain or exclude aryl, heterocyclic or heteroaryl moieties.

In one embodiment, $R^2$ is selected from the group consisting of Ay, Het, —OR⁷, —OHet, —OR¹⁰Het, —S(O)$_n$R⁹, —NR⁷R⁸, —NHHet, —NHR¹⁰Het and —R¹⁰NR⁷R⁸, or any subset thereof. In one particular embodiment, $R^2$ is selected from the group consisting of Het, —NR⁷R⁸, —NHHet and —NHR¹⁰Het, or any subset thereof. In one particular embodiment, the compounds of formula (I) are defined wherein $R^2$ is selected from the group consisting of —NR⁷R⁸ and Het.

More specifically, in one embodiment, $R^2$ is selected from the group consisting of —NH₂, —NH-alkyl, —NH-cycloalkyl, —N(alkyl)(alkyl), Het, —O-alkyl, —N(alkyl)-O-alkyl, and —S-alkyl, or any subset thereof.

Specific examples of particular $R^2$ groups are selected from the group consisting of —NH₂, cyclopentylamine, cyclopropylamine, n-butylamine, pyrrolidine, —NCH₂CH₂OCH₃, —S-methyl, S-ethyl, and O-butyl, or any subset thereof.

In one class of compounds of formula (I), Y is CH. In another preferred class of compounds of formula (I), Y is N.

In another embodiment, the compounds of formula (I) include those compounds defined where at least one of $R^3$ and $R^4$ contains an aryl, heterocyclic or heteroaryl moiety (or contains a heterocyclic or heteroaryl moiety but exclude aryl moeities). Another embodiment includes those compounds of formula (I) where neither $R^3$ nor $R^4$ contain an aryl, heterocyclic or heteroaryl moiety (or neither contains a heterocyclic or heteroaryl moeity but may contain an aryl moiety). Based on the guidance given above for $R^1$, one skilled in the art can readily determine the list of appropriate groups defining $R^3$ and $R^4$ which contain or exclude aryl, heterocyclic and/or heteroaryl moeities.

In one embodiment, $R^3$ is selected from the group consisting of H, halo, alkyl, Ay, —OR⁷, —CO₂R⁷, —NR⁷R⁸, —R¹⁰OR⁷ and —R¹⁰NR⁷R⁸, or any subset thereof. More particularly, $R^3$ is selected from the group consisting of H, halo, alkyl, —OR⁷, and —NR⁷R⁸, or any subset thereof. In one particular embodiment, $R^3$ is H or alkyl. In one embodiment $R^3$ is H. In one particular embodiment, when Y is CH, $R^3$ is not —NR⁷Ay.

In one embodiment, $R^4$ is selected from the group consisting of H, halo, alkyl, Ay, —OR⁷, —CO₂R⁷, —NR⁷R⁸, —R¹⁰OR⁷ and —R¹⁰NR⁷R⁸, or any subset thereof. More particularly, $R^4$ is selected from the group consisting of H, halo, alkyl —OR⁷, and —NR⁷R⁸, or any subset thereof. In one embodiment, $R^4$ is H or alkyl. In one embodiment $R^4$ is H.

in formula (I) above is herein referred to as Ring A.

Ring A is a heterocyclic or heteroaryl group having from 5 to 10 members (including 1, 2, 3 or 4 heteroatoms selected from N, O and S).

Ring A may be bonded to the pyrazolopyridine core through any available atom including any available heteroatom. In one embodiment, Ring A contains at least one N atom and is bonded to the pyrazolopyridine core through N.

Examples of heterocyclic or heteroaryl groups having 5–10 members which are suitable as Ring A are selected from the group consisting of furan, pyridine, pyrimidine, thiazole, pyrazine, pyrrole, imidazole, oxazole, benzimidazole, quinoline, isoquinoline, and quinoxoline, or any subset thereof.

In one embodiment, Ring A is a heterocyclic or heteroaryl group having 9 members. In one particular embodiment, Ring A is a a heterocyclic or heteroaryl group having 5 or 6 members.

In one embodiment, Ring A in formula (I) is selected from the group consisting of furan, thiazole, pyridine and pyrimidine.

In one particular embodiment, q is selected from the group consisting of 0, 1 and 2. In one embodiment, q is 0. In one embodiment, q is 1.

$R^5$ may be in any suitable position on the heterocyclic or heteroaryl ring. $R^5$ may be bound to a carbon atom or to a suitable heteroatom (i.e., N). One skilled in the art will readily be able to ascertain suitable positions for attachment of the substituent(s) $R^5$.

One class of compounds of formula (I) includes those compounds defined wherein at least one of $R^5$ contains an aryl, heterocyclic or heteroaryl moiety (in one embodiment, a heterocyclic or heteroaryl moiety). Another class of compounds of formula (I) includes those compounds defined wherein no $R^5$ contains an aryl, heterocyclic or heteroaryl moiety (in one embodiment, a heterocyclic or heteroaryl moiety). Based on the guidance given above for $R^1$, one skilled in the art can readily determine the list of appropriate groups defining $R^5$ which contain or exclude aryl, heterocyclic or heteroaryl moeities.

In one embodiment, each $R^5$ is the same or different and is independently selected from the group consisting of halo, alkyl, alkenyl, Ay, Het, —$OR^7$, —$OAy$, —$CO_2R^9$, —$C(O)NR^7R^8$, —$C(O)NR^7Ay$, —$S(O)_2NR^7RB$, —$NR^7R^8$, —$NR^7Ay$, —$NHR^{10}Ay$, cyano, nitro and azido, or any subset thereof. More particularly, each $R^5$ is the same or different and is independently selected from the group consisting of halo, alkyl, alkenyl, Ay, Het, —$OR^7$, —$NR^7R^8$, —$NR^7Ay$, cyano, nitro, and azido, or any subset thereof. In one particular embodiment, each $R^5$ is the same or different and is independently selected from the group consisting of halo, alkyl, —$OR^7$, —$NR^7R^8$, cyano, nitro, and azido, or any subset thereof. A few specific embodiments of the compounds of formula (I) are defined where $R^5$ is selected from the group consisting of halo (e.g., fluoro or chloro), alkyl (e.g., methyl), O-alkyl (e.g., O-methyl, O-isobutyl, and

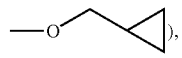),

O-allyl, cyano, —NH—$CH_3$, —$N(CH_3)_2$, nitro and azido, or any subset thereof.

It is to be understood that the present invention includes all combinations and subsets of the specifically mentioned and particular groups defined hereinabove.

Specific examples of compounds of formula (I) include but are not limited to:

N-Cyclopentyl-3-[2-(cyclopentylamino)-4-pyrimidinyl]-2-(4-pyridinyl)pyrazolo[1,5-a]pyridin-7-amine;

N-Cyclopentyl-3-[2-(methylamino)-4-pyrimidinyl]-2-(4-pyridinyl)pyrazolo[1,5-a]pyridin-7-amine;

N-cyclopentyl-3-[2-(cyclopentylamino)-4-pyrimidinyl]-2-(3-pyridinyl) pyrazolo[1,5-a]pyridin-7-amine;

N-Cyclopentyl-N-(4-{2-[2-(cyclopentylamino)-4-pyrimidinyl]pyrazolo[1,5-a]pyridin-3-yl}-2-pyrimidinyl)amine;

N-(4-{7-Chloro-2-[2-(cyclopentylamino)-4-pyrimidinyl]pyrazolo[1,5-a]pyridin-3-yl}-2-pyrimidinyl)-N-cyclopentylamine;

N-Cyclopentyl-2,3-bis[2-(cyclopentylamino)-4-pyrimidinyl]pyrazolo[1,5-a]pyridin-7-amine;

N-(2-Methoxyethyl)-2,3-bis{2-[(2-methoxyethyl)amino]pyrimidin-4-yl}pyrazolo[1,5-a]pyridin-7-amine;

N-Butyl-2,3-bis[2-(butylamino)pyrimidin-4-yl]pyrazolo[1,5-a]pyridin-7-amine;

N-Cyclopropyl-2,3-bis[2-(cyclopropylamino)pyrimidin-4-yl]pyrazolo[1,5-a]pyridin-7-amine;

7-Morpholin-4-yl-2,3-bis(2-morpholin-4-ylpyrimidin-4-yl)pyrazolo[1,5-a]pyridine;

N-Isobutyl-2,3-bis[2-(isobutylamino)pyrimidin-4-yl]pyrazolo[1,5-a]pyridin-7-amine;

N-Benzyl-2,3-bis[2-(benzylamino)pyrimidin-4-yl]pyrazolo[1,5-a]pyridin-7-amine;

N-Isopropyl-2,3-bis[2-(isopropylamino)pyrimidin-4-yl]pyrazolo[1,5-a]pyridin-7-amine;

2-(2-Fluoro-4-pyridinyl)-3-[2-(methylsulfanyl)-4-pyrimidinyl]pyrazolo[1,5-a]pyridine;

4-[2-(2-Fluoro-4-pyridinyl)pyrazolo[1,5-a]pyridin-3-yl]-N-isopropyl-2-pyrimidinamine;

N-Isopropyl-4-{2-[2-(isopropylamino)-4-pyridinyl]pyrazolo[1,5-a]pyridin-3-yl}-2-pyrimidinamine;

3-[2-(Cyclopropylamino)-4-pyrimidinyl]-N-isopropyl-2-[2-(isopropylamino)-4-pyridinyl]pyrazolo[1,5-a]pyridin-7-amine;

N-Cyclopentyl-2-[2-(cyclopentylamino)-4-pyridinyl]-3-[2-(isopropylamino)-4-pyrimidinyl]pyrazolo[1,5-a]pyridin-7-amine;

3-[2-(Cyclopentylamino)-4-pyrimidinyl]-N-isopropyl-2-[2-(isopropylamino)-4-pyridinyl]pyrazolo[1,5-a]pyridin-7-amine;

N-Cyclopentyl-3-[2-(cyclopentylamino)-4-pyrimidinyl]-2-[2-(isopropylamino)-4-pyridinyl]pyrazol o[1,5-a]pyridin-7-amine;

N-Cyclopentyl-3-[2-(cyclopentylamino)-4-pyrimidinyl]-2-(2-furyl) pyrazolo[1,5-a]pyridin-7-amine;

N-Cyclopentyl-3-[2-(cyclopentylamino)-4-pyrimidinyl]-2-(3-methyl-2-furyl)pyrazolo[1,5-a]pyridin-7-amine;

N-Cyclopentyl-3-[2-(cyclopropylamino)-4-pyrimidinyl]-2-(3-methyl-2-furyl)pyrazolo[1,5-a]pyridin-7-amine;

N-Cyclopropyl-3-[2-(cyclopropylamino)-4-pyrimidinyl]-2-(3-methyl-2-furyl)pyrazolo[1,5-a]pyridin-7-amine;

N-Cyclopentyl-3-[2-(cyclopentylamino)-4-pyrimidinyl-2-(2-furyl)pyrazolo[1,5-a]pyridin-7-amine;

3-[2-(Cyclopentylamino)-4-pyrimidinyl]-N-cyclopropyl-2-(2-furyl)pyrazolo[1,5-a]pyridin-7-amine;

2-(5-Bromo-2-furyl)-N-cyclopentyl-3-[2-(cyclopentylamino)-4-pyrimidinyl]pyrazolo[1,5-a]pyridin-7-amine; and N-Cyclopentyl-3-[2-(cyclopentylamino)-4-pyridinyl]-2-(2-methyl-1,3-thiazol-4-yl)pyrazolo[1,5-a]pyridin-7-amine;

and pharmaceutically acceptable salts, solvates and physiologically functional derivatives thereof.

It will be appreciated by those skilled in the art that the compounds of the present invention may also be utilized in the form of a pharmaceutically acceptable salt, solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of formula (I) are in the form of the mesylate salt Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes descibed below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) and intermediates used in the processes of preparing compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV)) (including CMV in organ transplant patients being treated with immunosupressants), Epstein Barr virus (EBV), varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from restenosis following angioplasty, viral infection, particularly by CMV and/or HHV-6 plays a pivotal role in the proliferation of the smooth muscle cells in the coronary vessel. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B and hepatitis C viruses, human papilloma virus (HPV) and HIV.

The present invention provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome or multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome or multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the compound of formula (I) in the preparation of a medicament for the treatment of a condition or disease associated with a herpes viral infection; and the use of the compound of formula (I) in the preparation of a medicament for the treatment or prophylaxis of hepatitis B or hepatitis C viruses, human papilloma virus or HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis or atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical composition. The pharmaceutical composition may further comprise one or more pharmaceutically acceptable carriers or diluents together with the compound of formula (I). The carrier(s) or diluents must be "acceptable" in the sense of being compatible with the other ingredients of the formulation and not deleterious to the recipient thereof.

Accordingly, the present invention further provides for a pharmaceutical composition or formulation comprising a compound of formula (I). In one embodiment, the pharmaceutical formulation further comprises one or more pharmaceutically acceptable carriers or dilents and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules (including soft-gel capsules), cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described. Formulations for rectal administration may be presented as a suppository with the usual carriers such as cocoa butter, hard fat or polyethylene glycol.

Formulations for topical (e.g., dermal) or intranasal administration include ointments, creams, lotions, pastes, gels, sprays, aerosols and oils. Suitable carriers for such formulations including petroleum jelly, lanolin, polyethylene glycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleoside reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, ganciclovir, docosanol, miribavir, amprenavir, lamivudine, zidovudine, and abacavir. Preferred antiviral agents for combining with the compounds of the present invention include aciclovir, fameyclovir and valaciclovir. Thus the present invention provides in a further aspect, a combination comprising a compound of formula (I) and an antiviral agent selected from the group consisting of aciclovir or valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein Y is N, and $R^3$ and $R^4$ are H, may be conveniently prepared by the process outlined in Scheme 1 below.

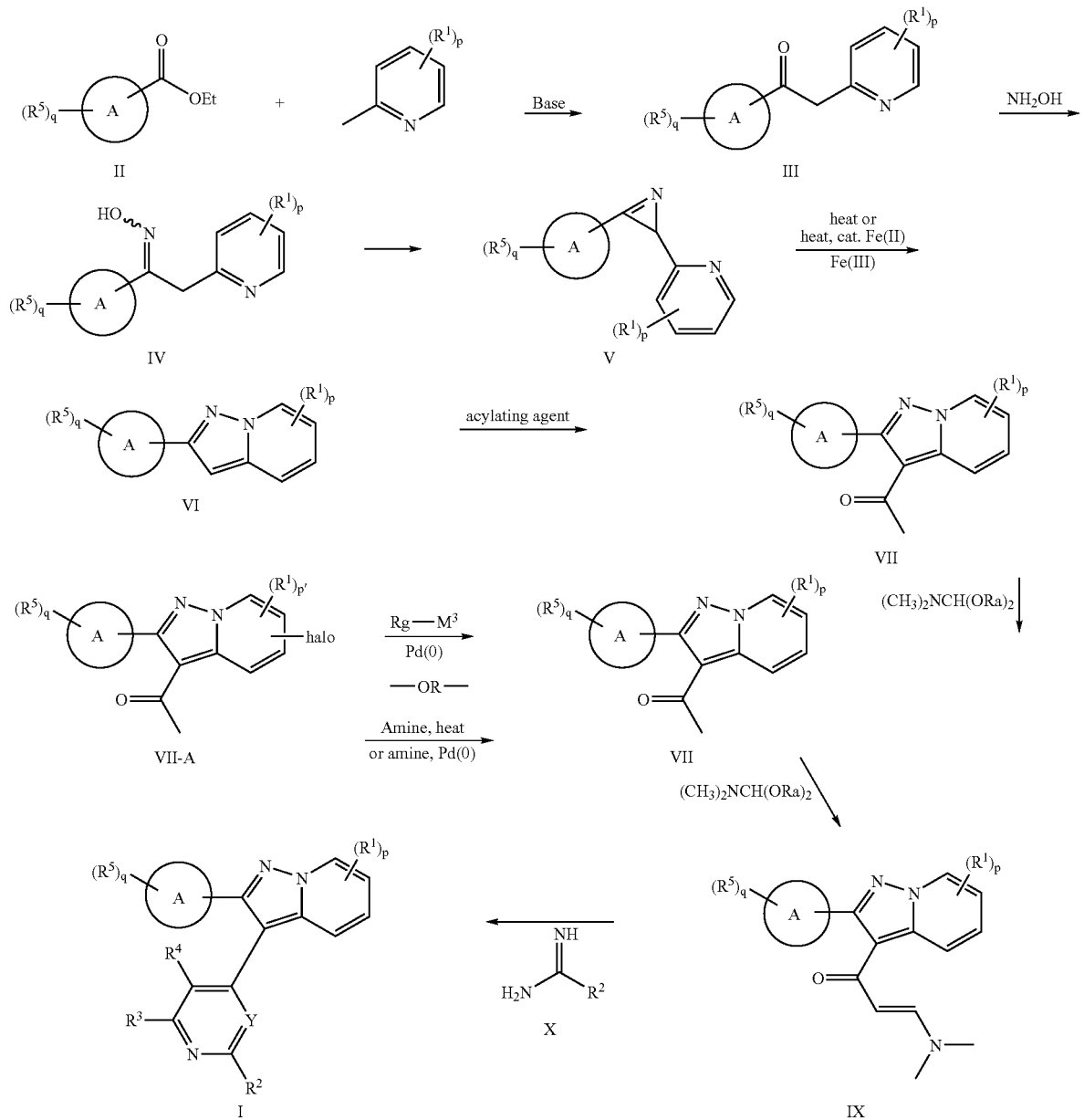

Scheme 1 wherein:
p is 0, 1, 2, 3 or 4;
p' is 0, 1, 2 or 3;
each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)N$R^7R^8$, —C(O)N$R^7$Ay, —C(O)NH$R^{10}$Ay, —C(O)NH$R^{10}$Het, —C(S)N$R^9R^{11}$, —C(NH)N$R^7R^8$, —C(NH)N$R^7$Ay, —S(O)$_n$$R^9$, —S(O)$_n$Ay, —S(O)$_n$Het, —$SO_2$N$R^7R^8$, —$SO_2$N$R^7$Ay, —N$R^7R^8$, —N$R^7$Ay, —NHHet, —NH$R^{10}$Ay, —NH$R^{10}$Het, —$R^{10}$cycloalkyl, —$R^{10}$Ay, —$R^{10}$Het, —$R^{10}$O—C(O)$R^9$, —$R^{10}$O—C(O)Ay, —$R^{10}$O—C(O)Het, —$R^{10}$O—S(O)$_n$$R^9$, —$R^{10}R^9$, —$R^{10}$C(O)$R^9$,
—$R^{10}CO_2R^9$, —$R^{10}$C(O)N$R^9R^{11}$, —$R^{10}$C(O)N$R^7$Ay, —$R^{10}$C(O)NH$R^{10}$Het, —$R^{10}$C(S)N$R^9R^{11}$, —$R^{10}$C(NH)N$R^9R^{11}$, —$R^{10}SO_2R^9$, —$R^{10}SO_2$N$R^9R^{11}$, —$R^{10}SO_2$NHCO$R^9$, —$R^{10}$N$R^7R^8$, —$R^{10}$N$R^7$Ay, —$R^{10}$NHC(NH)N$R^9R^{11}$, cyano, nitro and azido;
or two adjacent $R^1$ groups together with the carbon atoms to which they are bonded form a cycloalkyl or a 5- or 6-membered heterocyclic group containing 1 or 2 heteroatoms;
each $R^7$ and $R^8$ are the same or different and are independently selected from the group consisting of H, alkyl, alkenyl, cycloalkyl, cycloalkenyl, —C(O)$R^9$, —$CO_2R^9$, —C(O)N$R^9R^{11}$, —C(S)N$R^9R^{11}$, —C(NH)N$R^9R^{11}$, —$SO_2R^{10}$, —$SO_2$N$R^9R^{11}$, —$R^{10}$cycloalkyl, —$R^{10}$O$R^9$, —$R^{10}$C(O)$R^9$, —$R^{10}CO_2R^9$, —$R^{10}$C(O)

NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹;

each R⁹ and R¹¹ are the same or different and are independently selected from the group consisting of H, alkyl, cycloalkyl, —R¹⁰ cycloalkyl, —R¹⁰OH, —R₁₀(OR¹⁰)_w wherein w is 1–10, and —R¹⁰NR¹⁰R¹⁰;

each R¹⁰ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

Y is N;

R² is selected from the group consisting of halo, alkyl, alkenyl, cycloalkyl, cycloalkenyl, Ay, Het, —OR⁷—OAy, —OHet, —OR¹⁰Het, —S(O)_nR⁹, —S(O)_nAy, —S(O)_nHet, —S(O)_nNR⁷R⁸, —NR⁷R⁸, —NHHet, —NHR¹⁰Ay, —NHR¹⁰Het, —R¹⁰NR⁷R⁸ and —R¹⁰NR⁷Ay;

n is 0, 1 or 2;

R³ and R⁴ are H;

Ring A is a heterocyclic or heteroaryl group having from 5 to 10 members;

q is 0, 1, 2, 3, 4 or 5; and each R⁵ is the same or different and is independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)_nR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido;

Rg is Ay or Het as defined above;

M³ is B(OH)₂, B(ORa)₂, B(Ra)₂, Sn(Ra)₃, Zn-halide, Zn—Ra or Mg-halide; and

Ra is alkyl or cycloalkyl; and all other variables are defined above.

Generally, the process for preparing the compounds of formula (I) wherein Y is N and R³ and R⁴ are H, (all formulas and all other variables having been defined above in connection with Scheme 1) comprises the steps of:

(a) reacting a picoline with an ester of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (O) to prepare a compound of formula (VI);

(e) acylating the compound of formula (VI) to prepare a compound of formula (f) when at least one R¹ is halogen (i.e., a compound of formula (VI-A)), either:

(1) replacing the halogen of the compound of formula (VII-A) with an amine to prepare a compound of formula (VII); or (2) coupling the compound of formula (VII-A) with a metal compound of formula Rg—M³ to prepare a compound of formula (VII);

(g) reacting the compound of formula (VII) with a dimethylformamide dialkyl acetal of formula (CH₃)₂NCH(ORa)₂ to prepare a compound of formula (IX); and (h) reacting the compound of formula (IX) with a compound of formula (X) to prepare a compound of formula (I).

More specifically, compounds of formula (I) wherein Y is N and R³ and R⁴ are H can be prepared by reacting a compound of formula (IX) with a compound of formula (X).

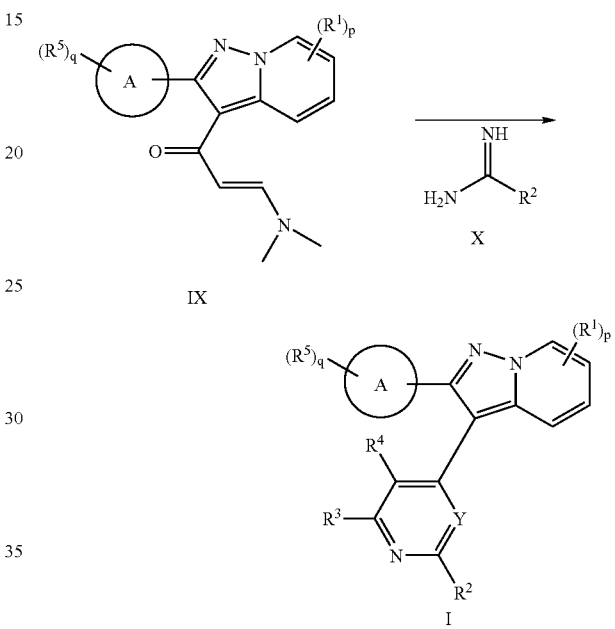

wherein all variables are as defined above in connection with Scheme 1.

This method can be readily carried out by mixing a compound of formula (IX) with a compound of formula (X) in a suitable solvent, optionally in the presence of a base (particularly when the amidine is in a salt form), and heating the reaction to 50–150° C. Typical solvents include lower alcohols such as methanol, ethanol, isopropanol and the like and N,N-dimethylformamide. The base is typically a sodium alkoxide, potassium carbonate, or an amine base such as triethylamine. In one embodiment, the solvent is N,N-dimethylformamide and the base is potassium carbonate, or an amine base such as triethylamine.

Compounds of formula (IX) may be conveniently prepared by reacting a compound of formula (VII) with a dimethylformamide dialkyl acetal, wherein R_a is alkyl or cycloalkyl.

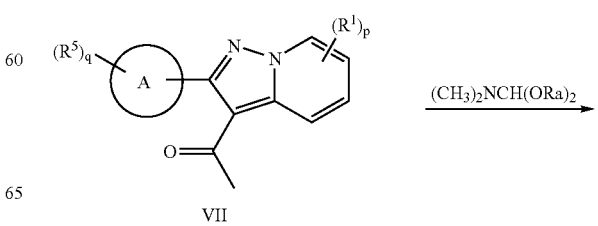

-continued

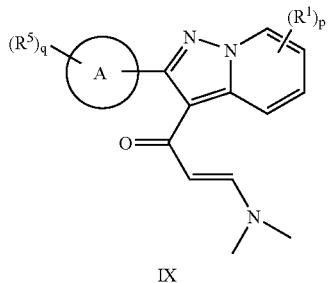

IX wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VII) with the dimethylformamide dialkyl acetal, optionally with heating.

For a compound of formula (VII-A) where at least one $R^1$ is halogen a compound of the formula (VII) may be prepared by two general methods. According to one method, a compound of formula (VII) is prepared from a compound of formula (VII-A) by replacement of the halogen with an amine nucleophile.

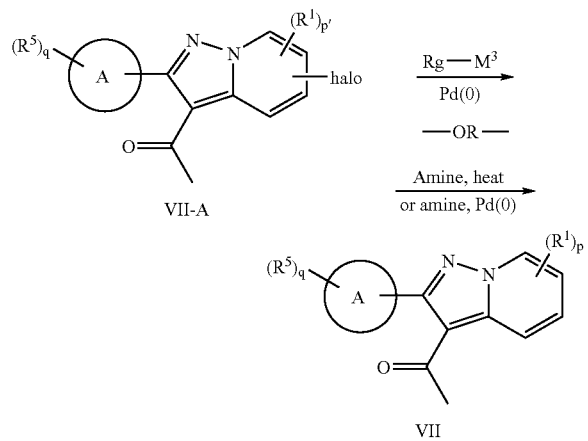

wherein all variables are as defined above in connection with Scheme 1.

Typically the replacement is carried out by mixing the compound of formula (VII-A) with an amine nucleophile selected from the group consisting of —NHR$^{10}$Ay, —NR$^7$Ay, Het, —NHHet, —NHR$^{10}$Het and —NR$^7$R$^8$; and optionally heating the reaction. The reaction can also be carried out via an adaptation of procedures found in the literature (Wolfe, J. P.; Buchwald, S. L. *J. Org. Chem.* 2000, 65, 1144) wherein a compound of formula (VII-A) is treated with an amine, a palladium (0) or nickel (O) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

According to the second method, a compound of formula (VII-A) is converted to a compound of formula (VII) by coupling with a metal compound of formula Rg—M$^3$ wherein Rg is Ay or Het and M$^3$ is B(OH)$_2$, B(ORa)$_2$, B(Ra)$_2$, Sn(Ra)$_3$, Zn-halide; Zn—Ra or Mg-halide, wherein Ra is alkyl or cycloalkyl and halide is halo. This general method can be conveniently performed in an inert solvent, in the presence of a palladium (0) catalyst, optionally with heating. In an embodiment, the reaction is performed by reacting equimolar amounts of a compound of formula (VII-A) with the metal compound of formula Rg—M$^3$ or optionally adding an excess of the metal compound. The palladium catalyst is typically present in 1–10 mol % compared to the compound of formula (VII-A). Palladium catalysts that may be used may include, but are not limited to, tetrakistriphenylphosphine palladium (0) dichlorobis (triphenylphosphine)-palladium(II), and bis(diphenylphosphinoferrocene)-palladium (II) dichloride. Inert solvents for use in the reaction include but are not limited to, N,N-dimethylformamide, toluene, tetrahydrofuran, dioxane, and 1-methyl-2-pyrrolidinone.

When the metal compound of formula Rg—M$^3$ is an arylboronic acid or ester or an arylborinate, the reaction is more conveniently carried out by adding a base in a proportion equivalent to, or greater than, that of the metal compound.

Metal compounds of formula Rg—M$^3$ can be purchased from commercial sources or prepared either as discreet isolated compounds or generated in situ using methods known to one skilled in the art (Suzuki, A. *J. Organomet Chem.* 1999, 576, 147; Stille, J. *Angew. Chem. Int. Ed Engl.* 1986, 25, 508; Snieckus, V. *J. Org. Chem.* 1995, 60, 292.)

Compounds of the formula (VII) (including compounds of formula (VII-A) may be conveniently prepared from compounds of formula (VI) using an acylation procedure.

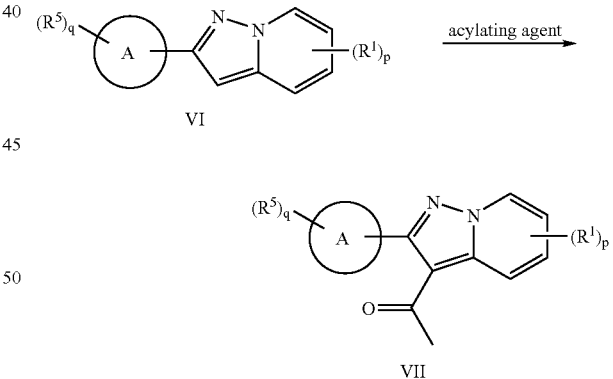

wherein all variables are as defined above in connection with Scheme 1.

Typically the acylation is carried out by treating the compound of formula (VI) with an acylating agent, optionally in the presence of an acid or Lewis acid catalyst in an inert solvent with optional heating. Typical acylating agents will be readily determined by those skilled in the art. One particular acylating agent is acetic anhydride. Lewis acid catalysts are also known to those skilled in the art. One particular Lewis acid catalyst for use in this reaction is boron trifluoride diethyl etherate. A suitable solvent is toluene.

A compound of formula (VI) is conveniently prepared by rearranging an azirine compound of formula (V).

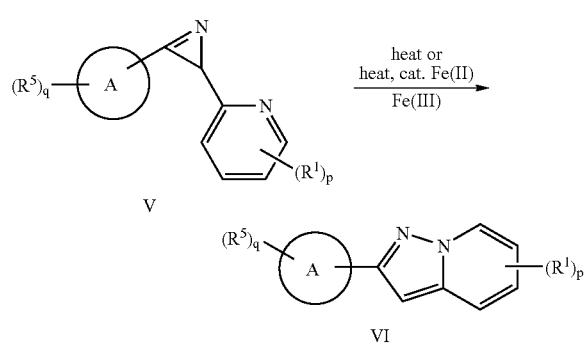

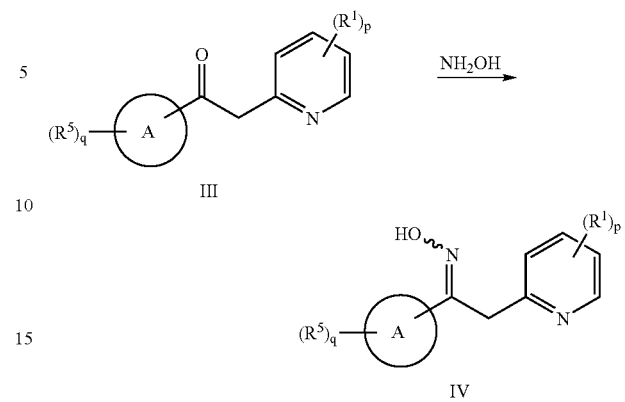

wherein all variables are as defined above in connection with Scheme 1.

The rearrangement of the azirine of formula (V) can be accomplished by heating a solution of the azirine of formula (V) in a suitable solvent at a temperature of about 160–200° C. Suitable inert solvents include, but are not limited to, 1-methyl-2-pyrrolidinone, and 1,2,4-trichlorobenzene. A particular method for rearrangement of the azirine of formula M to a compound of formula (VI) involves reacting the compound of formula (V) with ferrous chloride (FeCl$_2$) or ferric chloride (FeCl$_3$). This reaction is typically done in an inert solvent with heating. A particular solvent for this reaction is 1,2-dimethoxyethane and the like.

Typically the azirines of formula (V) are prepared from a corresponding oxime compound of formula (IV) by treatment with acylating or sulfonylating agents in the presence of a base.

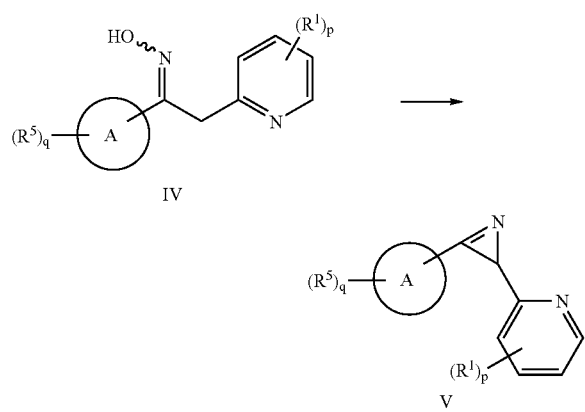

wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, and the like. The reaction may be carried out in an inert solvent such as for example, chloroform, dichloromethane, toluene or the like.

The oxime compounds of formula (IV) are readily prepared by treating a ketone compound of formula (III) with a hydroxylamine source, in a suitable solvent, and optionally with a base.

wherein all variables are as defined above in connection with Scheme 1.

Typically the hydroxylamine is hydroxylamine hydrochloride and the base is an aqueous solution of sodium hydroxide. Suitable solvents include lower alcohols such as methanol, ethanol, or isopropanol.

The ketone compounds of formula (III) can be prepared by treatment of a picoline with an ester of formula (II) in the presence of a base.

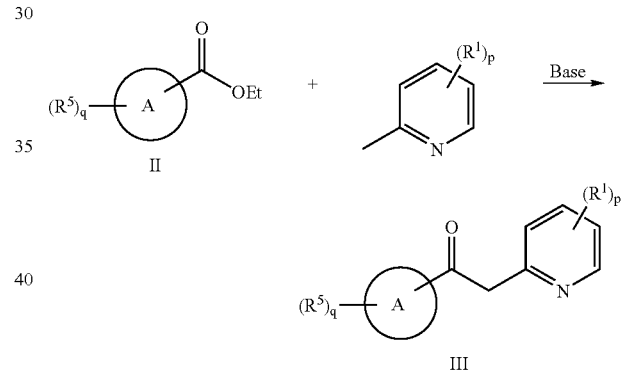

wherein all variables are as defined above in connection with Scheme 1.

An example of a suitable base is lithium bis(trimethylsilyl)amide in an inert solvent such as tetrahydrofuran. Ketones such as those of formula (III) can be readily prepared using procedures known to one skilled in the art and/or described in the literature (Cassity, R. P.; Taylor, LT.; Wolfe, J. F. *J.Org. Chem.* 1978, 2286). Compounds of formula (II) are commercially available or can be prepared by conventional means.

In addition to the foregoing process for preparing certain compounds of formula (I), the present invention also provides certain intermediate compounds for use in the preparation of such compounds of formula (I) according to the foregoing process. Such intermediates are described in Scheme 1 above.

In a further embodiment of the present invention, compounds of formula (I) wherein Y is N; R$^3$ is selected from the group consisting of of H, alkyl, cycloalkyl, alkenyl, Ay, Het, —OR$^7$, —OAy, —C(O)R$^7$, C(O)Ay, —CO$_2$R$^7$, —CO$_2$Ay, —SO$_2$NHR$^9$, —NR$^7$R$^8$(where R$^7$ and R$^8$ are not H), —NR$^7$Ay (where R$^7$ is not H), —R$^{10}$cycloalkyl, —R$^{10}$OR$^7$, —R¹⁰OAy, —R¹⁰NR⁷R⁸ and —R¹⁰NR⁷Ay; and R⁴ is H; and may be conveniently prepared by a process outlined in Scheme 2 below.

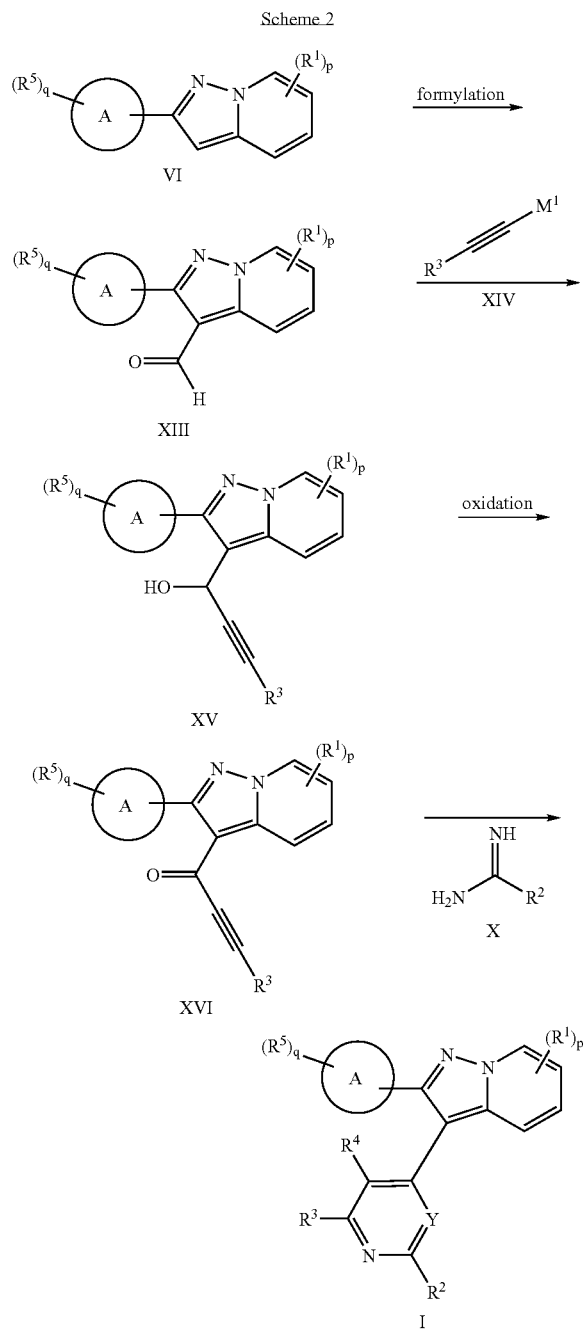

wherein:
p is 0, 1, 2, 3 or 4;
each R¹ is the same or different and is independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Ay, —C(O)NHR¹⁰Het, —C(S)NR⁹R¹¹, —C(NH)NR⁷R⁸, —C(NH)NR⁷Ay, —S(O)$_n$R⁹, —S(O)$_n$Ay, —S(O)$_n$Het, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Ay, —R¹⁰Het, —R¹⁰O—C(O)R⁹, —R¹⁰O—C(O)Ay, —R¹⁰O—C(O)Het, —R¹⁰OR⁹, —R¹⁰—S(O)$_n$R⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido;
or two adjacent R¹ groups together with the carbon atoms to which they are bonded form a cycloalkyl or a 5- or 6-membered heterocyclic group containing 1 or 2 heteroatoms;
each R⁷ and R⁸ are the same or different and are independently selected from the group consisting of H, alkyl, alkenyl, cycloalkyl, cycloalkenyl, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹;
each R⁹ and R¹¹ are the same or different and are independently selected from the group consisting of H, alkyl, cycloalkyl, —R¹⁰ cycloalkyl, —R¹⁰OH, —R₁₀(OR¹⁰)$_w$ wherein w is 1–10, and —R¹⁰NR¹⁰R¹⁰;
each R¹⁰ is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
Y is N;
R² is selected from the group consisting of halo, alkyl, alkenyl, cycloalkyl, cycloalkenyl, Ay, Het, —OR⁷—OAy, —OHet, —OR¹⁰Het, —S(O)$_n$R⁹, —S(O)$_n$Ay, —S(O)$_n$Het, —S(O)$_n$NR⁷R⁸, —NR⁷R⁸, —NHHet, —NHR¹⁰Ay, —NHR¹⁰Het, —R¹⁰NR⁷R⁸ and —R¹⁰NR⁷Ay;
n is 0, 1 or 2;
R³ is selected from the group consisting of H, alkyl, cycloalkyl, alkenyl, Ay, Het, —OR⁷, —OAy, —C(O)R⁷, C(O)Ay, —CO₂R⁷, —CO₂Ay, —SO₂NHR⁹, —NR⁷R⁸ (where R⁷ and R⁸ are not H), —NR⁷Ay (where R⁷ is not H), —R¹⁰cycloalkyl, —R¹⁰OR⁷, —R¹⁰OAy, R¹⁰NR⁷R⁸ and —R¹⁰NR⁷Ay;
R⁴ is H;
Ring A is a heterocyclic or heteroaryl group having from 5 to 10 members;
q is 0, 1, 2, 3, 4 or 5;
each R⁵ is the same or different and is independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het,, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; and
M¹ is Li, Mg-halide or cerium-halide.

Generally, the process for preparing compounds of formula (I) wherein Y is N; R³ is selected from the group consisting of of H, alkyl, cycloalkyl, alkenyl, Ay, Het, —OR⁷, —OAy, —C(O)R⁷, C(O)Ay, —CO₂R⁷, —CO₂Ay, —SO₂NHR⁹, —NR⁷R⁸ (where R⁷ and R⁸ are not H), —NR⁷Ay (where R⁷ is not H), —R¹⁰cycloalkyl, —R¹⁰OR⁷, —R¹⁰OAy, —R¹⁰NR⁷R⁸ and —R¹⁰NR⁷Ay; and R⁴ is H; comprises the following steps:

(a) formylating a compound of formula (VI) to prepare a compound of formula (XIII);

(b) reacting the compound of formula (XIII) with a compound of formula (XIV) to prepare a compound of formula (XV);

(c) oxidizing the compound of formula (XV) to prepare a compound of formula (XVI); and (d) reacting a compound of formula (XVI) with a compound of formula (X) to prepare a compound of formula (I).

More specifically, a compound of formula (I) may be prepared by reacting a compound of formula (XVI) with a compound of formula (X).

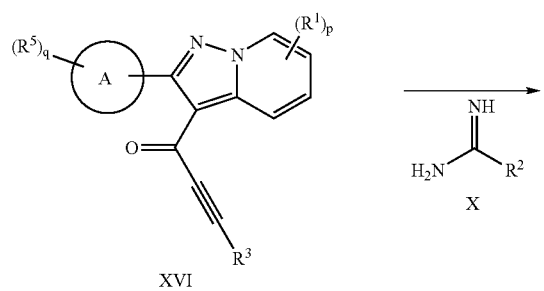

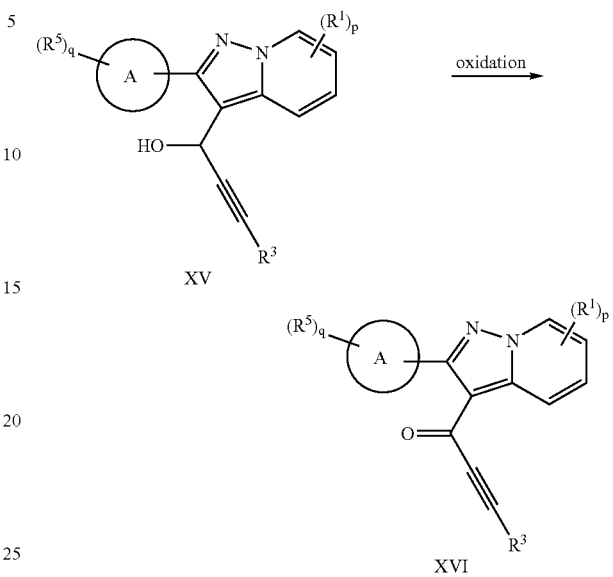

wherein all variables are as defined above in connection with Scheme 2.

This method can be readily carried out by mixing a compound of formula (XVI) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

A compound of formula (XVI) may be conveniently prepared by oxidation of a compound of formula (XV).

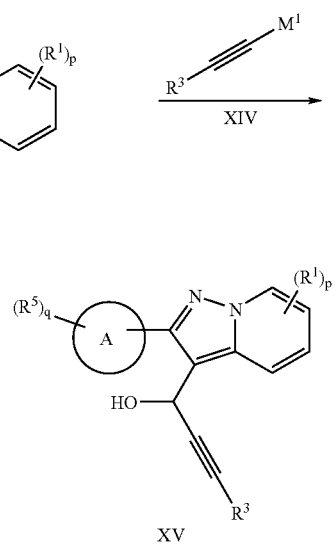

wherein all variables are as defined above in connection with Scheme 2.

Preferred oxidizing agents include but are not limited to, manganese dioxide, and the like, in an inert solvent. Suitable inert solvents include but are not limited to, dichloromethane, chloroform, N,N-dimethylformamide, ether, and the like.

A compound of formula (XV) may be conveniently prepared by reacting a compound of formula (XIII) with a compound of formula (XIV).

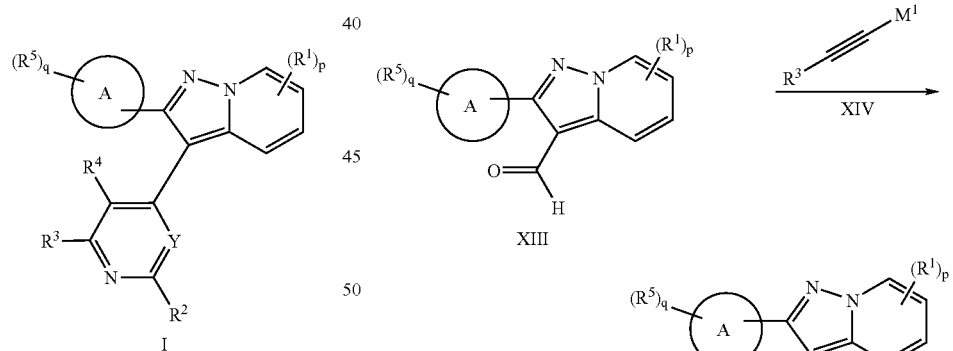

wherein all variables are as defined above in connection with Scheme 2.

Particular metals (M¹) in the compounds of formula (XIV) include but are not limited to, lithium, magnesium(II) halides, cerium(III) halides, and the like. Compounds of formula (XIV) may be purchased from commercial sources or prepared by methods known to one skilled in the art.

A ompound of formula (XIII) may be conveniently prepared from a compound of formula (VI) by a formylation procedure.

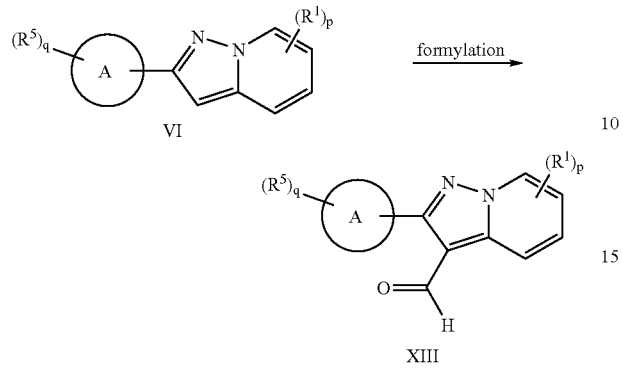

wherein all variables are as defined above in connection with Scheme 2.

Typically the formulation is carried out via the Vilsmeier-Haack reaction. The Vilsmeier-Haack reagents can be purchased from commercial sources or prepared in situ. Typical conditions include, but are not limited to treating compounds of formula (VI) with a premixed solution of phosphorous oxychloride in N,N-dimethylformamide optionally with heating the reaction to 50–150° C.

The compounds of formula (VI) are prepared by the process described in Scheme 1 above.

In addition to the foregoing process for preparing certain compounds of formula (I), the present invention also provides certain intermediate compounds for use in the preparation of such compounds of formula (I) according to the foregoing process. Such intermediates are described in Scheme 2 above.

A compound of formula (I) wherein Y is N may be conveniently prepared by a process outlined in Scheme 3 below.

Scheme 3

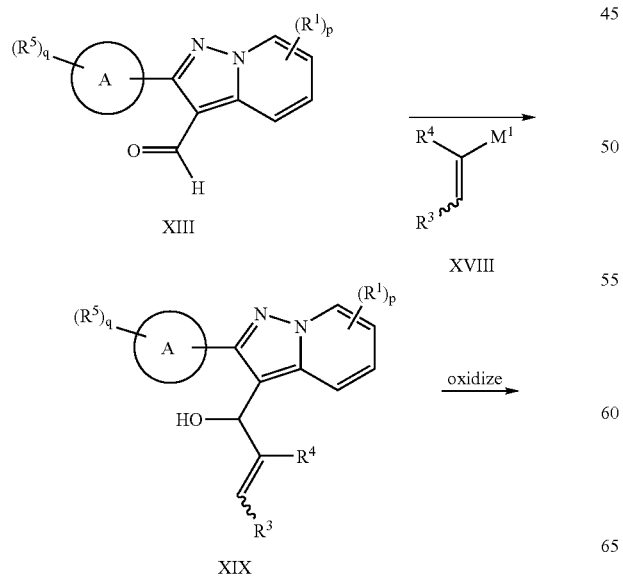

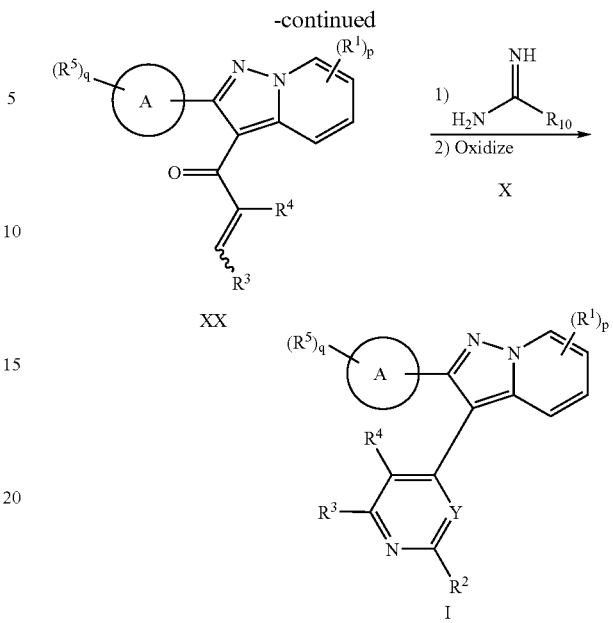

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—$C(O)R^9$, —$R^{10}$O—C(O)Ay, —$R^{10}$O—C(O)Het, —$R^{10}$O—$S(O)_nR^9$, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido;

or two adjacent $R^1$ groups together with the carbon atoms to which they are bonded form a cycloalkyl or a 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$;

each $R^9$ and $R^{11}$ are the same or different and are independently selected from the group consisting of H, alkyl, cycloalkyl, —$R^{10}$ cycloalkyl, —$R^{10}$OH, —$R_{10}(OR^{10})_w$ wherein w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

Y is N;

$R^2$ is selected from the group consisting of halo, alkyl, alkenyl, cycloalkyl, cycloalkenyl, Ay, Het, $-OR^7$, $-OAy$, $-OHet$, $-OR^{10}Het$, $-S(O)_nR^9$, $-S(O)_nAy$, $-S(O)_nHet$, $-S(O)_nNR^7R^8$, $-NR^7R^8$, $-NHHet$, $-NHR^{10}Ay$, $-NHR^{10}Het$, $-R^{10}NR^7R^8$ and $-R^{10}NR^7Ay$;

n is 0, 1 or 2;

$R^3$ and $R^4$ are the same or different and are each independently selected from the group consisting of H, halo, alkyl, alkenyl, cycloalkyl, Ay, Het, $-OR^7$, $-OAy$, $-C(O)R^7$, $C(O)Ay$, $-CO_2R^7$, $-CO_2Ay$, $-SO_2NHR^9$, $-NR^7R^8$, $-NR^7Ay$, $-NHHet$, $-NHR^{10}Het$, $-R^{10}$cycloalkyl, $-R^{10}OR^7$, $-R^{10}OAy$, $-R^{10}NR^7R^8$ and $-R^{10}NR^7Ay$;

Ring A is a 5–10 membered heterocyclic or heteroaryl group;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, $-OR^7$, $-OAy$, $-OR^{10}Ay$, $-OHet$, $-OR^{10}Het$, $-C(O)R^9$, $-C(O)Ay$, $-C(O)Het$, $-CO_2R^9$, $-C(O)NR^7R^8$, $-C(O)NR^7Ay$, $-C(O)NHR^{10}Het$, $-C(S)NR^9R^{11}$, $-C(NH)NR^7R^8$, $-C(NH)NR^7Ay$, $-S(O)_nR^9$, $-S(O)_2NR^7R^8$, $-S(O)_2NR^7Ay$, $-NR^7R^8$, $-NR^7Ay$, $-NHHet$, $-NHR^{10}Ay$, $-NHR^{10}Het$, $-R^{10}$cycloalkyl, $-R^{10}Het$, $-R^{10}OR^9$, $-R^{10}C(O)R^9$, $-R^{10}CO_2R^9$, $-R^{10}C(O)NR^9R^{11}$, $-R^{10}C(O)NR^7Ay$, $-R^{10}C(O)NHR^{10}Het$, $-R^{10}C(S)NR^9R^{11}$, $-R^{10}C(NH)NR^9R^{11}$, $-R^{10}SO_2R^9$, $-R^{10}SO_2NR^9R^{11}$, $-R^{10}SO_2NHCOR^9$, $-R^{10}NR^7R^8$, $-R^{10}NR^7Ay$, $-R^{10}NHC(NH)NR^9R^{11}$, cyano, nitro and azido; and $M^1$ is Li, Mg-halide or cerium-halide, wherein halide is halo.

Generally, the process for preparing compounds of formula (I) wherein Y is N comprises the following steps:

(a) reacting a compound of formula (XIII) with a compound of formula (XVIII) to prepare a compound of formula (XIX);

(b) oxidizing the compound of formula (XIX) to prepare a compound of formula (XX); and (c) reacting a compound of formula (XX) with a compound of formula (X) followed by oxidative aromatization to prepare a compound of formula (I).

More specifically, a compound of formula (I) can be prepared by reacting a compound of formula (XX) with a compound of formula (X) followed by oxidative aromatization.

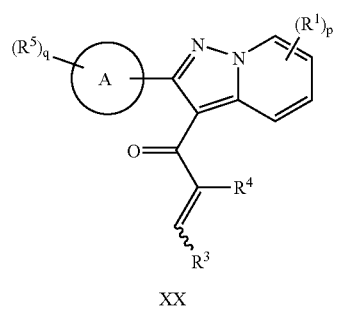

XX

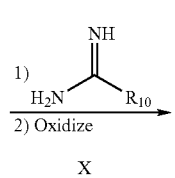

X

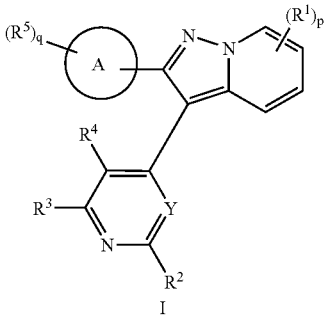

I wherein all variables are as defined above in connection with Scheme 3.

The condensation is conveniently carried out by treating the compound of formula (XX) with a compound of formula (X) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Conveniently in the same reaction vessel, the dihydropyrimidine intermediate may be oxidized to a compound of formula (I) by the addition of an oxidizing agent The reaction may be heated to 50–150° C. or performed at ambient temperature. Typically, the oxidizing agent is oxygen ($O_2$), palladium on carbon, 2,3-dichloro-5,6-dicyano-1,4 benzoquinone, or the like.

A compound of formula (XX) may be conveniently prepared by oxidation of a compound of formula (XIX).

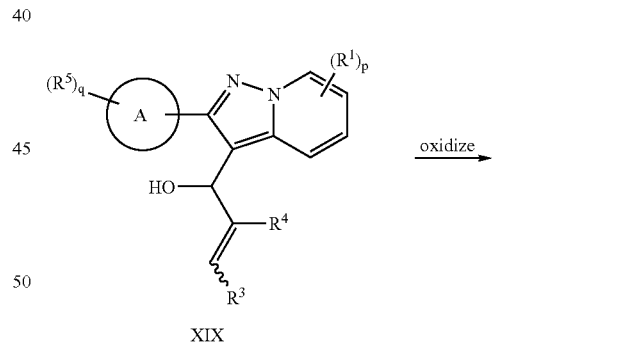

XIX

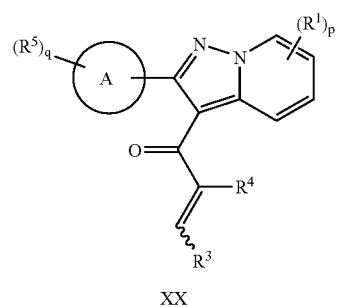

XX wherein all variables are as defined above in connection with Scheme 3.

Suitable oxidizing agents for the oxidation of compounds of formula (XIX) include but are not limited to manganese dioxide, and the like. The oxidation is typically carried out in an inert solvent such as for example, dichloromethane, chloroform, N,N-dimethylformamide, ether, and the like.

A compound of formula (XIX) may be conveniently prepared by reacting a compound of formula (XIII) with a compound of formula (XVIII).

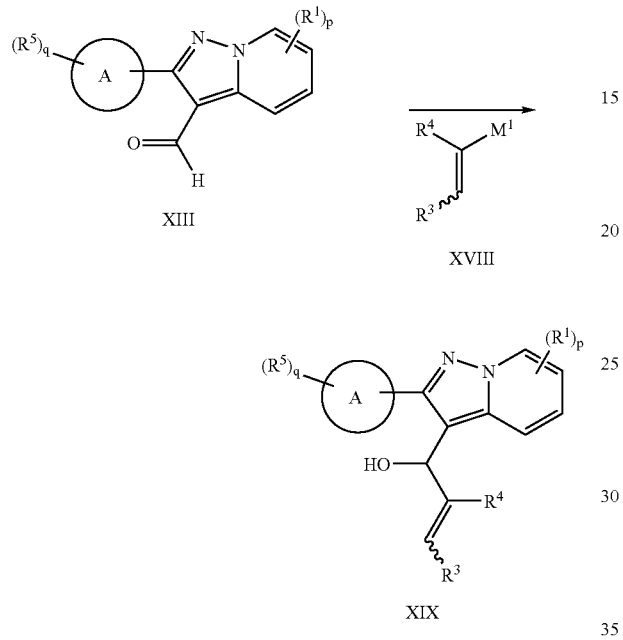

wherein $M^1$ is a metal such as for example, lithium, magnesium(II) halides, cerium(III) halides, and the like and all other variables are as defined above in connection with Scheme 3.

Compounds of formula (XVIII) may be purchased from commercial sources or prepared by methods known to one skilled in the art. The compounds of formula (XIII) may be prepared using the methods described in connection with Schemes 1 and 2 above.

In addition to the foregoing process for preparing certain compounds of formula (I), the present invention also provides certain intermediate compounds for use in the preparation of such compounds of formula (I) according to the foregoing process. Such intermediates are described in Scheme 3 above.

A compounds of formula (I) wherein Y is CH or N, may be conveniently prepared by a process outlined in Scheme 4 below.

Scheme 4

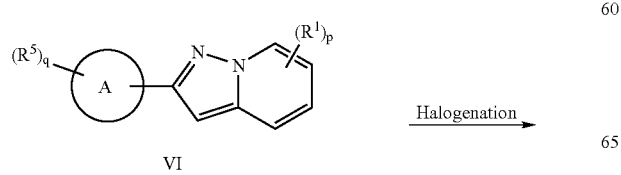

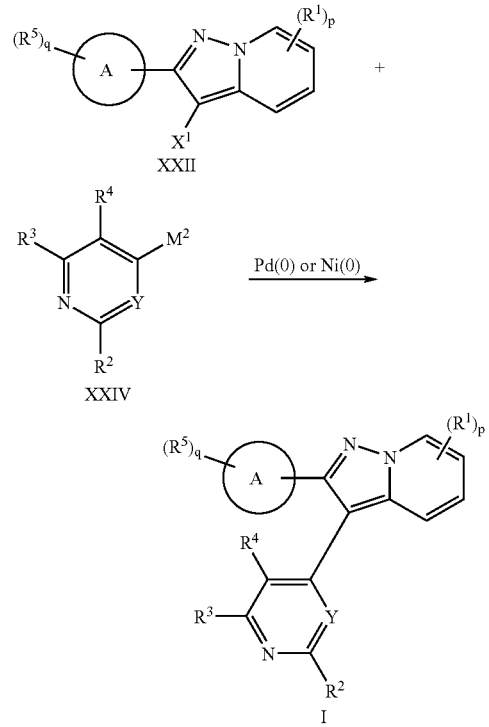

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, $-OR^7$, $-OAy$, $-OR^{10}Ay$, $-OHet$, $-OR^{10}Het$, $-C(O)R^9$, $-C(O)Ay$, $-C(O)Het$, $-CO_2R^9$, $-C(O)NR^7R^8$, $-C(O)NR^7Ay$, $-C(O)NHR^{10}Ay$, $-C(O)NHR^{10}Het$, $-C(S)NR^9R^{11}$, $-C(NH)NR^7R^8$, $-C(NH)NR^7Ay$, $-S(O)_nR^9$, $-S(O)_nAy$, $-S(O)_nHet$, $-S(O)_2NR^7R^8$, $-S(O)_2NR^7Ay$, $-NR^7R^8$, $-NR^7Ay$, $-NHHet$, $-NHR^{10}Ay$, $-NHR^{10}Het$, $-R^{10}$cycloalkyl, $-R^{10}Ay$, $-R^{10}Het$, $-R^{10}O-C(O)R^9$, $-R^{10}O-C(O)Ay$, $-R^{10}O-C(O)Het$, $-R^{10}O-S(O)_nR^9$, $-R^{10}OR^9$, $-R^{10}C(O)R^9$, $-R^{10}CO_2R^9$, $-R^{10}C(O)NR^9R^{11}$, $-R^{10}C(O)NR^7Ay$, $-R^{10}C(O)NHR^{10}Het$, $-R^{10}C(S)NR^9R^{11}$, $-R^{10}C(NH)NR^9R^{11}$, $-R^{10}SO_2R^9$, $-R^{10}SO_2NR^9R^{11}$, $-R^{10}SO_2NHCOR^9$, $-R^{10}NR^7R^8$, $-R^{10}NR^7Ay$, $-R^{10}NHC(NH)NR^9R^{11}$, cyano, nitro and azido;

or two adjacent $R^1$ groups together with the carbon atoms to which they are bonded form a cycloalkyl or a 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, $-C(O)R^9$, $-CO_2R^9$, $-C(O)NR^9R^{11}$, $-C(S)NR^9R^{11}$, $-C(NH)NR^9R^{11}$, $-SO_2R^{10}$, $-SO_2NR^9R^{11}$, $-R^{10}$cycloalkyl, $-R^{10}OR^9$, $-R^{10}C(O)R^9$, $-R^{10}CO_2R^9$, $-R^{10}C(O)NR^9R^{11}$, $-R^{10}C(S)NR^9R^{11}$, $-R^{10}C(NH)NR^9R^{11}$, $-R^{10}SO_2R^{10}$, $-R^{10}SO_2NR^9R^{11}$, $-R^{10}SO_2NHCOR^9$, $-R^{10}NR^9R^{11}$, $-R^{10}NHCOR^9$, $-R^{10}NHSO_2R^9$ and $-R^{10}NHC(NH)NR^9R^{11}$;

each $R^9$ and $R^{11}$ are the same or different and are independently selected from the group consisting of H, alkyl, cycloalkyl, —R¹⁰cycloalkyl, —R¹⁰OH, —R₁₀(OR¹⁰)$_w$ wherein w is 1–10, and —R¹⁰NR¹⁰R¹⁰;

each R¹⁰ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

Y is N or CH;

R² is selected from the group consisting of halo, alkyl, alkenyl, cycloalkyl, cycloalkenyl, Ay, Het, —OR⁷, —OAy, —OHet, —OR¹⁰Het, —S(O)$_n$R⁹, —S(O)$_n$Ay, —S(O)$_n$Het, —S(O)$_n$NR⁷R⁸, —NR⁷R⁸, —NHHet, —NHR¹⁰Ay, —NHR¹⁰Het, —R¹⁰NR⁷R⁸ and —R¹⁰NR⁷Ay;

n is 0, 1 or 2;

R³ and R⁴ are the same or different and are each independently selected from the group consisting of H, halo, alkyl, alkenyl, cycloalkyl, Ay, Het, —OR⁷, —OAy, —C(O)R⁷, C(O)Ay, —CO₂R⁷, —CO₂Ay, —SO₂NHR⁹, —NR⁷R⁸, —NR⁷Ay, —NHHet, —NHR¹⁰Het, —R¹⁰cycloalkyl, —R¹⁰OR⁷, —R¹⁰OAy, —R¹⁰NR⁷R⁸ and —R¹⁰NR⁷Ay;

Ring A is a 5–10 membered heterocyclic or heteroaryl group;

q is 0, 1, 2, 3, 4 or 5;

each R⁵ is the same or different and is independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido;

X¹ is chloro, bromo, or iodo; and

M² is —B(OH)₂, —B(ORa)₂, —B(Ra)₂, —Sn(Ra)₃, Zn-halide, ZnRa, or Mg-halide where Ra is alkyl or cycloalkyl and halide is halo.

Generally, the process for preparing compounds of formula (I) (all formulas and variables having been defined above in connection with Scheme 4), comprises the following steps:

a) halogenating a compound of formula (VI) to prepare a compound of formula (XXII); and b) reacting a compound of formula (XXII) with a compound of formula (XXIV) to prepare a compound of formula (I).

More specifically, a compound of formula (I) wherein Y is N or CH can be prepared by reacting a compound of formula (XXII) with a compound of formula (XXIV).

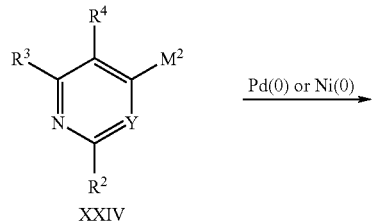

XXIV

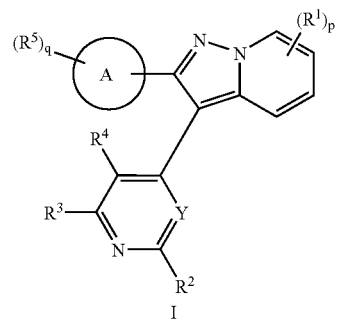

I wherein all variables are as defined above in connection with Scheme 4.

The reaction may be carried out in an inert solvent, in the presence of a palladium (0) or nickel (0) catalyst. The reaction may optionally be heated to about 50–150° C. Typically the reaction is performed by reacting equimolar amounts of a compound of formula (XXII) with a heteroaryl-metal compound of formula (XXIV), but the reaction may also be performed in the presence of an excess of compound of the formula (XXIV). The palladium or nickel catalyst is typically present in 1–10 mol % compared to the compound of formula (XXII). Examples of suitable palladium catalysts include but are not limited to, tetrakis(triphenylphosphine)palladium (0), dichlorobis(triphenylphosphine)palladium(II), tris(dibenzylideneacetone)dipalladium (0), and bis(diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the heteroaryl-metal compound of formula (XXIV) is an arylboronic acid or ester or an arylborinate the reaction is more conveniently carried out by adding a base in a proportion equivalent to, or greater than, that of the compound of formula (XXIV). Heteroaryl-metal compounds of formula (XXIV) may be obtained from commercial sources or prepared either as discreet isolated compounds or generated in situ using methods known to one skilled in the art. (Suzuki, A. *J. Organomet Chem.* 1999, 576, 147; Stille, J. *Angew. Chem. Int Ed. Engl.* 1986, 25, 508; Snieckus, V. *J. Org. Chem.* 1995, 60, 292.)

A compound of formula (XXII) can be prepared from a compound of formula (VI) by a halogenation procedure.

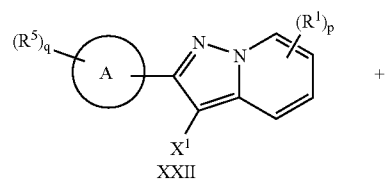

XXII

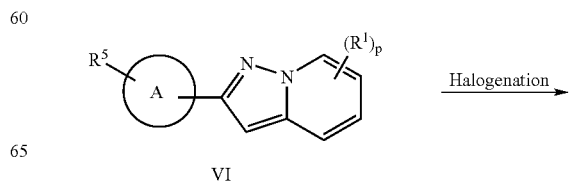

VI

-continued

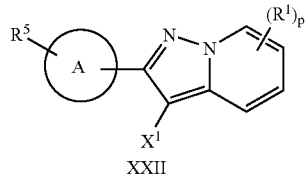

XXII wherein all variables are as defined above in connection with Scheme 4.

Typically, the halogenation reaction is carried out by subjecting the compound of formula (VI) to a halogenating agent in a suitable solvent. Suitable halogenating agents include but are not limited to, iodine, N-bromosuccinimide, trialkylammonium tribromides, bromine, N-chlorosuccinimide, N-iodosuccinimide, iodine, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

In addition to the foregoing process for preparing certain compounds of formula (I), the present invention also provides certain intermediate compounds for use in the preparation of such compounds of formula (I) according to the foregoing process. Such intermediates are described in Scheme 4 above.

In another embodiment, a compound of formula (I) may be conveniently prepared by a process outlined in Scheme 5 below

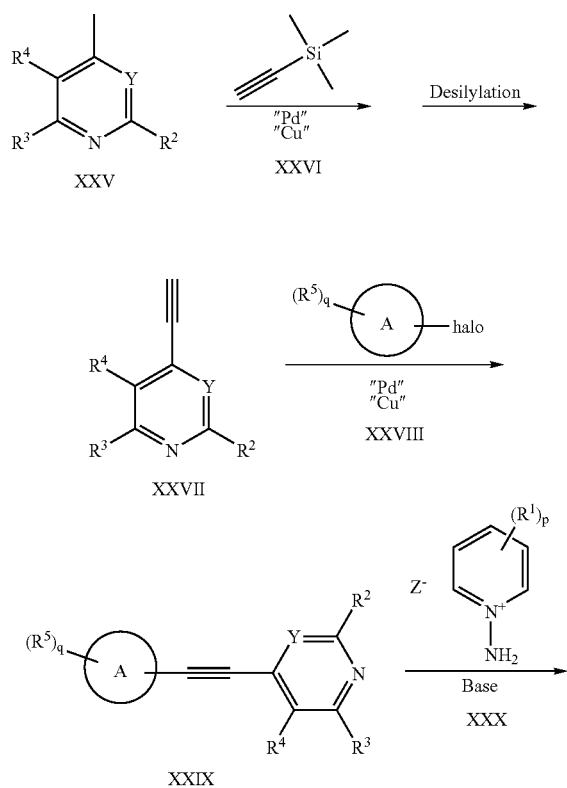

-continued

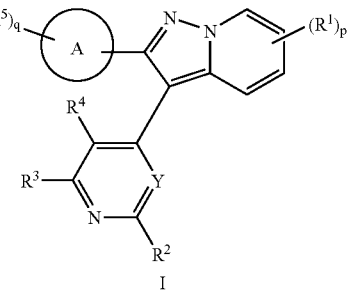

I wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, $-OR^7$, $-OAy$, $-OR^{10}Ay$, $-OHet$, $-OR^{10}Het$, $-C(O)R^9$, $-C(O)Ay$, $-C(O)Het$, $-CO_2R^9$, $-C(O)NR^7R^8$, $-C(O)NR^7Ay$, $-C(O)NHR^{10}Ay$, $-C(O)NHR^{10}Het$, $-C(S)NR^9R^{11}$, $-C(NH)NR^7R^8$, $-C(NH)NR^7Ay$, $-S(O)_nR^9$, $-S(O)_nAy$, $-S(O)_nHet$, $-S(O)_2NR^7R^8$, $-S(O)_2NR^7Ay$, $-NR^7R^8$, $-NR^7Ay$, $-NHHet$, $-NHR^{10}Ay$, $-NHR^{10}Het$, $-R^{10}cycloalkyl$, $-R^{10}Ay$, $-R^{10}Het$, $-R^{10}O-C(O)R^9$, $-R^{10}O-C(O)Ay$, $-R^{10}O-C(O)Het$, $-R^{10}O-S(O)_nR^9$, $-R^{10}OR^9$, $-R^{10}C(O)R^9$, $-R^{10}CO_2R^9$, $-R^{10}C(O)NR^9R^{11}$, $-R^{10}C(O)NR^7Ay$, $-R^{10}C(O)NHR^{10}Het$, $-R^{10}C(S)NR^9R^{11}$, $-R^{10}C(NH)NR^9R^{11}$, $-R^{10}SO_2R^9$, $-R^{10}SO_2NR^9R^{11}$, $-R^{10}SO_2NHCOR^9$, $-R^{10}NR^7R^8$, $-R^{10}NR^7Ay$, $-R^{10}NHC(NH)NR^9R^{11}$, cyano, nitro and azido;
or two adjacent $R^1$ groups together with the carbon atoms to which they are bonded form a cycloalkyl or a 5- or 6-membered heterocyclic group containing 1 or 2 heteroatoms;
each $R^7$ and $R^8$ are the same or different and are independently selected from the group consisting of H, alkyl, alkenyl, cycloalkyl, cycloalkenyl, $-C(O)R^9$, $-CO_2R^9$, $-C(O)NR^9R^{11}$, $-C(S)NR^9R^{11}$, $-C(NH)NR^9R^{11}$, $-SO_2R^{10}$, $-SO_2NR^9R^{11}$, $-R^{10}cycloalkyl$, $-R^{10}OR^9$, $-R^{10}C(O)R^9$, $-R^{10}CO_2R^9$, $-R^{10}C(O)NR^9R^{11}$, $-R^{10}C(S)NR^9R^{11}$, $-R^{10}C(NH)NR^9R^{11}$, $-R^{10}SO_2R^{10}$, $-R^{10}SO_2NR^9R^{11}$, $-R^{10}SO_2NHCOR^9$, $-R^{10}NR^9R^{11}$, $-R^{10}NHCOR^9$, $-R^{11}NHSO_2R^9$ and $-R^{10}NHC(NH)NR^9R^{11}$;
each $R^9$ and $R^{11}$ are the same or different and are independently selected from the group consisting of H, alkyl, cycloalkyl, $-R^{10}cycloalkyl$, $-R^{10}OH$, $-R^{10}(OR^{10})_w$ wherein w is 1–10, and $-R^{10}NR^{10}R^{10}$;
each $R^{10}$ is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
Y is N or CH;
$R^2$ is selected from the group consisting of halo, alkyl, alkenyl, cycloalkyl, cycloalkenyl, Ay, Het, $-OR^7$, $-OAy$, $-OHet$, $-OR^{10}Het$, $-S(O)_nR^9$, $-S(O)_nAy$, $-S(O)_nHet$, $-S(O)_nNR^7R^8$, $-NR^7R^8$, $-NHHet$, $-NHR^{10}Ay$, $-NHR^{10}Het$, $-R^{10}NR^7R^8$ and $-R^{10}NR^7Ay$;
n is 0, 1 or 2;
$R^3$ and $R^4$ are the same or different and are each independently selected from the group consisting of H, halo, alkyl, alkenyl, cycloalkyl, Ay, Het, —OR⁷, —OAy, —C(O)R⁷, C(O)Ay, —CO₂R⁷, —CO₂Ay, —SO₂NHR⁹, —NR⁷R⁸, —NR⁷Ay, —NHHet, —NHR¹⁰Het, —R¹⁰cycloalkyl, —R¹⁰OR⁷, —R¹⁰OAy, —R¹⁰NR⁷R⁸ and —R¹⁰NR⁷Ay;

Ring A is a 5–10 membered heterocyclic or heteroaryl group;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)ₙR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; and Z- is a counter ion.

Generally, a compound of formula (I) may be prepared by a process comprising the steps of:

(a) reacting a compound of formula (XXV) with an alkyne of formula (XXVI) followed by desilylation to give a compound of formula (XXVII);

(b) reacting the compound of formula (XXVII) with a compound of formula (XXVIII) to prepare a compound of formula (XXIX);

(c) reacting the compound of formula (XXIX) with a 1-aminopyridinium salt of formula (XXX) to prepare a compound of formula (I).

The order of the foregoing steps is not critical to the process and as such these steps may be carreid out in any suitable order according to the skill in the art. More specifically, a compound of formula (I) can be prepared by reacting a compound of formula (XXIX) with a 1-aminopyridinium salt of formula (XXX) to prepare a compound of formula (I).

wherein all variables are as defined above in connection with Scheme 5.

Cycloaddition reactions such as these are commonly known as [3+2] dipolar cycloaddition reactions. Conveniently the reaction may be carried out by mixing the reactants (i.e., compounds of formula (XXVII) and (XXVIII)), in equimolar amounts, in an inert solvent and adding a suitable base. The mixture is then stirred at between 20–100° C. until the reaction is judged complete by the disappearance of one of the reactants. Suitable solvents include but are not limited to acetonitrile, dioxane, tetrahydrofuran, dimethylformamide and the like. Suitable bases include non-nucleophilic amines such as 1,8-diazabicyclo[5.4.0]undec-7-ene, 1,5-diazabicyclo[4.3.0]non-5-ene, 1,4-diazabicyclo[2.2.2]octane and the like. Compounds of formula (XXX) are aminated pyridine derivatives and are either commercially available or can be conveniently prepared by reacting a suitable pyridine with an aminating reagent such as O-(mesitylsulfonyl)hydroxylamine, O-(diphenylphosphinyl)hydroxylamine, hydroxylamine-O-sulfonic acid and the like.

Alkynyl compounds of formula (XXIX) are either known compounds or can be prepared by methods described in the literature or known to those skilled in the art of organic synthesis.

In addition to the foregoing process for preparing certain compounds of formula (I), the present invention also provides certain intermediate compounds for use in the preparation of such compounds of formula (I) according to the foregoing process. Such intermediates are described in Scheme 5 above.

In a further embodiment, a compound of formula (I) may be conveniently prepared by a process outlined in Scheme 6 below

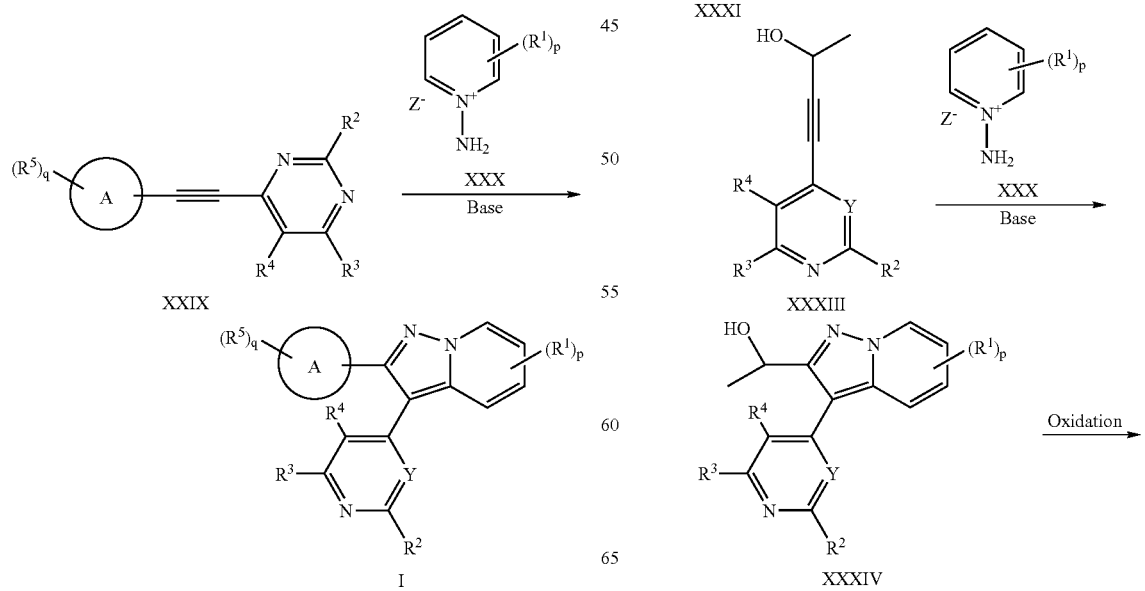

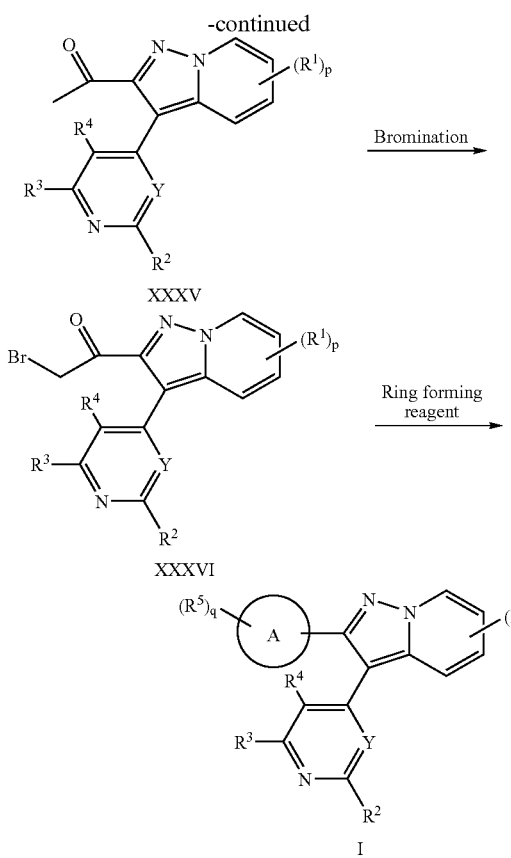

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, $-OR^7$, $-OAy$, $-OR^{10}Ay$, $-OHet$, $-OR^{10}Het$, $-C(O)R^9$, $-C(O)Ay$, $-C(O)Het$, $-CO_2R^9$, $-C(O)NR^7R^8$, $-C(O)NR^7Ay$, $-C(O)NHR^{10}Ay$, $-C(O)NHR^{10}Het$, $-C(S)NR^9R^{11}$, $-C(NH)NR^7R^8$, $-C(NH)NR^7Ay$, $-S(O)_nR^9$, $-S(O)_nAy$, $-S(O)_nHet$, $-S(O)_2NR^7R^8$, $-S(O)_2NR^7Ay$, $-NR^7R^8$, $-NR^7Ay$, $-NHHet$, $-NHR^{10}Ay$, $-NHR^{10}Het$, $-R^{10}$cycloalkyl, $-R^{10}Ay$, $-R^{10}Het$, $-R^{10}O-C(O)R^9$, $-R^{10}O-C(O)Ay$, $-R^{10}O-C(O)Het$, $-R^{10}O-S(O)_nR^9$, $-R^{10}OR^9$, $-R^{10}C(O)R^9$, $-R^{10}CO_2R^9$, $-R^{10}C(O)NR^9R^{11}$, $-R^{10}C(O)NR^7Ay$, $-R^{10}C(O)NHR^{10}Het$, $-R^{10}C(S)NR^9R^{11}$, $-R^{10}C(NH)NR^9R^{11}$, $-R^{10}SO_2R^9$, $-R^{10}SO_2NR^9R^{11}$, $-R^{10}SO_2NHCOR^9$, $-R^{10}NR^7R^8$, $-R^{10}NR^7Ay$, $-R^{10}NHC(NH)NR^9R^{11}$, cyano, nitro and azido;

or two adjacent $R^1$ groups together with the carbon atoms to which they are bonded form a cycloalkyl or a 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, $-C(O)R^9$, $-CO_2R^9$, $-C(O)NR^9R^{11}$, $-C(S)NR^9R^{11}$, $-C(NH)NR^9R^{11}$, $-SO_2R^{10}$, $-SO_2NR^9R^{11}$, $-R^{10}$cycloalkyl, $-R^{10}OR^9$, $-R^{10}C(O)R^9$, $-R^{10}CO_2R^9$, $-R^{10}C(O)NR^9R^{11}$, $-R^{10}C(S)NR^9R^{11}$, $-R^{10}C(NH)NR^9R^{11}$, $-R^{10}SO_2R^{10}$, $-R^{10}SO_2NR^9R^{11}$, $-R^{10}SO_2NHCOR^9$, $-R^{10}NR^9R^{11}$, $-R^{10}NHCOR^9$, $-R^{10}NHSO_2R^9$ and $-R^{10}NHC(NH)NR^9R^{11}$;

each $R^9$ and $R^{11}$ are the same or different and are independently selected from the group consisting of H, alkyl, cycloalkyl, $-R^{10}$cycloalkyl, $-R^{10}OH$, $-R_{10}(OR^{10})_w$ wherein w is 1–10, and $-R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

Y is N or CH;

$R^2$ is selected from the group consisting of halo, alkyl, alkenyl, cycloalkyl, cycloalkenyl, Ay, Het, $-OR^7$, $-OAy$, $-OHet$, $-OR^{10}Het$, $-S(O)_nR^9$, $-S(O)_nAy$, $-S(O)_nHet$, $-S(O)_nNR^7R^8$, $-NR^7R^8$, $-NHHet$, $-NHR^{10}Ay$, $-NHR^{10}Het$, $-R^{10}NR^7R^8$ and $-R^{10}NR^7Ay$;

n is 0, 1 or 2;

$R^3$ and $R^4$ are the same or different and are each independently selected from the group consisting of H, halo, alkyl, alkenyl, cycloalkyl, Ay, Het, $-OR^7$, $-OAy$, $-C(O)R^7$, $C(O)Ay$, $-CO_2R^7$, $-CO_2Ay$, $-SO_2NHR^9$, $-NR^7R^8$, $-NR^7Ay$, $-NHHet$, $-NHR^{10}Het$, $-R^{10}$cycloalkyl, $-R^{10}OR^7$, $-R^{10}OAy$, $-R^{10}NR^7R^8$ and $-R^{10}NR^7Ay$;

Ring A is a 5–10 membered heterocyclic or heteroaryl group;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, $-OR^7$, $-OAy$, $-OR^{10}Ay$, $-OHet$, $-OR^{10}Het$, $-C(O)R^9$, $-C(O)Ay$, $-C(O)Het$, $-CO_2R^9$, $-C(O)NR^7R^8$, $-C(O)NR^7Ay$, $-C(O)NHR^{10}Het$, $-C(S)NR^9R^{11}$, $-C(NH)NR^7R^8$ $-C(NH)NR^7Ay$, $-S(O)_nR^9$, $-S(O)_2NR^7R^8$, $-S(O)_2NR^7Ay$, $-NR^7R^8$, $-NR^7Ay$, $-NHHet$, $-NHR^{10}Ay$, $-NHR^{10}Het$, $-R^{10}$cycloalkyl, $-R^{10}Het$, $-R^{10}OR^9$, $-R^{10}C(O)R^9$, $-R^{10}CO_2R^9$, $-R^{10}C(O)NR^9R^{11}$, $-R^{10}C(O)NR^7Ay$, $-R^{10}C(O)NHR^{10}Het$, $-R^{10}C(S)NR^9R^{11}$, $-R^{10}C(NH)NR^9R^{11}$, $-R^{10}SO_2R^9$, $-R^{10}SO_2NR^9R^{11}$, $-R^{10}SO_2NHCOR^9$, $-R^{10}NR^7R^8$, $-R^{10}NR^7Ay$, $-R^{10}NHC(NH)NR^9R^{11}$, cyano, nitro and azido; and Z- is a counter ion.

Generally, a compound of formula (I) can be prepared by a process comprising the steps of:

(a) reacting a compound of formula (XXXI) with an alkyne of formula (XXXII) to prepare a compound of formula (XXXIII);

(b) reacting the compound of formula (XXXIII) with a 1-aminopyridinium salt of formula (XXX) to prepare a compound of formula (XXXIV);

(c) oxidizing the compound of formula (XXXIV) to prepare a compound of formula (XXXV);

(d) brominating the compound of formula (XXXV) to prepare a compound of formula (XXXVI); and (e) treating the compound of formula (XXXVI) with a ring forming reagent to prepare a compound of formula (I).

More specifically, a compound of formula (I) can be prepared by reacting a compound of formula (XXXVI) with a suitable ring forming reagent

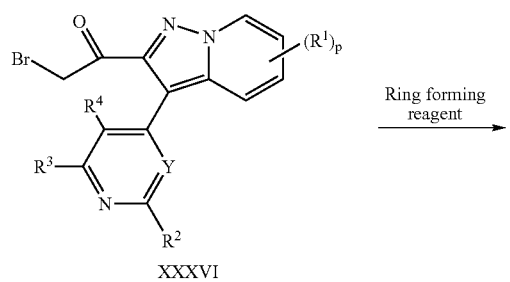

XXXVI

Ring forming reagent →

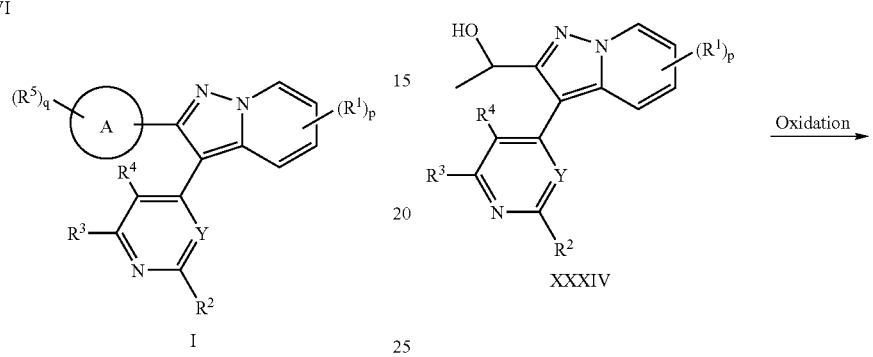

I wherein all variables are as defined in connection with Scheme 6.

Reactions of a alpha-halocarbonyl component with a ring forming reagent are well known to those skilled in the art of heterocyclic synthesis (Heterocyclic Chemistry 4$^{th}$ Ed., J. A. Joule and K. Mills, Blackwell Science 2000 etc.). Examples of such reactions include, but are not limited to, reaction of the alpha-halocarbonyl component with thioformamide or higher thioamides to give thiazoles, amidines to give imidazoles, amides to give oxazoles, etc. Examples of suitable ring forming agents include but are not limited to thiourea, acetamide and benzamidine.

A compound of formula (XXXVI) can be preared by bromination of a compound of formula (XXXV).

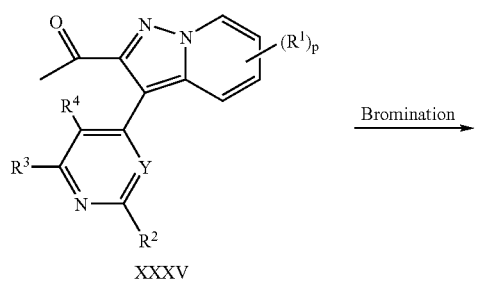

XXXV

Bromination →

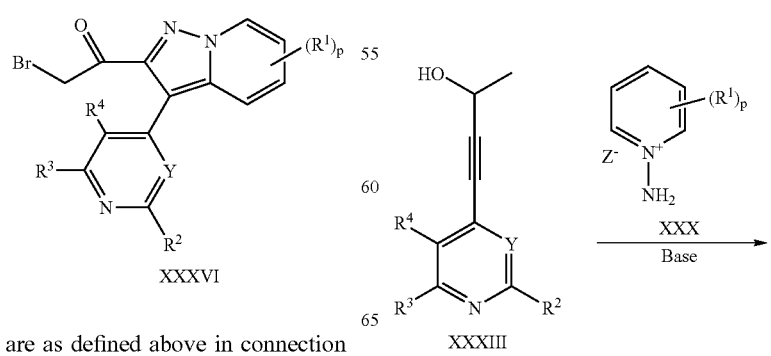

XXXVI wherein all variables are as defined above in connection with Scheme 6.

Bromination can be carried out using any of several bromination methods known to those skilled in the art of organic synthesis. Treatment of compound of formula (XXXV) with bromine in acetic acid is an example of one particular bromination method.

A compound of formula (XXXV) can be prepared by oxidation of a compound of formula (XXXIV).

XXXIV

Oxidation →

XXXV wherein all variables are as defined above in connection with Scheme 6.

Suitable oxidizing agents include but are not limited to, manganese dioxide, and the like, in an inert solvent Suitable inert solvents include but are not limited to, dichloromethane, chloroform, N,N-dimethylformamide, ether, and the like.

A compound of formula (XXXIV) can be prepared by reacting a compound of formula (XXXIII) with a 1-aminopyridinium salt of formula (XXX).

XXXIII

XXX

Base →

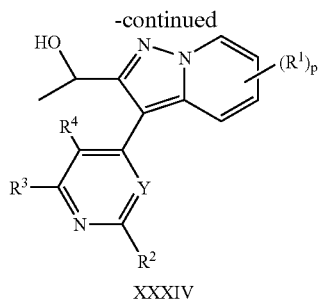

XXXIV wherein all variables are as defined above in connection with Scheme 6.

Cycloaddition reactions such as these are commonly known as [3+2] dipolar cycloaddition reactions. Conveniently the reaction may be carried out by mixing the reactants (XXXIII) and (XXX), in equimolar amounts, in an inert solvent and adding a suitable base. The mixture is then stirred at between 20–100° C. until the reaction is judged complete by the disappearance of one of the reactants. Suitable solvents include but are not limited to acetonitrile, dioxane, tetrahydrofuran, dimethylformamide and the like. Suitable bases include non-nucleophilic amines such as 1,8-diazabicyclo[5.4.0]undec-7-ene, 1,5-diazabicyclo[4.3.0]non-5-ene, 1,4 diazabicyclo[2.2.2]octane and the like.

Acetylenic compounds of formula (XXXIII) are either known compounds or can be prepared by methods described in the literature or are known to those skilled in the art of organic synthesis.

In addition to the foregoing process for preparing certain compounds of formula (I), the present invention also provides certain intermediate compounds for use in the preparation of such compounds of formula (I) according to the foregoing process. Such intermediates are described in Scheme 6 above.

Any of the processes described above may optionally comprise the further step of converting a compound of formula (I) into a pharmaceutically acceptable salt, solvate or physiologically functional derivative thereof. Processes for such conversion are well known in the art.

As will be apparent to those skilled in the art, the compounds of formula (I) may be converted to other compounds of formula (I) using techniques well known in the art For example, one method of converting a compound of formula (I) to another compound of formula (I) comprises a) oxidizing the compound of formula (I-A) to prepare a compound of formula (I-B) and then b) optionally reacting a compound of formula (I-B) with an oxygen or amine nucleophile of formula $R^2$, wherein $R^2$ is —$NR^7R^8$, —$OR^7$, Het attached through N, —NHHet, $NHR^{10}$Het, OHet and —$OR^{10}$Het to produce a compound of formula (I) wherein $R^2$ is —$NR^7R^8$, —$OR^7$, Het attached through N, —NHHet, $NHR^{10}$Het, OHet and —$OR^{10}$Het

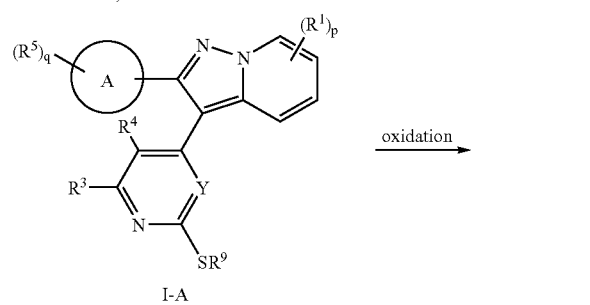

I-A

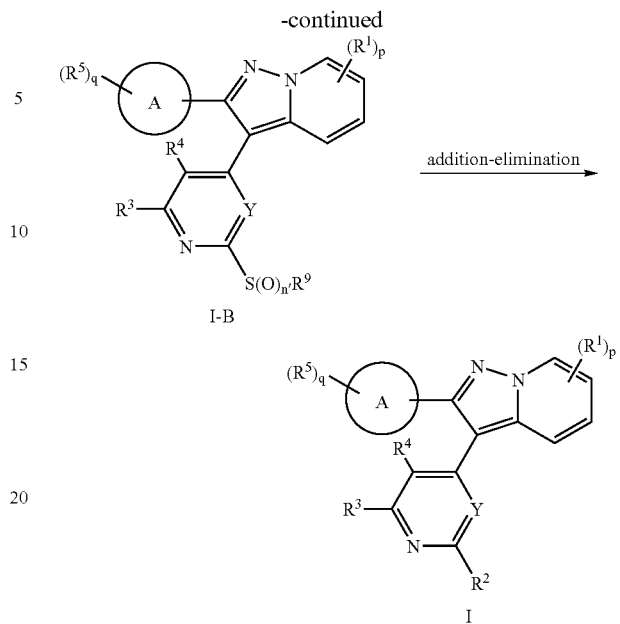

wherein n' is 1 or 2;

$R^2$ is selected from the group consisting of —$NR^7R^8$, —$OR^7$, Het linked through N, —NHHet, —$NHR^{10}$Het, —OHet, and —$OR^{10}$Het; and all other variables are as defined according to any process described above.

More specifically, a compound of formula (I) wherein $R^2$ is selected from the group consisting of —$NR^7R^8$, —$OR^7$, Het linked through N, —NHHet, —$NHR^{10}$Het, —OHet, and —$OR^{10}$Het, can be prepared by reacting a compound of formula (I-B) (i.e., a compound of formula (I) wherein $R^2$ is —$S(O)_{n'}$—$R^9$ where n' is 1 or 2) with an oxygen or amine nucleophile of formula $R^2$, wherein $R^2$ is —$NR^7R^8$, —$OR^7$, Het linked through N, —NHHet, —$NHR^{10}$Het, —OHet, and —$OR^{10}$Het. The reaction may be carried out neat or in a suitable solvent and may be heated to 50–150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine.

A compound of formula (I-B) may be conveniently prepared by reacting a compound of formula (I-A) (i.e., a compound of formula (I) wherein $R^2$ is —$S(O)_{n'}R^9$ where n is 0) with an oxidizing agent in an inert solvent, optionally in the presence of a base. Typically the oxidizing agent is a peracid such as 3-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like. If the compound of formula (I-A) contains oxidizeable nitrogens, it may be preferred to perform the oxidation under acidic conditions. Acetic acid and the like can be added to make the solution acidic.

A compound of formula (I-A) can be prepared by methods described above wherein $R^2$=$SR^9$ from the reaction of a compound selected from the group consisting of a compound of formula (XVI), a compound of formula (IX) and a compound of formula (XX) with a compound of formula (X-A) (i.e., the compound of formula (X) wherein $R^2$ is —$SR^9$). The requisite compound of formula (X-A) can be obtained from commercial sources or prepared by methods known to one skilled in the art.

Another particularly useful method for converting a compound of formula (I) to another compound of formula (I) comprises reacting a compound of formula (I-C) (i.e., a compound of formula (I) wherein $R^2$ is fluoro) with an amine nucleophile (including unsubstituted and substituted amines, heterocycles and heteroaryls, particularly those bound through N), and optionally heating the mixture to 50–150° C. to prepare a compound of formula (I-D) (i.e., a compound of formula (I) wherein $R^2$ is selected from the group consisting of Het, —$NR^7R^8$, —NHHet, —$NHR^{10}Ay$ and —$NHR^{10}Het$).

As a further example, a compound of formula (I-E) may be converted to a compound of formula (I-F) using either of two methods.

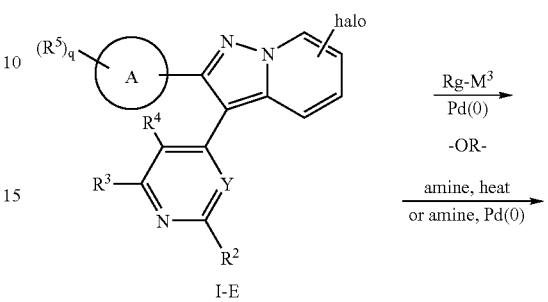

I-E

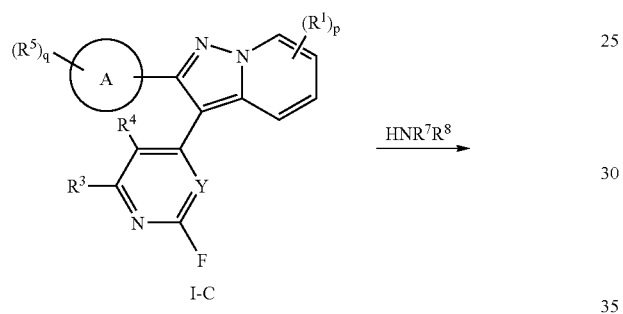

I-C

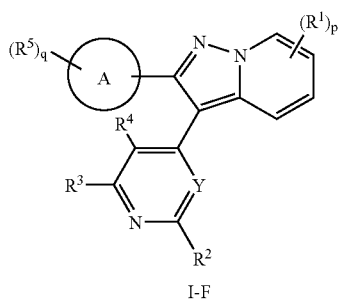

I-F

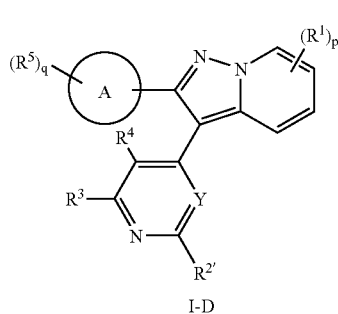

I-D wherein $R^{2'''}$ is selected from the group consisting of Het, —$NR^7R^8$, —NHHet, —$NHR^{10}Ay$ and —$NHR^{10}Het$, and all other variables are as defined in any process described above.

This procedure may be carried out by mixing a compound of formula (I-C) in a neat amine, or in a suitable solvent with an excess of an amine to produce a compound of formula (I-D). Typically the solvent is a lower alcohol such as methanol, ethanol, isopropanol and the like. Other suitable solvents may include N,N-dimethylformamide, 1-methyl-2-pyrrolidine and the like.

wherein $M^3$ is $B(OH)_2$, $B(ORa)_2$, $B(Ra)_2$, $Sn(Ra)_3$, Zn-halide; Zn—Ra or Mg-halide, Rg is Ay or Het, and all other variables are as defined in any process described above.

Such method can be carried out using the reaction and conditions described above in connection with Scheme 1 for the conversion of a compound of formula (VII-A) to a compound of formula (VII). Thus, the present invention provides a process for converting a compound of formula (I-E) to a compound of formula (I-F) which comprises either: (1) replacing a halogen of the compound of formula (I-E) with an amine; or (2) coupling the compound of formula (I-E) with a metal compound of the formula Rg—$M^3$ where $M^3$ is $B(OH)_2$, $B(ORa)_2$, $B(Ra)_2$, $Sn(Ra)_3$, Zn-halide; Zn—Ra or Mg-halide.

As a further example, a compound of formula (I-G) (i.e., a compound of formula (I) wherein q is 1 or more and at least one $R^5$ is —O-methyl) may be converted to a compound of formula (I-H) (i.e., a compound of formula (I) wherein q is 1 or more and at least one $R^5$ is —OH) using conventional demethylation techniques. Additionally, a compound of formula (I-H) may optionally be converted to a compound of formula (I-J) (i.e., a compound of formula (I) wherein q is 1 or more and at least one $R^5$ is —$OR^{10}$). For example, the foregoing conversions are represented schematically as follows:

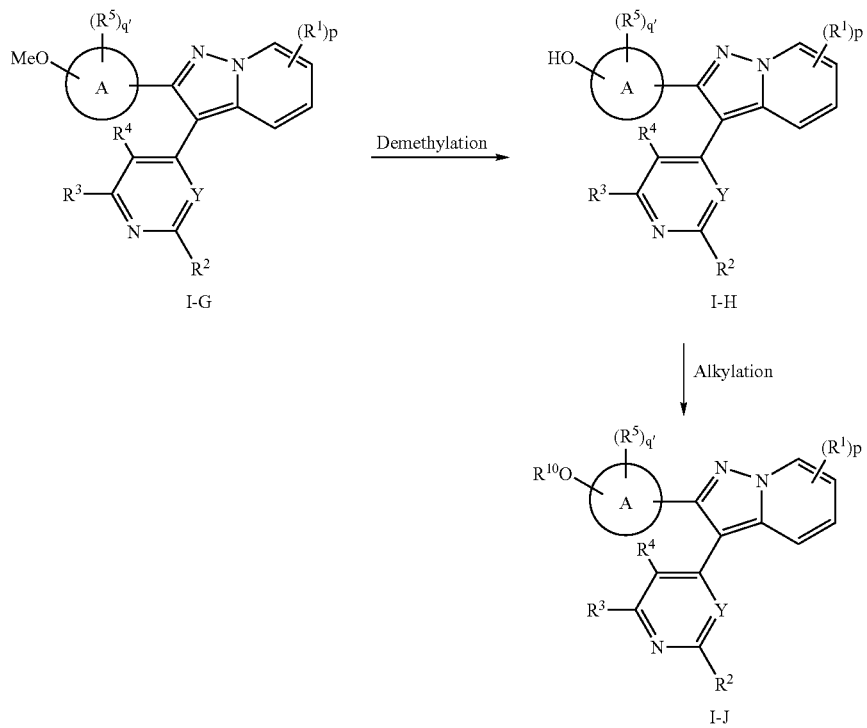

I-G

I-H

I-J wherein q' is 0–4; Me is methyl and all other variables are defined according to any process described above.

The demethylation reaction may be carried out by treating a compound of formula (I-G) in a suitable solvent with a Lewis acid at a temperature of −78° C. to room temperature, to produce a compound of formula (I-H). Typically the solvent is an inert solvent such as dichloromethane, chloroform, acetonitrile, toluene or the like. The Lewis acid may be boron tribromide, trimethylsilyl iodide or the like.

Optionally, a compound of formula (I-H) may be further converted to a compound of formula (I-J) by an alkylation reaction. The alkylation reaction may be carried out by treating a compound of formula (I-H) in suitable solvent with an alkyl halide of formula $R^{10}$-halo where $R^{10}$ is as defined above, to form another compound of formula (I-J). The reaction is preferably carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

The foregoing reaction method can also be used to convert a compound of formula (I) wherein at least one $R^1$ is —OMe to a compound of formula (I) wherein at least one $R^1$ is —$OR^{10}$. In another embodiment, the foregoing methods are employed to make the same conversion when $R^3$ or $R^4$ is —OMe, to prepare a compound of formula (I) wherein $R^3$ or $R^4$ is —OH or a compound of formula (I) wherein $R^3$ or $R^4$ is —$OR^{10}$.

As a further example of methods for converting a compound of formula (I) to another compound of formula (I), a compound of formula (I-K) (i.e., a compound of formula (I) wherein q is 1 or more and at least one R is halo) may be converted to a compound of formula (I-L) (i.e., a compound of formula (I) wherein q is 1 or more and at least one $R^5$ is Ay, Het or a nitrogen-linked substituent). For example, the conversion of a compound of formula (I-K) to a compound of formula (I-L) is shown schematically below.

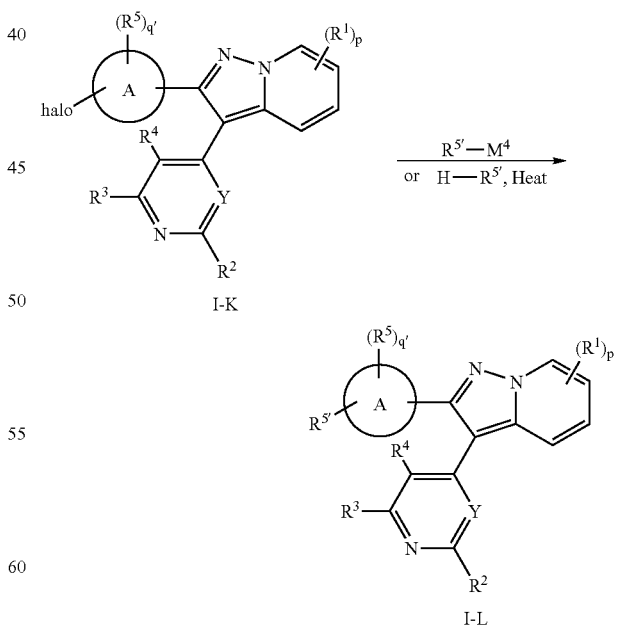

I-K

I-L wherein:
q' is 0–4;
$R^{5'}$ is selected from the group consisting of Ay, —$NHR^{10}$Ay, —$NR^7$Ay, Het, —NHHet, —$NHR^{10}$Het, and —$NR^7R^8$;

$M^4$ is selected from the group consisting of —B(OH)$_2$, —B(ORa)$_2$, —B(Ra)$_2$, and —Sn(Ra)$_2$ wherein Ra is alkyl or cycloalkyl; and all other variables are as defined according to any process described above.

The conversion of compounds of formula (I-K) to compounds of formula (I-L) is carried out by heating with a compound of formula H-R$^{5'}$ or coupling the compound of formula (I-K) with a compound of formula R$^{5'}$—M$^4$, where M$^4$ is —B(OH)$_2$, —B(ORa)$_2$, —B(Ra)$_2$, —Sn(Ra)$_2$ wherein Ra is alkyl or cycloalkyl. The reaction may be carried out in an inert solvent, in the presence of a palladium (0) source. The reaction may optionally be heated to 50–150° C. Preferably the reaction is performed by reacting equimolar amounts of a compound of formula (I-K) with a compound of formula R$^{5'}$—M$^4$. The reaction may also be performed in the presence of an excess R$^{5'}$—M$^4$. The palladium (0) catalyst is preferably present in 1–25 mol % compared to the compound of formula (I-K). Examples of suitable palladium catalysts include but are not limited to, tetrakis(triphenylphosphine)palladium (0), dichlorobis(triphenylphosphine)-palladium(II), and bis(diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the compound of formula R$^{5'}$—M$^4$ is a boronic acid or ester or a borinate the reaction is more conveniently carried out by adding a base in a proportion equivalent to, or greater than, that of the compound of formula R$^{5'}$—M$^4$. A compound of formula R$^{5'}$—M$^4$ may be obtained from commercial sources or prepared either as discreet isolated compound or generated in situ using methods known to one skilled in the art. (Suzuki, A. *J. Organomet. Chem.* 1999, 576, 147; Stille, J. *Angew. Chem. Int. Ed. Engl* 1986, 25, 508; Snieckus, V. *J. Org. Chem.* 1995, 60, 292.)

In yet another example, a compound of formula (I-K) (i.e., a compound of formula (I) wherein q is 1 or more and at least one R$^5$ is halo) is converted to a compound of formula (I-N) (i.e., a compound of formula (I) wherein q is 1 or more and at least one R$^5$ is —NH$_2$). Optionally, a compound of formula (I-N) may then be converted to a compound of formula (I-O) (i.e., a compound of formula (I) wherein q is 1 or more and at least one R$^5$ is —NR$^7$R$^8$ where R$^7$ and R$^8$ are not both H). For example, the foregoing conversions are represented schematically as follows:

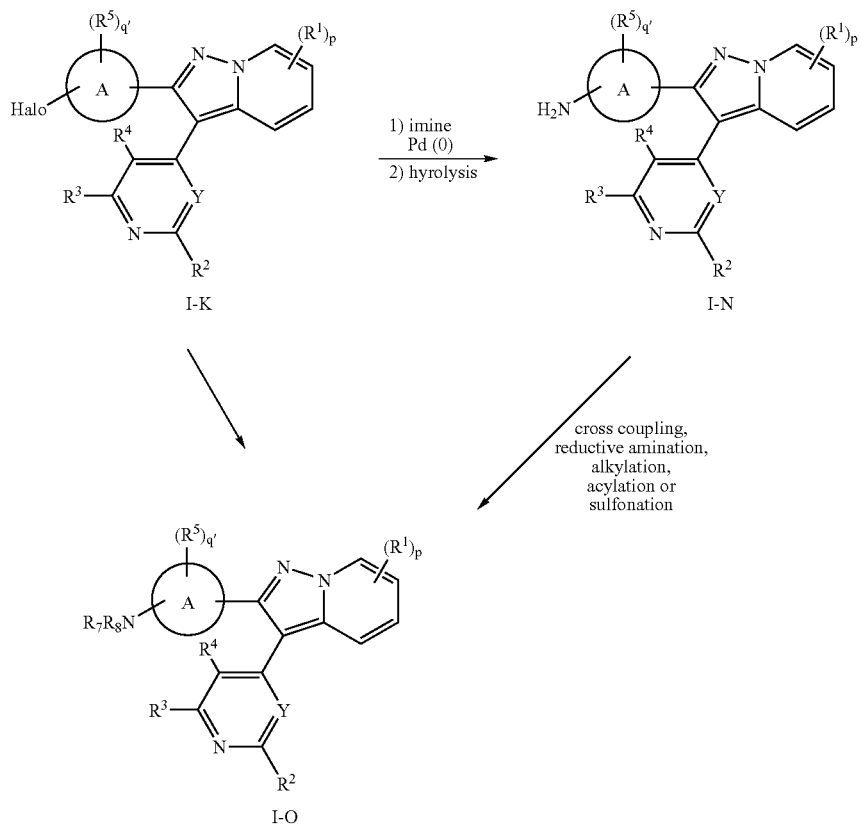

wherein q' is 0–4, and all other variables are defined according to any process described above.

The process of converting a compound of formula (I-K) to a compound of formula (I-N) is carried out by reacting a compound of formula (I-K) with an imine in the presence of a palladium (0) source, a base and a suitable ligand, followed by hydrolysis to give a compound of formula (I-N). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

Reaction of a compound of formula (I-N) with compound of formula R$^7$-halogen in a suitable solvent in the presence of base, optionally with heating may be used to prepare compounds of formula (I-O). Typically the base is triethylamine or pyridine and the solvent is N,N-dimethylformamide and the like. Other transformations well known to those skilled in the art for use with anilines may be used to convert a compound of formula (I-N) to a compound of formula (I-O).

Additional compounds of formula (I-O) can be obtained by reductive amination of compounds of formula (I-N) with ketones or aldehydes. See, A. Abdel-Magid, et al., *J. Org. Chem.* 61:3849–3862 (1996). Typically a compound of formula (I-N) is treated with an aldehyde or a ketone in the presence of an acid, such as acetic acid, and a reducing agent, such as sodium triacetoxyborohydride and the like, in an inert solvent such as dichloroethane and the like.

The foregoing reaction methods can also be used to convert a compound of formula (I) wherein at least one $R^1$ is halo to a compound of formula (I) wherein at least one $R^1$ is $-NH_2$. In another embodiment, the foregoing methods are employed to make the same conversion when $R^3$ or $R^4$ is halo, to prepare a compound of formula (I) wherein $R^3$ or $R^4$ is $-NH_2$ or a compound of formula (I) wherein $R^3$ or $R^4$ is $-NR^7R^8$ (where $R^7$ and $R^8$ are not both H).

As previously described, another method for converting a compound of formula (I-K) directly to a compound of formula (I-O) involves heating a compound of formula (I-K) with a amine to thermally displace the halogen.

In the embodiment where a compound of formula (I) is defined where $R^1$ is not located at C-7, the compound of formula (I-P) may be converted to a compound of formula (I-Q). For example, a compound of formula (I-P) may be converted to a compound of formula (I-Q) by a deprotonation/electrophile quench protocol. For example, reaction of a compound of formula (I-P) with a base, such as n-butyllithium, followed by reacting with an electrophilic agent gives compounds of formula (I-Q).

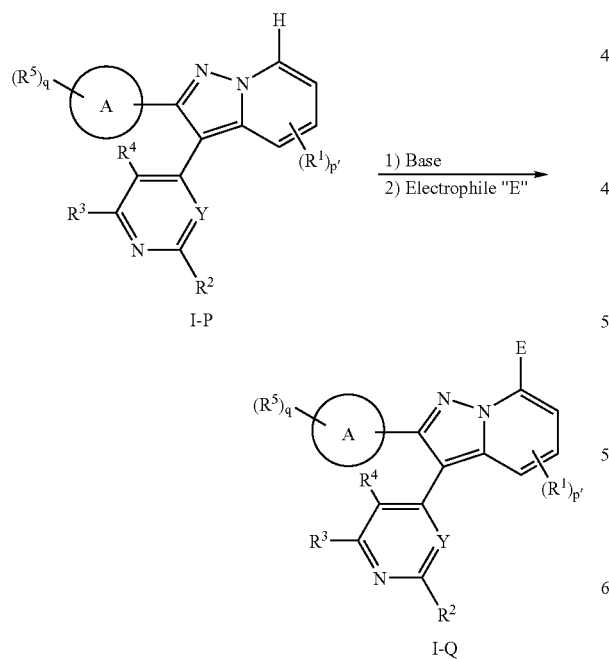

wherein p' is 0–2 and E is selected from halo, alkyl, $R^{10}$cycloalkyl, $-C(O)R^9$, $-C(O)Ay$, $-C(O)Het$, $-CO_2R^9$, $-C(O)NR^7R^8$, $-C(O)NR^7Ay$ and $-S(O)_n$ $R^9$, and all other variables are as defined in connection with any processes described above.

Electrophiles which may be used in this process include, but are not limited to: halogens (E=iodo, bromo, chloro), alkyl halides (E=methyl, benzyl etc.); aldehydes (E=CH (OH)$R^{10}$); dimethylformamide (E=CHO); dialkyl disulfide (E=SMe, SEt, S-isopropyl etc); carbon dioxide (E=$CO_2$H); dimethylcarbamoyl chloride (E=C(O)NMe2) and the like.

Typically a compound of formula (I-P) in an inert solvent such as tetrahydrofuran at −78° C. is treated with a normucleophilic base. This reaction is subsequently quenched by addition of an electrophile. Suitable normucleophilic bases include, but are not limited to, n-butyllithium, lithium diisopropylamide, lithium tetramethylpiperidide and the like.

Further, compounds of formula (I) wherein $R^1$ is not located at C-7, may be converted to other compounds of formula (I), by a deprotonation/electrophile quench/nucleophilic displacement protocol. For example, reaction of a compound of formula (I-P) with a base, such as n-butyllithium, followed by quenching with an electrophilic halogenating agent gives a compound of formula (I-Q) where E is halogen, as outlined in the previous scheme. Treatment of compound of formula (I -Q), where E is halogen with a nucleophile ($Z^1$) in a suitable solvent optionally with heating and optionally in the presence of a base gives a compound of formula (I-R).

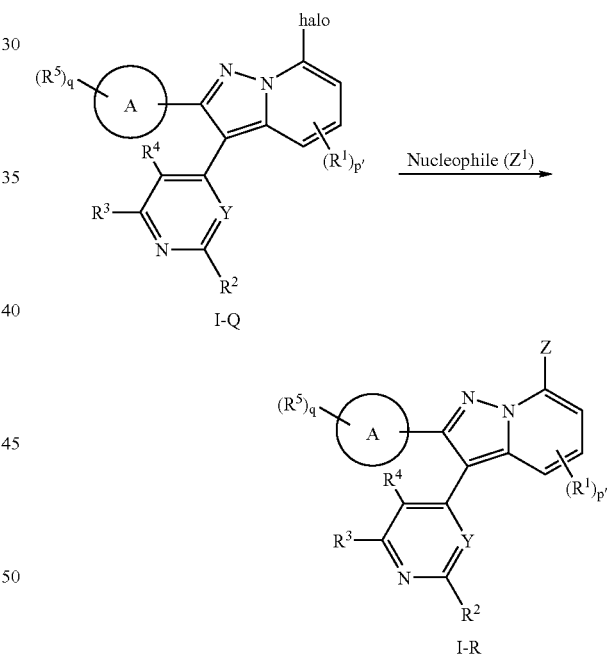

wherein p' is 0–3, $Z^1$ is selected from the group consisting of $-NHR^{10}Ay$, $-NR^7Ay$, Het, $-NHHet$, $-NHR^{10}Het$, $-OR^7$, $-OAy$, $-OR^{10}Ay$, $-OHet$, $-OR^{10}Het$, $-NR^7R^8$, $-S(O)_nR^9$(where n is 0), cyano and all other variables are as defined according to any process described above.

Solvents for use in this reaction include but are not limited to tetrahydrofuran, diethylether, and 1-methyl-2-pyrrolidinone. The base may be sodium hydride, sodium-tert-butoxide, potassium carbonate or the like.

As another example, one method of converting a compound of formula (I) to another compound of formula (I) comprises a) oxidizing the compound of formula (I-S), where $R^1$ is —$SR^{15}$ and $R^{15}$ is alkyl, cycloalkyl or Ay and is located at C-7, to prepare a compound of formula (I-T) and then b) optionally reacting a compound of formula (I-T) with a nucleophile $Z^1$ selected from the group consisting of —$NHR^{10}Ay$, —$NR^7Ay$, Het, —NHHet, —$NHR^{10}Het$, —$OR^7$, —OAy, —$OR^{10}Ay$, —OHet, —$OR^{10}Het$, —$NR^7R^8$, —$S(O)_nR^9$ (where n is 0) and cyano, to prepare a compound of formula (I-U).

of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compoudns of formula (I) to the target protein. More specifically, suitable assay methods will include com-

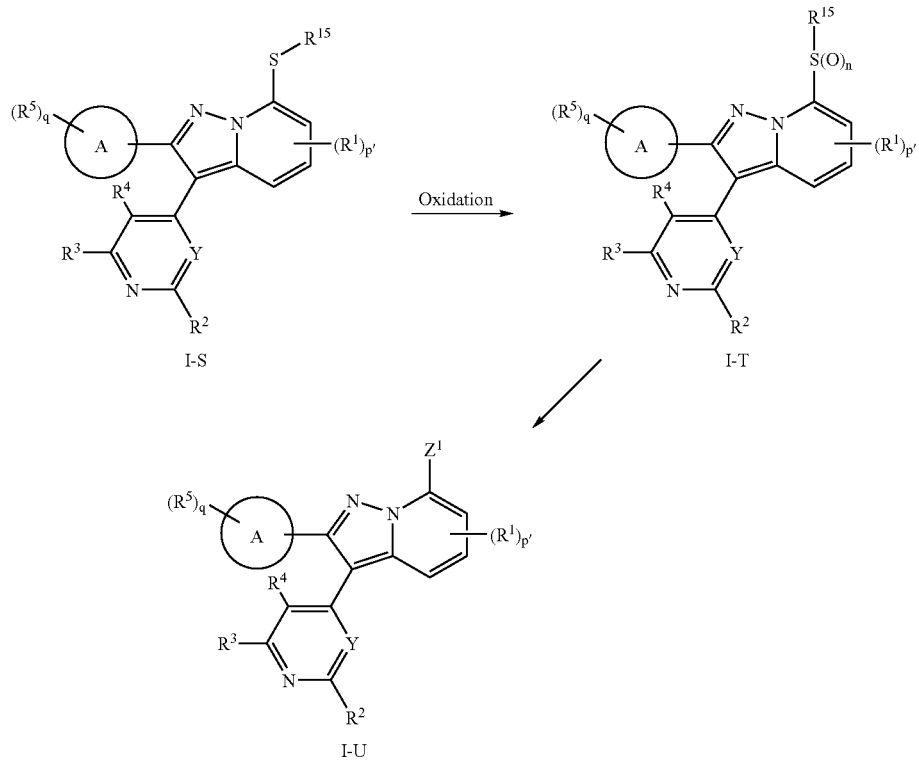

wherein p' is 0–3; $Z^1$ is selected from the group consisting of —$NHR^{10}Ay$, —$NR^7Ay$, Het, —NHHet, —$NHR^{10}Het$, —$OR^7$, —OAy, —$OR^{10}Ay$, —OHet, —$OR^{10}Het$, —$NR^7R^8$, —$S(O)_nR^9$ (where n is 0) and cyano; $R^{15}$ is alkyl, cycloalkyl or Ay; and all other variables are as defined according to any processes described above.

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). In one preferred embodiment, the compounds of formula (I) are tritiated.

The radiolabeled compounds of formula (I) and the biotinylated compounds of formula (I) are useful in assays for the identification of compounds for the treatment or prophylaxis petition binding assays. The radiolabeled compounds of formula (I) can be employed in assays according to the methods conventional in the art.

The following examples are illustrative embodiments of the invention, not limiting the scope of the invention in any way, the invention being defined by the claims which follow. Reagents are commercially available or are prepared according to procedures in the literature. Example numbers refer to those compounds listed in the tables above. $^1H$ and $^{13}C$ NMR spectra were obtained on Varian Unity Plus NMR spectrophotometers at 300 or 400 MHz, and 75 or 100 MHz respectively. $^{19}F$ NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated.

EXAMPLE 1

N-Cyclopentyl-3-[2-(cyclopentylamino)-4-pyrimidinyl]-2-(4-pyridinyl)pyrazolo[1,5-a]pyridin-7-amine

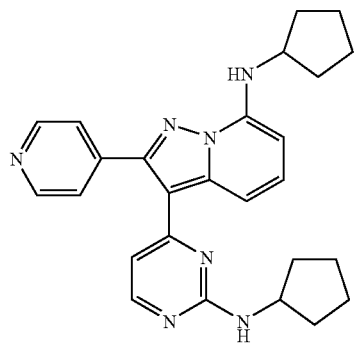

a) 2-(6-Chloro-2-pyridinyl)-1-(4-pyridinyl)ethanone oxime

To a cold (0 °C.) solution of 6-chloro-2-picoline (14.5 mL, 132.3 mmol) and ethyl isonicotinate (20.0 g, 132.3 mmol) in tetrahydrofuran (300 mL) was added lithium bis(trimethylsilyl)amide (280 mL 1.0 M in tetrahydrofuran, 278 mmol) dropwise via a pressure equalizing funnel over 1 hour. Upon complete addition, the cold bath was removed and the resulting solution was heated at 45° C. for 15 hours. The mixture was cooled to room temperature, methanol was added, and the solution was concentrated to give 2-(6-chloro-2-pyridinyl)-1-(4-pyridinyl)ethanone as a syrup, that was used without further purification. This syrup (11.7 g, 50 mmol) was dissolved in methanol (200 mL). To this solution was added hydroxylamine hydrochloride (17.5 g, 250 mmol) followed by the addition of a sodium hydroxide solution (10 g, 250 mmol in 30 mL of water). The resulting suspension was heated at reflux for 2 hours and then allowed to cool to room temperature. The mixture was concentrated and water was added to the resulting slurry. A white precipitate formed, which was collected by filtration, washed with water and dried to give 2-(6-chloro-2-pyridinyl)-1-(4-pyridinyl)ethanone oxime (10.5 g, 850%) as a white solid. $^1$H NMR (CDCl$_3$): δ 9.6 (broad s, 1H), 8.65 (d, 2H), 7.70 (d, 2H), 7.58 (t, 1H), 7.22 (m, 2H), 4.40 (s, 2H); MS m/248 (M+1).

b) 7-Chloro-2-(4-pyridinyl)pyrazolo[1,5-a]pyridine

To a solution of 2-(6-chloro-2-pyridinyl)-1-(4-pyridinyl) ethanone oxime (6.0 g, 24 mmol) in 1,2-dimethoxyethane (40 mL) at 0° C. was added trifluoroacetic anhydride (3.4 mL, 24 mmol), keeping the temperature below 10° C. during the addition. After the addition was complete, the reaction was warmed to room temperature. The solution was then cooled to 4° C. and a solution of triethylamine (6.7 mL, 48 mmol) in 1,2-dimethoxyethane (15 mL) was added over a period of 0.5 hours. The mixture was allowed to warm to room temperature and was stirred for 1.5 hours. To this mixture was added iron(II) chloride (50 mg) and the reaction was heated at 75° C. for 15 hours. The reaction mixture was poured into water (300 mL). The resulting suspension was extracted with ethyl acetate. The ethyl acetate phase was dried (magnesium sulfate), filtered and concentrated to a solid residue. This residue was purified by silica gel chromatography (1:1 ethyl acetate-hexane) to give 7-chloro-2-(4-pyridinyl)pyrazolo[1,5-a]pyridine (2.8 g, 500%) as a tan solid. $^1$H NMR (d$_6$-DMSO): δ 8.62 (m, 2H), 7.93 (m, 2H), 7.76 (dd, 1H), 7.42 (m, 2H), 7.24 (m, 1H); MS m/z 230 (M+1).

c) 1-[7-Chloro-2-(4-pyridinyl)pyrazolo[1,5-a]pyridin-3-yl]ethanone

To a solution of 7-chloro-2-(4-pyridinyl)pyrazolo[1,5-a] pyridine (2.0 g, 8.7 mmol) in acetonitrile (50 mL) at room temperature was added acetic anhydride (2.0 mL, 21 mmol). Boron trifluoride diethyletherate (5.3 mL, 42 mmol) was added dropwise and the resulting solution was heated at 80° C. for 12 hours. The reaction mixture was cooled to room temperature and quenched by the dropwise addition of saturated sodium bicarbonate. The reaction mixture was extracted with ethyl acetate, and the organic phase phase washed with brine, dried (magnesium sulfate), filtered and concentrated. The residue was purified by silica gel chromatography (5:95 methanol-dichloromethane) to give 1-[7-chloro-2-(4-pyridinyl)pyrazolo[1,5-a]pyridin-3-yl]ethanone (1.53 g, 65%) as a red foam. $^1$H NMR (CDCl$_3$): δ 8.82 (m, 2H), 8.45 (d, 1H), 7.62 (m, 2H), 7.54 (t, 1H), 7.25 (d, 1H), 2.26 (s, 3H); MS m/272 (M+1).

d) 1-[7-(Cyclopentylamino)-2-(4-pyridinyl)pyrazolo[1,5-a]pyridin-3-yl]ethanone To a solution of 1-[7-chloro-2-(4-pyridinyl)pyrazolo[1,5-a]pyridin-3-yl]ethanone (0.68 g, 2.5 mmol) in toluene (10 mL) was added successively rac-2,2'-bis(diphenylphosphino)-1,1'-binaphthyl (100 mg, 0.15 mmol), cesium carbonate (1.2 g, 3.8 mmol), cyclopentylamine (1.5 mL, 12.5 mmol), and palladium (II) acetate (25 mg, 0.1 mmol). The resulting mixture was stirred at 90° C. for 24 hours, at which time the reaction was judged complete by thin layer chromatography. The solution was cooled to room temperature and ethyl acetate and water were added to the reaction mixture. The phases were separated, and the aqueous phase again extracted with ethyl acetate. The combined organic phases were dried (magnesium sulfate), filtered and concentrated. The resulting residue was purified by flash chromatography (1:1 hexanes-ethyl acetate) to give 1-[7-(cyclopentylamino)-2-(4-pyridinyl)pyrazolo[1,5-a]pyridin-3-yl] ethanone (0.64 g, 80%) as a yellow foam. $^1$H NMR (CDCl$_3$): δ 8.80 (d, 2H), 7.65 (d, 1H), 7.60 (d, 2H), 7.50 (t, 1H), 6.20 (d, 1H), 6.06 (d, 1H), 4.0 (m, 1H), 2.26 (s, 3H), 1.6–2.2 (m, 8H); MS m/z 321 (M+1).

e) N-Cyclopentylguanidine hydrochloride

This compound was prepared by modification of a procedure from Bannard, R. A. B.; Casselman, A. A.; Cockburn, W. F.; and Brown, G. M. Can. J. Chem. 1958, 36, 1541–1549). To a solution of 2-methyl-2-thiopseudourea sulfate (13.9 g, 50.0 mmol) in water (40 mL) was added cyclopentylamine (14.8 mL, 150 mmol). The resultant mixture was heated to 55° C. for 20 minutes and then to reflux for 2.5 hours. The mixture was cooled to room temperature and concentrated in vacuo and azeotroped with methanol. Water was added (~100 mL) and Amberlite IRA 400 (Cl$^-$) resin was added. The mixture was stirred for 1 hour and then the resin was removed by filtration. The solution was On occasion the corresponding hydrochloride salts were formed to generate solids where noted.

concentrated in vacuo and azeotroped with methanol. The residue was recrystallized from methanol-acetone to yield N-cyclopentylguanidine hydrochloride (7.0 g, 86%) as a fine white solid. $^1$H NMR (D$_2$O): δ 3.62 (m, 1H), 1.75 (m, 2H), 1.52–1.32 (m, 6H); $^{13}$C NMR (D$_2$O) δ 156.23, 53.11, 32.15, 23.13; MS m/128 (M+1).

f) N-Cyclopentyl-3-[2-(cyclopentylamino)-4-pyrimidinyl]-2-(4-pyridinyl)pyrazolo[1,5-a]pyridin-7-amine A solution of 1-[7-(cyclopentylamino)-2-(4-pyridinyl)pyrazolo[1,5-a]pyridin-3-yl]ethanone (0.3 g, 0.94 mmol) in N,N-dimethylformamide dimethyl acetal (10 mL) was heated at reflux for 3 days. The mixture was allowed to cool to room temperature. Water was added and the resulting mixture was extracted with ethyl acetate. The ethyl acetate phase was dried (magnesium sulfate), filtered and concentrated. The resulting residue was purified by flash chromatography (7:3 ethyl acetate-acetone) to give 1-[7-(cyclopentylamino)-2-(4-pyridinyl)pyrazolo[1,5-a]pyridin-3-yl]-3-(dimethylamino)-2-propen-1-one (0.23 g, 65%) as a colored syrup which was used in the next step without further purification. To a solution of 1-[7-(cyclopentylamino)-2-(4-pyridinyl)pyrazolo[1,5-a]pyridin-3-yl]-3-(dimethylamino)-2-propen-1-one (0.10 g, 0.27 mmol) in tetrahydrofuran (10 mL) was added cyclopentyl guanidine hydrochloride (0.06 g, 0.38 mmol) followed by potassium tert-butoxide (0.085 g, 0.76 mmol). The resulting mixture was heated at reflux for 12 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (1:9 methanol-dichloromethane) to give the title compound (89 mg, 75%) as a white solid. $^1$H NMR (CDCl$_3$): δ 8.64 (d, 2H), 8.04 (d, 1H), 7.58 (m, 3H), 7.28 (t, 1H), 6.32 (d, 1H), 6.02 (d, 1H), 5.95 (d, 1H), 5.03 (d, 1H), 4.22 (m, 1H), 3.97 (m, 1H), 1.2–2.2 (m, 16H); MS m/z 440 (M+1).

EXAMPLE 2

N-Cyclopentyl-3-[2-(methylamino)-4-pyrimidinyl]-2-(4-pyridinyl)pyrazolo[1,5-a]pyridin-7-amine

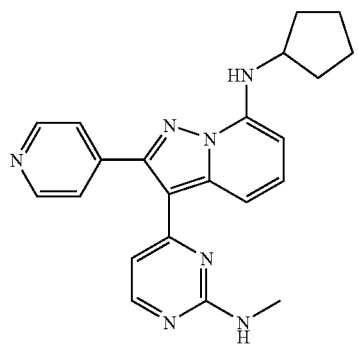

To a solution of 1-[7-(cyclopentylamino)-2-(4-pyridinyl)pyrazolo[1,5-a]pyridin-3-yl]-3-(dimethylamino)-2-propen-1-one (From example 1, 0.13 g, 0.35 mmol) in tetrahydrofuran (10 mL) was added cyclopentyl guanidine hydrochloride (0.06 g, 0.38 mmol) followed by potassium tert-butoxide (0.085 g, 0.76 mmol). The resulting mixture was heated at reflux for 12 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (1:20 methanol-ethyl acetate) to give the title compound (100 mg, 75%) as a yellow solid. $^1$H NMR (CDCl$_3$): δ 8.72 (d, 2H), 8.13 (d, 1H), 7.65 (m, 3H), 7.35 (t, 1H), 6.43 (d, 1H), 6.10 (d, 1H), 6.05 (d, 1H), 5.10 (m, 1H), 4.05 (m, 1H), 3.05 (d, 3H), 1.2–2.2 (m, 8H); MS m/z 386 (M+1).

EXAMPLE 3

N-cyclopentyl-3-[2-(cyclopentylamino)-4-pyrimidinyl]-2-(3-pyridinyl)pyrazolo[1,5-a]pyridin-7-amine

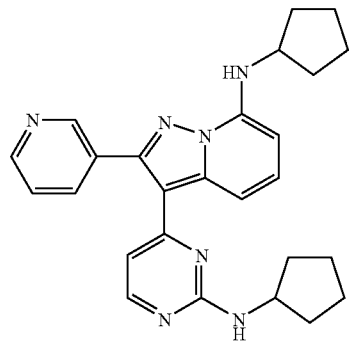

a) 2-(6-Chloro-2-pyridinyl)-1-(3-pyridinyl)ethanone oxime

In a similar manner as described in Example 1 from 6-chloro-2-picoline (9.3 g, 73 mmol) and methyl nicotinate (10.0 g, 73 mmol), 2-(6-chloro-2-pyridinyl)-1-(3-pyridinyl)ethanone was obtained as a syrup. This syrup (10 g, 70 mmol) was treated with hydroxylamine hydrochloride (24.3 g, 350 mmol) followed by the addition of a sodium hydroxide solution (14 g, 350 mmol in 30 mL of water) as described in example 1 to give 2-(6-chloro-2-pyridinyl)-1-(3-pyridinyl)ethanone oxime (14.4 g, 80%) as a white solid. $^1$H NMR (CDCl$_3$): δ 8.84 (d, 1H), 8.40 (dd, 1H), 8.00 (m, 1H), 7.50 (t, 1H), 7.2–7.4 (m, 3H), 4.26 (s, 2H); MS m/z 248 (M+1).

b) 7-Chloro-2-(3-pyridinyl)pyrazolo[1,5-a]pyridine

In a similar manner as described in Example 1 from 2-(6-chloro-2-pyridinyl)-1-(3-pyridinyl)ethanone oxime (9.6 g, 39 mmol) was obtained 7-chloro-2-(3-pyridinyl)pyrazolo[1,5-a]pyridine (2.8 g, 50%) as a tan solid. $^1$H NMR (CDCl$_3$): δ 9.20 (d, 1H), 8.64 (dd, 1H), 8.44 (dt, 1H), 7.56 (d, 1H), 7.48 (dd, 1H), 7.14 (dd, 1H), 7.0 (s, 1H), 6.96 (d, 1H); MS m/z 230 (M+1).

c) 1-[7-Chloro-2-(3-pyridinyl)pyrazolo[1,5-a]pyridin-3-yl]ethanone

In a similar manner as described in Example 1 from 7-chloro-2-(3-pyridinyl)pyrazolo[1,5-a]pyridine (1.5 g, 6.5 mmol) was obtained 1-[7-chloro-2-(3-pyridinyl)pyrazolo[1,5-a]pyridin-3-yl]ethanone (1.4 g, 60%) as a foam. $^1$H NMR (CDCl₃): δ 8.90 (broad s, 1H), 8.77 (d, 1H), 8.40 (d, 1H), 8.00 (dt, 1H), 7.50 (m, 2H), 7.20 (d, 1H), 2.21 (s, 3H); MS m/z 272 (M+1).

d) 1-[7-(Cyclopentylamino)-2-(3-pyridinyl)pyrazolo[1,5-a]pyridin-3-yl]ethanone In a similar manner as described in Example 1 from 1-[7-chloro-2-(3-pyridinyl)pyrazolo[1,5-a]pyridin-3-yl]ethanone (0.95 g, 3.5 mmol) was obtained 1-[7-(cyclopentylamino)-2-(3-pyridinyl)pyrazolo[1,5-a]pyridin-3-yl]ethanone (0.78 g, 70%) as a yellow foam. ¹H NMR (CDCl₃): δ 8.88 (s, 1H), 8.73 (m, 1H), 8.01 (d, 1H), 7.61 (d, 1H), 7.44 (m, 2H), 6.17 (d, 1H), 6.05 (d, 1H), 4.00 (m, 1H), 2.23 (s, 3H), 1.6–2.2 (m, 8H); MS m/z 321 (M+1).

e) N-Cyclopentyl-3-[2-(cyclopentyl methyl)-4-pyrimidinyl]-2-(3-pyridinyl)pyrazolo[1,5-a]pyridin-7-amine In a similar manner as described in Example 1 from 1-[7-(cyclopentylamino)-2-(4-pyridinyl)pyrazolo[1,5-a]pyridin-3-yl]ethanone (0.56 g, 1.8 mmol) was obtained N-cyclopentyl-3-[2-(cyclopentylmethyl)-4-pyrimidinyl]-2-(3-pyridinyl)pyrazolo[1,5-a]pyridin-7-amine (192 mg, 25% over 2 steps) as a white solid. ¹H NMR (CDCl₃): δ 8.90 (s, 1H), 8.63 (m, 1H), 8.05 (d, 1H), 7.95 (m, 1H), 7.65 (d, 1H), 7.3 (m, 2H), 6.30 (d, 1H), 6.0 (m, 1H), 5.35 (d, 1H), 4.25 (m, 2H), 3.98 (m, 1H), 1.5–2.2 (m, 16H); MS m/z 440 (M+1).

EXAMPLE 4

N-Cyclopentyl-N-(4-{2-[2-(cyclopentylamino)-4-pyrimidinyl]pyrazolo[1,5-a]pyridin-3-yl]-2-pyrimidinyl)amine

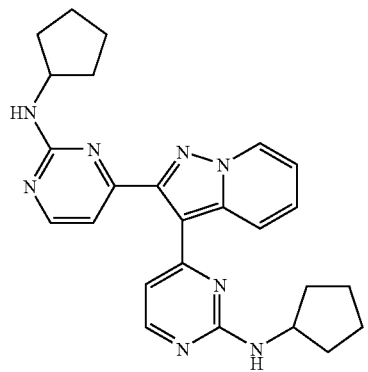

a) 4-Ethynyl-2-(methylsulfanyl)pyrimidine

4-Iodo-2-(methylsulfanyl)pyrimidine (2.0 g, 8.1 mmol) was dissolved in anhydrous tetrahydrofuran (50 mL). To this solution was added triethylamine (1.4 mL, 10.1 mmol), copper (I) iodide (80 mg, 0.4 mmol) and dichlorobis(triphenylphosphine) palladium (II) (140 mg, 0.24 mmol). (Trimethylsilyl)acetylene (1.4 mL, 10.1 mmol) was added dropwise to the resulting solution. After the addition of (trimethylsilyl)acetylene was complete the reaction was stirred at room temperature for 2 hours. Hexane was added to the reaction mixture and the mixture was filtered to remove precipitates. The solution was concentrated to give a syrup, that was purified by silica gel chromatography (1:1 ethyl acetate:hexane) to give 1.76 g (99%) of 2-(methylsulfanyl)-4-[(trimethylsilyl)ethynyl]pyrimidine. 2-(Methylsulfanyl)-4-[(trimethylsilyl)ethynyl]pyrimidine (1.76 g, 8.0 mmol) was dissolved in methanol (60 mL). To this solution was added potassium fluoride (467 mg, 8.0 mmol) and the resulting mixture stirred at room temperature for 5 minutes. The solution was concentrated and ethyl acetate and water were added. The phases were separated and the aqueous phase extracted with additional ethyl acetate. The organics were combined, dried over magnesium sulfate, filtered and concentrated to give 1.0 g (83%) of 4-ethynyl-2-(methylsulfanyl)pyrimidine as a white solid. ¹H NMR (CDCl₃): δ 8.51 (d, 1H), 7.06 (d, 1H), 3.34 (s, 1H), 2.56 (s, 3H); MS m/z 151 (M+1).

b) 2-(Methylsulfanyl)-4-{[2-(methylsulfanyl)-4-pyrimidinyl]ethynyl}pyrimidine 4-Iodo-2-(methylsulfanyl)pyrimidine (1.76 g, 7.1 mmol) was dissolved in anhydrous tetrahydrofuran (50 mL). To this solution was added triethylamine (1.2 mL, 8.5 mmol), copper (I) iodide (70 mg, 0.4 mmol) and dichlorobis(triphenylphosphine)palladium (II) (150 mg, 0.21 mmol). A solution of 4-ethynyl-2-(methylsulfanyl)pyrimidine (1.0 g, 7.1 mmol) in tetrahydrofuran was added dropwise. The reaction mixture was stirred at room temperature overnight Ethyl acetate and water were added to the reaction mixture. The phases were separated and the aqueous phase extracted with additional ethyl acetate. The organics were combined, dried over magnesium sulfate, filtered and concentrated. Purification by silica gel chromatography (1:1 ethyl acetate:hexane) gave 1.35 g (69%) of 2-(methylsulfanyl)-4-{[2-(methylsulfanyl)-4-pyrimidinyl]ethynyl}pyrimidine as a white solid. ¹H NMR (CDCl₃): δ 8.57 (d, 2H), 7.19 (d, 2H), 2.59 (s, 6H); MS m/z 275 (M+1).

c) 2,3-Bis[2-(methylsulfanyl)-4-pyrimidinyl]pyrazolo[1,5-a]pyridine 2-(Methylsulfanyl)-4-{[2-(methylsulfanyl)-4-pyrimidinyl]ethynyl}pyrimidine (0.1 g, 0.37 mmol) was dissolved in acetonitrile (5 mL). To this solution was added 1-aminopyridinium iodide (81 mg, 0.37 mmol) and 1,8-diazabicyclo[5.4.0]undec-7-ene (0.056 mL, 0.37 mmol) and the resulting mixture was stirred at room temperature overnight The resulting reddish suspension was concentrated in vacuo. Ethyl acetate and water were added to this residue. The phases were separated and the aqueous phase extracted with additional ethyl acetate. The organics were combined, dried over magnesium sulfate, filtered and concentrated. Purification by silica gel chromatography (1:1 ethyl acetate:hexane) gave 95 mg (71%) of 2,3-bis[2-(methylsulfanyl)-4-pyrimidinyl]pyrazolo[1,5-a]pyridine as a solid. ¹H NMR (CDCl₃): δ 8.64 (d, 1H), 8.53 (d, 1H), 8.41 (d, 1H), 8.31 (d, 1H), 7.56 (d, 1H), 7.37 (t, 1H), 7.13 (d, 1H), 7.00 (t, 1H), 2.59 (s, 3H), 2.37 (s, 3H); MS m/z 367 (M+1).

d) N-Cyclopentyl-N-(4-{2-[2-(cyclopentylamino)-4-pyrimidinyl]pyrazolo[1,5-a]pyridin-3-yl}-2-pyrimidinyl)amine 2,3-Bis[2-(methylsulfanyl)-4-pyrimidinyl]pyrazolo[1,5-a]pyridine (0.35 g, 0.96 mmol) was dissolved in dichloromethane (20 mL) and the resulting solution cooled to 0° C. in an ice bath. To this solution was added dropwise 3-chloroperoxybenzoic acid (824 mg, 57–86%) in dichloromethane. This reaction mixture was stirred at 0° C. for 10 minutes. Additional dichloromethane was added and the reaction mixture was extracted with saturated aqueous potassium carbonate. The organic phase was dried over magnesium sulfate, filtered and concentrated to give a foam. This foam was dissolved in cyclopentylamine and heated to 60° C. for 2 hours. The resulting mixture was concentrated to a solid that was recrystallized from acetonitrile to give 210 mg (50%) of N-cyclopentyl-N-(4-{2-[2-(cyclopentylamino)-4-pyrimidinyl]pyrazolo[1,5-a]pyridin-3-yl}-2-pyrimidinyl)amine as a solid. $^1$H NMR (CDCl$_3$): δ 8.52 (d, 1H), 8.34 (d, 1H), 8.27 (d, 1H), 8.14 (d, 1H), 7.29 (t, 1H), 6.90 (m, 2H), 6.62 (d, 1H), 5.23 (m, 2H), 4.30 (m, 1H), 4.20 (broad s, 1H), 1.8–2.1 (m, 4H), 1.4–1.8 (m, 12H); MS m/z 441 (M+1).

EXAMPLE 5

N-(4-{7-Chloro-2-[2-(cyclopentylamino)-4-pyrimidinyl]pyrazolo[1,5-a]pyridin-3-yl}-2-pyrimidinyl)-N-cyclopentylamine

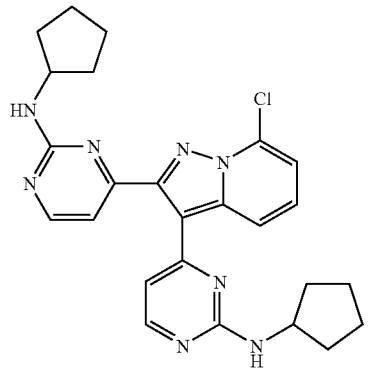

N-Cyclopentyl-N-(4-{2-[2-(cyclopentylamino)-4-pyrimidinyl]pyrazolo[1,5-a]pyridin-3-yl}-2-pyrimidinyl)amine (140 mg, 0.32 mmol) was dissolved in anhydrous tetrahydrofuran (5 mL). The resulting solution was cooled to –78° C., then n-butyllithium (0.99 mL, 1.6 mmol, 1.6 M in hexane) was added dropwise. The resulting dark solution was stirred at –78° C. for 20 minutes, then carbon tetrachloride (2 mL) was added. The reaction was stirred for additional 20 minutes and then quenched by the addition of water and allowed to warm to room temperature. The phases were separated and the aqueous phase extracted with ethyl acetate. The organics were combined, dried over magnesium sulfate, filtered and concentrated. Purification by silica gel chromatography (1:1 ethyl acetate:hexane) gave 80 mg (53%) of N-(4-{7-chloro-2-[2-(cyclopentylamino)-4-pyrimidinyl]pyrazolo[1,5-a]pyridin-3-yl}-2-pyrimidinyl)-N-cyclopentylamine as a foam. $^1$H NMR (CDCl$_3$): δ 8.37 (d, 1H), 8.27 (d, 1H), 8.16 (d, 1H), 7.26 (t, 1H), 7.06 (d, 1H), 7.04 (m, 1H), 6.62 (d, 1H), 5.21 (d, 1H), 5.15 (d, 1H), 4.32 (m, 1H), 4.10 (m, 1H), 1.4–2.1 (m, 16H); MS m/z 475 (M+1).

EXAMPLE 6

N-Cyclopentyl-2,3-bis[2-(cyclopentylamino)-4-pyrimidinyl]pyrazolo[1,5-a]pyridin-7-amine

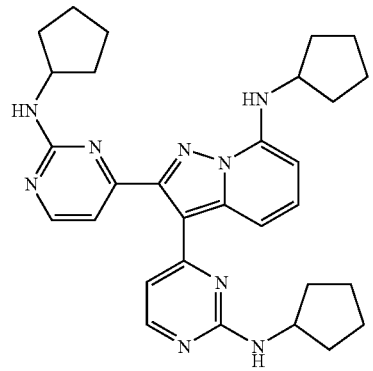

a) N-(4-{7-Chloro-2-[2-(cyclopentylamino)-4-pyrimidinyl]pyrazolo[1,5-a]pyridin-3-yl}-2-pyrimidinyl)-N-cyclopentylamine (60 mg, 0.13 mmol) was dissolved in cyclopentylamine (4 mL). To this solution was added successively rac-2,2'-bis(diphenylphosphino)-1,1'-binaphthyl (31 mg, 0.05 mmol), cesium carbonate (61 mg, 0.18 mmol) and palladium (II) acetate (6 mg, 0.03 mmol). The resulting mixture was stirred at 90° C. for 24 hours, at which time the reaction was judged complete by thin layer chromatography. The solution was cooled to room temperature and ethyl acetate and water were added to the reaction mixture. The phases were separated, and the aqueous phase again extracted with ethyl acetate. The combined organic phases were dried (magnesium sulfate), filtered and concentrated. The resulting residue was purified by flash chromatography (1:1 hexanes:ethyl acetate) to give 20 mg (30%) of N-cyclopentyl-2,3-bis[2-(cyclopentylamino)-4-pyrimidinyl]pyrazolo[1,5-a]pyridin-7-amine as a foam. $^1$H NMR (CDCl$_3$): δ 8.38 (d, 1H), 8.02 (broad s, 1H), 7.63 (d, 1H), 7.33 (t, 1H), 6.93 (s, 1H), 6.59 (d, 1H), 6.07 (d, 1H), 6.03 (m, 1H), 5.21 (m, 1H), 4.32 (m, 1H), 4.23 (m, 1H), 4.00 (m, 1H), 1.4–2.2 (m, 24H); MS m/z 524 (M+1).

EXAMPLE 7

N-(2-Methoxyethyl)-2,3-bis{2-[(2-methoxyethyl)amino]pyrimidin-4-yl}pyrazolo[1,5-a]pyridin-7-amine

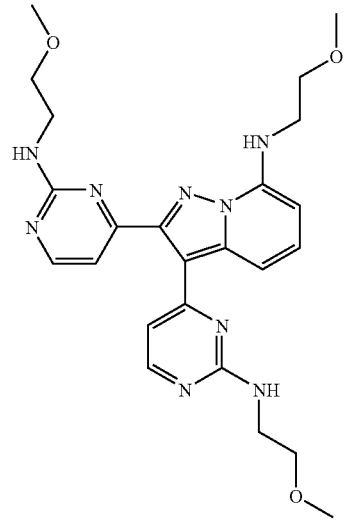

To a −78° C. solution of 2,3-bis[2-(methylsulfanyl)pyrimidin-4-yl]pyrazolo[1,5-a]pyridine (0.72 g, 2.0 mmol) in tetrahydrofuran (50 mL) was added a 2 M solution of lithium diisopropylamide in heptane/tetrahydrofuran/ethylbenzene (2.9 mL, 5.9 mmol) dropwise. The reaction mixture was stirred for 15 minutes, then carbon tetrachloride (5 mL) was added. The reaction mixture was stirred for 1 hour and quenched with brine and extracted with ethyl acetate (3×25 mL). The organic phase was washed with brine (3×25 mL), dried over magnesium sulfate, and concentrated under reduced pressure. The residue was purified by silica gel chromatography (1:9 acetone:dichloromethane) to give 260 mg (32%) of 7-chloro-2,3-bis[2-(methylsulfanyl)pyrimidin-4-yl]pyrazolo[1,5-a]pyridine. 7-Chloro-2,3-bis[2-(methylsulfanyl)pyrimidin-4-yl]pyrazolo[1,5-a]pyridine (0.098 g, 0.24 mmol) was dissolved in dichlormethane (3 mL) and cooled to 0° C. To the solution was added 3-chloroperoxybenzoic acid (0.13 g, 0.73 mmol). The reaction mixture was allowed to warm to room temperature and stirred overnight The mixture was diluted with dichloromethane, washed with saturated aqueous sodium bicarbonate, and concentrated under reduced pressure. To 7-chloro-2,3-bis[2-(methylsulfinyl)pyrimidin-4-yl]pyrazolo[1,5-a]pyridine (0.027 g, 0.062 mmol) was added 2-methoxyethylamine (2 mL) and the reaction was heated to 100° C. in a sealed tube overnight. The reaction mixture was cooled to room temperature and concentrated by evaporation under reduced pressure. The residue was purified by silica gel chromatography eluting with 1:1 acetone:dichloromethane to give 15 mg (49%) of N-(2-methoxyethyl)-2,3-bis{2-[(2-methoxyethyl)amino]pyrimidin-4-yl}pyrazolo[1,5-a]pyridin-7-amine. $^1$H NMR (CDCl$_3$): δ 8.41 (d, 1H), 8.16 (d, 1H), 7.69 (d, 1H), 7.36 (d, 1H), 7.05 (m, 1H), 6.65 (d, 1H), 6.33 (t, 1H), 6.09 (d, 1H), 5.57 (m, 1H), 5.42 (t, 1H), 3.37–3.80 (m, 21H); MS m/z 494 (M+1).

EXAMPLE 8

N-Butyl-2,3-bis[2-(butylamino)pyrimidin-4-yl]pyrazolo[1,5-a]pyridin-7-amine

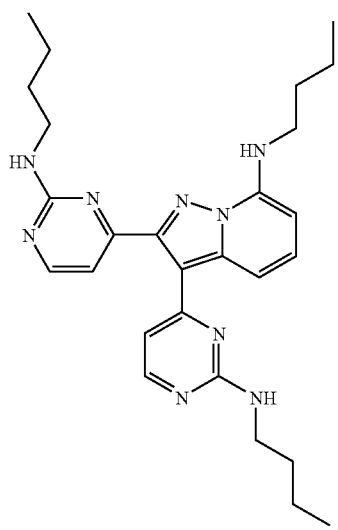

N-Butyl-2,3-bis[2-(butylamino)pyrimidin-4-yl]pyrazolo[1,5-a]pyridin-7-amine was prepared by treating 7-chloro-2,3-bis[2-(methylsulfinyl)pyrimidin-4-yl]pyrazolo[1,5-a]pyridine with n-butylamine as described in Example 7. $^1$H NMR, (400 MHz, CDCl$_3$): δ 8.35 (d, 1H), 8.09 (d, 1H), 7.62 (d, 1H), 7.30 (t, 1H), 6.93 (m, 1H), 6.57 (d, 1H), 6.40 (d, 1H), 6.20 (d, 1H), 5.17 (m, 1H), 5.08 (m, 1H), 3.34–3.46 (m, 6H), 1.75 (m, 2H), 1.35–1.66 (m, 10H), 0.90–1.00 (m, 9H); MS m/z 488 (M+1).

EXAMPLE 9

N-Cyclopropyl-2,3-bis[2-(cyclopropylamino)pyrimidin-4-yl]pyrazolo[1,5-a]pyridin-7-amine

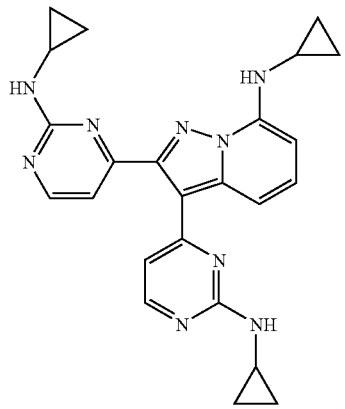

N-Cyclopropyl-2,3-bis[2-(cyclopropylamino)pyrimidin-4-yl]pyrazolo[1,5-a]pyridin-7-amine was prepared by treating 7-chloro-2,3-bis[2-(methylsulfinyl)pyrimidin-4-yl]pyrazolo[1,5-a]pyridine with cyclopropylamine as described in Example 7. $^1$H NMR, (CDCl$_3$): δ 8.47 (d, 1H), 8.19 (d, 1H), 7.86 (d, 1H), 7.37 (t, 1H), 7.04 (d, 1H), 6.71 (d, 1H), 6.44 (d, 1H), 6.36 (s, 1H), 5.53 (s, 1H), 5.39 (s, 1H), 2.62–290 (m, 3H), 0.77–0.96 (m, 8H), 0.56–0.70 (m, 4H); MS m/z 440 (M+1).

EXAMPLE 10

7-Morpholin-4-yl-2,3-bis(2-morpholin-4-yl)pyrimidin-4-yl)pyrazolo[1,5-a]pyridine

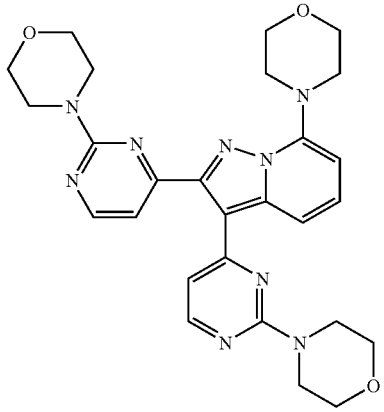

7-Morpholin-4-yl-2,3-bis(2-morpholin-4-yl pyrimidin-4-yl)pyrazolo[1,5-a]pyridine was prepared by treating 7-chloro-2,3-bis[2-(methylsulfinyl)pyrimidin-4-yl]pyrazolo[1,5-a]pyridine with morpholine as described in Example 7. $^1$H NMR, (400 MHz, CDCl$_3$): δ 8.43 (d, 1H), 8.21 (d, 1H), 7.83 (d, 1H), 7.28 (dd, 1H), 7.19 (d, 1H), 6.71 (d, 1H), 6.34 (d, 1H), 4.01 (t, 4H), 3.80 (m, 8H), 3.67 (m, 8H), 3.49 (m, 4H); MS m/z 530 (M+1).

EXAMPLE 11

N-Isobutyl-2,3-bis[2-(isobutylamino)pyrimidin-4-yl]pyrazolo[1,5-a]pyridin-7-amine

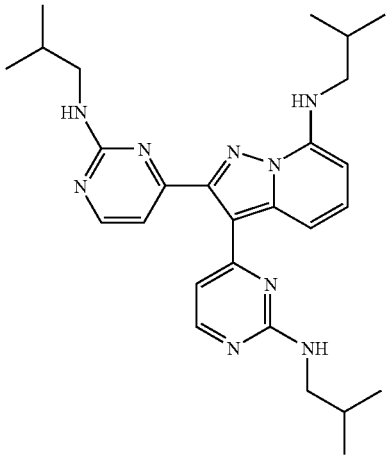

N-Isobutyl-2,3-bis[2-(isobutylamino)pyrimidin-4-yl]pyrazolo[1,5-a]pyridin-7-amine pyridine was prepared by treating 7-chloro-2,3-bis[2-(methylsulfinyl)pyrimidin-4-yl]pyrazolo[1,5-a]pyridine with isobutylamine as described in Example 7. $^1$H NMR, (400 MHz, CDCl$_3$): δ 8.35 (d, 1H), 8.09 (d, 1H), 7.59 (d, 1H), 7.30 (d, 1H), 6.94 (bs, 1H), 6.57 (m, 1H), 6.16 (t, 1H), 6.00 (d, 1H), 5.26 (bs, 1H), 5.17 (bs, 1H), 3.25 (t, 3H), 3.18 (t, 3H), 2.00–2.15 (m, 1H), 1.85–1.95 (m, 2H), 0.90–1.10 (m, 18H); MS m/z 488 (M+1).

EXAMPLE 12

N-Benzyl-2,3-bis[2-(benzylamino)pyrimidin-4-yl]pyrazolo[1,5-a]pyridin-7-amine

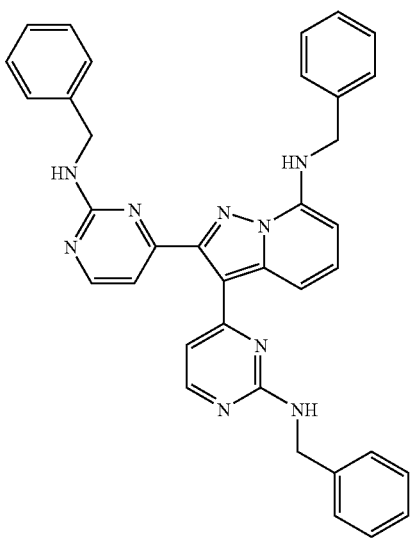

N-Benzyl-2,3-bis[2-(benzylamino)pyrimidin-4-yl]pyrazolo[1,5-a]pyridin-7-amine was prepared by treating 7-chloro-2,3-bis[2-(methylsulfinyl)pyrimidin-4-yl]pyrazolo[1,5-a]pyridine with benzylamine as described in Example 7. $^1$H NMR, (400 MHz, CDCl$_3$): δ 8.37 (d, 1H), 8.02 (d, 1H), 7.16–7.40 (m, 16H), 7.12 (t, 1H), 7.02 (bs, 1H), 6.63 (d, 1H), 6.48 (t, 1H), 5.96 (d, 1H), 5.58 (bs, 1H), 5.46 (1H), 4.65 (d, 2H), 4.38–4.62 (m, 4H); MS m/z 590 (M+1).

EXAMPLE 13

N-Isopropyl-2,3-bis[2-(isopropylamino)pyrimidin-4-yl]pyrazolo[1,5-a]pyridin-7-amine

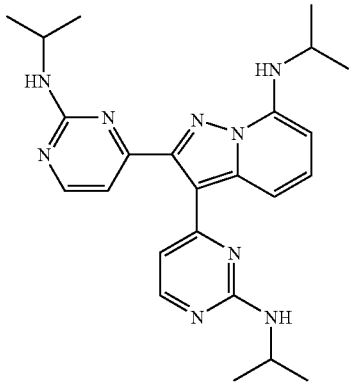

N-Isopropyl-2,3-bis[2-(isopropylamino)pyrimidin-4-yl]pyrazolo[1,5-a]pyridin-7-amine was prepared by treating 7-chloro-2,3-bis[2-(methylsulfinyl)pyrimidin-4-yl]pyrazolo[1,5-a]pyridine with isopropylamine as described in Example 7. $^1$H NMR, (CDCl$_3$): δ 8.39 (d, 1H), 8.14 (d, 1H), 7.52 (m, 1H), 7.36 (d, 1H), 6.96 (m, 1H), 6.60 (d, 1H), 6.06 (d, 1H), 5.99 (d, 1H), 5.08 (m, 1H), 4.99 (m, 1H), 4.05–4.25 (m, 2H), 3.80–3.99 (m, 1H), 1.42 (d, 6H), 1.30 (d, 6H), 1.24 (m, 6H); MS m/z 446 (M+1).

EXAMPLE 14

2-(2-Fluoro-4-pyridinyl)-3-[2-(methylsulfanyl)-4-pyrimidinyl]pyrazolo-[1,5-a]pyridine

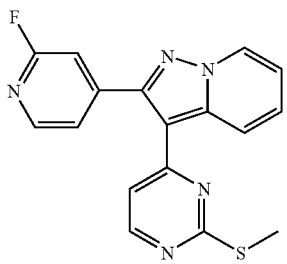

a) 4-[(2-Fluoro-4-pyridinyl)ethynyl]-2-(methylsulfanyl)pyrimidine

4-Iodo-2-fluoropyridine (1.09 g, 4.9 mmol) was dissolved in anhydrous tetrahydrofuran (20 mL). To this solution was added triethylamine (0.9 mL, 6.5 mmol), copper (I) iodide (80 mg, 0.4 mmol) and dichlorobis(triphenylphosphine) palladium (II) (60 mg, 0.32 mmol). 4-Ethynyl-2-(methylsulfanyl)pyrimidine (example 4, 0.75 g, 4.9 mmol) in tetrahydrofuran was added dropwise to the resulting solution. After the addition was complete the reaction was stirred at room temperature overnight. The mixture was concentrated to give a syrup, that was purified by silica gel chromatography (1:1 ethyl acetate:hexane) to give after removal of solvents 0.84 g (70%) of 4-[(2-fluoro-4-pyridinyl)ethynyl]-2-(methylsulfanyl)pyrimidine as a white solid. $^1$H NMR (CDCl$_3$): δ 8.61 (d, 1H), 8.32 (d, 1H), 7.39 (d, 1H), 7.17 (m, 2H), 2.64 (s, 3H); $^{19}$F NMR (CDCl$_3$): 8–66.82; MS m/z 246 (M+1).

b) 2-(2-Fluoro-4-pyridinyl)-3-[2-(methylsulfanyl)-4-pyrimidinyl]pyrazolo[1,5-a]pyridine. 4-[(2-Fluoro-4-pyridinyl)ethynyl]-2-(methylsulfanyl)pyrimidine (740 mg, 3.0 mmol) was dissolved in acetonitrile (10 mL). To this solution was added 1-aminopyridinium iodide (670 mg, 3.0 mmol) and 1,8-diazobicyclo[5.4.0]undec-7-ene (0.460 mL, 3.0 mmol) at 0° C. and the resulting mixture was allowed to warm to room temperature and stirred at room temperature for 2 days. The resulting reddish suspension was concentrated in vacuo. Ethyl acetate and water were added to this residue. The phases were separated and the aqueous phase extracted with additional ethyl acetate. The organics were combined, dried over magnesium sulfate, filtered and concentrated. Purification by silica gel chromatography (1:1 ethyl acetate:hexane) gave 550 mg (55%) of 2-(2-fluoro-4-pyridinyl)-3-[2-(methylsulfanyl)-4-pyrimidinyl]pyrazolo[1,5-a]pyridine as a solid. $^1$H NMR (CDCl$_3$): δ 8.62 (d, 1H), 8.41 (d, 1H), 8.39 (d, 1H), 8.35 (d, 1H), 7.47 (m, 2H), 7.25 (m, 1H), 7.06 (dt, 1H), 6.83 (d, 1H), 2.53 (s, 3H); $^{19}$F NMR δ CDCl$_3$: -67.12; $^{13}$C NMR (CDCl$_3$): δ 173.16, 164.23 (d, J$_{CF}$ 239.7 Hz), 159.67, 156.97, 150.17 (d, J$_{CF}$ 3.1 Hz), 148.29 (d, J$_{CF}$ 15.3 Hz), 146.73, (d, J$_{CF}$ 8.3 Hz), 141.07, 129.08, 127.10, 122.05 (d, J$_{CF}$ 3.8 Hz), 119.80, 114.82, 114.56, 110.07 (d, J$_{CF}$ 38.1 Hz), 107.96; MS 338 m/z (M+1).

EXAMPLE 15

4-[2-(2-Fluoro-4-pyridinyl)pyrazolo[1,5-a]pyridin-3-yl]-N-isopropyl-2-pyrimidinamine

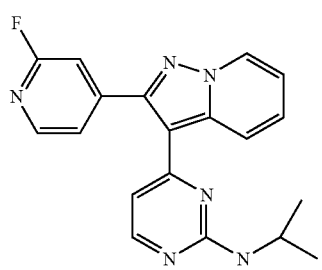

2-(2-Fluoro-4-pyridinyl)-3-[2-(methylsulfanyl)-4-pyrimidinyl]pyrazolo[1,5-a]pyridine (0.18 g, 0.53 mmol) was dissolved in dichloromethane (10 mL) and the resulting solution cooled to 0° C. in an ice bath. To this solution was added dropwise 3-chloroperoxybenzoic acid (230 mg, 57–86%) in dichloromethane. This reaction mixture was stirred at 0° C. for 10 minutes. Additional dichloromethane was added and the reaction mixture was extracted with saturated aqueous potassium carbonate. The organic phase was dried over magnesium sulfate, filtered and concentrated to give a foam. This foam was dissolved in isopropylamine and heated to 50° C. for 2 hours. The resulting mixture was concentrated to a solid that was purified by by silica gel chromatography (1:1 ethyl acetate:hexane) give 90 mg (48%) of the title compound as a solid. $^1$H NMR (CDCl$_3$): δ 8.56 (d, 1H), 8.31 (m, 2H), 8.19 (d, 1H), 7.52 (m, 1H), 7.40 (t, 1H), 7.33 (broad s, 1H), 7.02 (t, 1H), 6.45 (d, 1H), 5.20 (m, 1H), 4.20 (m, 1H), 1.31 (d, 5H); $^{19}$F NMR (CDCl$_3$): 8–67.68; MS m/z 349 (M+1).

EXAMPLE 16

N-Isopropyl-4-[2-[2-(isopropylamino)-4-pyridinyl]pyrazolo[1,5-a]pyridin-3-yl}-2-pyrimidinamine

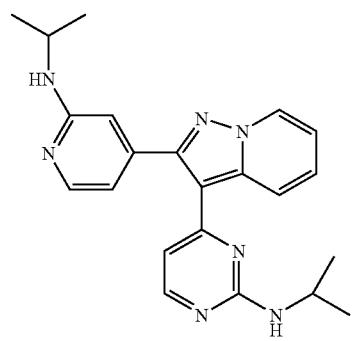

4-[2-(2-Fluoro-4-pyridinyl)pyrazolo[1,5-a]pyridin-3-yl]-N-isopropyl-2-pyrimidinamine (80 mg, 0.23 mmol) was dissolved in isopropylamine (10 mL) in a pressure vessel and the resulting solution heated at 120° C. for 4 days. The resulting mixture was concentrated to a solid that was purified by by silica gel chromatography (1:1 ethyl acetate:hexane) to give 50 mg (56%) of the title compound as a solid. $^1$H NMR (CDCl$_3$): δ 8.53 (d, 1H), 8.43 (d, 1H), 8.1.5 (two d, 2H), 7.35 (t, 1H), 6.96 (t, 1H), 6.82 (d, 1H), 6.65 (s, 1H), 6.50 (d, 1H), 5.08 (d, 1H), 4.60 (d, 1H), 4.25 (m, 1H), 3.94 (m, 1H), 1.33 (d, 6H), 1.25 (d, 6H); MS m/388 (M+1).

EXAMPLE 17

3-[2-(Cyclopropylamino)-4-pyrimidinyl]-N-isopropyl-2-[2-(isopropylamino)-4-pyridinyl]pyrazolo[1,5-a]pyridin-7-amine

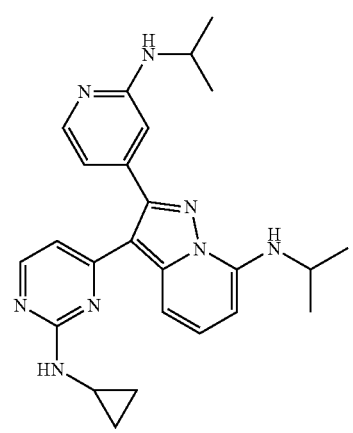

a) 2-(2-Fluoro-4-pyridinyl)-3-[2-(methylsulfinyl)-4-pyrimidinyl]pyrazolo[1,5-a]pyridine To a cold (0° C.) solution of 2-(2-fluoro-4-pyridinyl)-3-[2-(methylsulfanyl)-4-pyrimidinyl]pyrazolo[1,5-a]pyridine (1.81 g, 5.36 mmol) in dichloromethane (100 mL) was added 3-chloroperoxybenzoic acid (1.39 g, 70%, 5.63 mmol). The reaction mixture was warmed to room temperature and stirred 16 hours. The reaction mixture was diluted with 100 mL dichloromethane and washed with saturated aqueous sodium bicarbonate solution. The organic layer was concentrated in vacuo to give 1.84 g of 2-(2-fluoro-4-pyridinyl)-3-[2-(methylsulfinyl)-4-pyrimidinyl]pyrazolo[1,5-a]pyridine of 90% purity as a greenish grey solid. This material was carried on without further purification. $^1$H NMR (DMSO-$d_6$) δ 8.92 (d, 1H), 8.75 (d, 1H), 8.54 (d, 1H), 8.38 (d, 1H), 7.63–7.59 (m, 2H), 7.48 (s, 1H), 7.32 (d, 1H), 7.24 (t, 1H), 2.87 (s, 3H); $^{19}$F NMR (DMSO-$d_6$) δ −68.05; MS m/z 354 (M+1).

b) N-Cyclopropyl-4-[2-(2-fluoro-4-pyridinyl)pyrazolo[1,5-a]pyridin-3-yl]-2-pyrimidinamine A solution of 2-(2-fluoro-4-pyridinyl)-3-[2-(methylsulfinyl)-4-pyrimidinyl]pyrazolo[1,5-a]pyridine (430 mg, 90%, ~1.1 mmol) in cyclopropylamine (4 mL, 57.7 mmol) was heated at 45° C. in a sealed glass tube for 6 hours. The excess cyclopropylamine was removed in vacuo to provide crude N-cyclopropyl-4-[2-(2-fluoro-4-pyridinyl)pyrazolo[1,5-a]pyridin-3-yl]-2-pyrimidinamine (370 mg, 97%). A small portion of the crude material was chromatographed (19:1 dichloromethane:acetone to 9:1 dichloromethane:acetone) to provide material as a light yellow solid. $R_f$ 0.26 (9:1 dichloromethane:acetone); $^1$H NMR (CDCl$_3$) δ 8.52 (d, 1H), 8.42 (d, 1H), 8.29 (d, 1H). 8.21 (d, 1H), 7.51 (d, 1H), 7.36 (d, 1H), 7.32 (s, 1H), 6.98 (t, 1H), 6.48 (d, 1H), 5.69 (br, 1H), 2.81 (m, 1H), 0.83 (m, 2H), 0.61 (m, 2H); MS m/z 347 (M+1).

c) N-Cyclopropyl-4-{2-[2-(isopropylamino)-4-pyridinyl]pyrazolo[1,5-a]pyridin-3-yl}-2-pyrimidinamine A solution of N-cyclopropyl-4-[2-(2-fluoro-4-pyridinyl)pyrazolo[1,5-a]pyridin-3-yl]-2-pyrimidinamine (206 mg, 0.595 mmol) in isopropylamine (3 mL, 35.2 mmol) was heated at 150° C. in a steel bomb for 16 hours. The excess isopropylamine was removed under a stream of nitrogen. The crude material was triturated with ether to provide N-cyclopropyl-4-{2-[2-(isopropylamino)-4-pyridinyl]pyrazolo[1,5-a]pyridin-3-yl}-2-pyrimidinamine (185 mg, 80%) as a tan solid. $^1$H NMR (CDCl$_3$) δ 8.60 (d, 1H), 8.51 (d, 1H), 8.14 (m, 2H), 7.32 (t, 1H), 6.93 (t, 1H), 6.80 (d, 1H), 6.62 (s, 1H), 6.55 (d, 1H), 5.62 (br, 1H), 4.60 (d, 1H), 3.87 (m, 1H), 2.85 (m, 1H), 1.29 (d, 3H), 1.22 (d, 3H), 0.86 (m, 2H), 0.63 (m, 2H); MS m/z 386 (M+1).

d) 3-[2-(Cyclopropylamino)-4-pyrimidinyl]-N-isopropyl-2-[2-(isopropylamino)-4-pyridinyl]pyrazolo[1,5-a]pyridin-7-amine To a cold (−78° C.) solution of N-cyclopropyl-4-{2-[2-(isopropylamino)-4-pyridinyl]pyrazolo[1,5-a]pyridin-3-yl}-2-pyrimidinamine (178 mg, 0.462 mmol) in tetrahydrofuran (15 mL) was added n-butyllithium (866 μL, 1.6 M in hexanes, 1.39 mmol) dropwise. The reaction mixture was stirred at −78° C. for 30 minutes, then carbon tetrachloride (179 μL, 1.85 mmol) was added dropwise. The resultant mixture was warmed to room temperature and stirred 2 hours. The reaction mixture was quenched with water and diluted with ethyl acetate. The organic layer was washed with water and brine, then dried over magnesium sulfate. Filtration and concentration provided crude 4-{7-chloro-2-[2-(isopropylamino)-4-pyridinyl]pyrazolo[1,5-a]pyridin-3-yl}-N-cyclopropyl-2-pyrimidinamine. This material was taken up in isopropylamine (3 mL, 35.2 mmol) and heated in a steel bomb at 120° C. for 16 hours. The reaction mixture was cooled and the excess isopropylamine was removed under a stream of nitrogen. Preparative HPLC provided 3-[2-(cyclopropylamino)-4-pyrimidinyl]-N-isopropyl-2-[2-(isopropylamino)-4-pyridinyl]pyrazolo[1,5-a]pyridin-7-amine (10 mg, 5%) as a yellow solid. $^1$H NMR (CDCl$_3$) δ 8.10–8.07 (m, 2H), 7.87 (d, 1H), 7.35 (t, 1H), 6.85 (d, 1H), 6.69 (s, 1H), 6.51 (d, 1H), 6.06 (d, 1H), 5.94 (d, 1H), 5.68 (br, 1H), 4.16 (br, 1H), 3.93–3.79 (m, 2H), 2.85 (m, 1H), 1.40 (d, 6H), 1.25 (d, 6H), 0.87 (m, 2H), 0.64 (m, 2H); MS m/z 443 (M+1).

EXAMPLE 18

N-Cyclopentyl-2-[2-(cyclopentylamino)-4-pyridinyl]-3-[2-(isopropylamino)-4-pyrimidinyl]pyrazolo[1,5-a]pyridin-7-amine

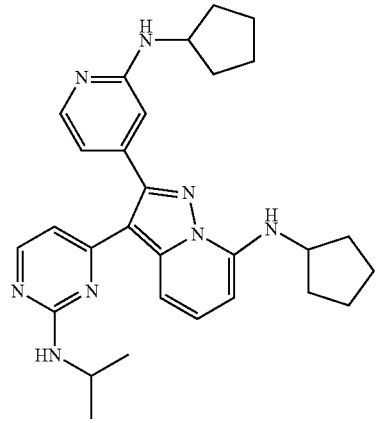

a) 4-[2-(2-Fluoro-4-pyridinyl)pyrazolo[1,5-a]pyridin-3-yl]-N-isopropyl-2-pyrimidinamine.

To a cold (0° C.) solution of 2-(2-fluoro-4-pyridinyl)-3-[2-(methylsulfanyl)-4-pyrimidinyl]pyrazolo[1,5-a]pyridine (200 mg, 0.59 mmol) in dichloromethane (10 mL) was added m-chloroperoxybenzoic acid (154 mg, 70%/o, 0.62 mmol). The reaction mixture was warmed to room temperature and stirred 16 hours. The reaction mixture was diluted with dichloromethane and washed with saturated aqueous sodium bicarbonate solution. The organic layer was concentrated in vacuo to provide a green foam, which was dissolved in isopropylamine and heated in a sealed glass pressure tube at 45° C. for 16 hours. The reaction mixture was cooled and the excess isopropylamine was removed under a stream of nitrogen to provide crude 4-[2-(2-fluoro-4-pyridinyl)pyrazolo[1,5-a]pyridin-3-yl]-N-isopropyl-2-pyrimidinamine (204 mg, 99%). $R_f$ 0.25 (9:1 dichloromethane:acetone); MS m/349 (M+1).

b) N-Cyclopentyl-N-(4-{3-[2-(isopropylamino)-4-pyrimidinyl]pyrazolo[1,5-a]pyridin-2-yl}-2-pyridinyl)amine A solution of crude 4-[2-(2-fluoro-4-pyridinyl)pyrazolo [1,5-a]pyridin-3-yl]-N-isopropyl-2-pyrimidinamine (204 mg, 0.586 mmol) in cyclopentylamine (2 mL, 20.3 mmol) was heated at 135° C. in a sealed glass tube for 16 hours. The reaction mixture was cooled and the excess cyclopentylamine was removed in vacuo. The resultant residue was partitioned between ethyl acetate and saturated aqueous sodium bicarbonate solution. The organic layer was washed with brine and dried over magnesium sulfate. Filtration and concentration, followed by flash chromatography (1:1 hexanes:ethyl acetate to 100% ethyl acetate) provided N-cyclopentyl-N-(4-{3-[2-(isopropylamino)-4-pyrimidinyl]pyrazolo[1,5-a]pyridin-2-yl}-2-pyridinyl)amine (155 mg, 640%). $R_f$ 0.16 (1:2 hexanes:ethyl acetate); $^1$H NMR (CDCl$_3$) δ 8.49 (d, 1H), 8.39 (d, 1H), 8.13–8.08 (m, 2H), 7.29 (t, 1H), 6.89 (t, 1H), 6.80 (d, 1H), 6.63 (s, 1H), 6.46 (d, 1H), 5.23 (br, 1H), 4.86 (d, 1H), 4.21 (m, 1H), 3.93 (m, 1H), 1.95 (m, 2H), 1.70–1.42 (m, 6H), 1.27 (d, 6H); MS m/z 414 (M+1).

c) 4-{7-Chloro-2-[2-(cyclopentylamino)-4-pyridinyl]pyrazolo[1,5-a]pyridin-3-yl}-N-isopropyl-2-pyrimidinamine In a similar manner as described in Example 17 from N-cyclopentyl-N-(4-{3-[2-(isopropylamino)-4-pyrimidinyl]pyrazolo[1,5-a]pyridin-2-yl}-2-pyridinyl)amine (155 mg, 0.375 mmol), n-butyllithium (700 µL 1.6 M in hexanes, 1.12 mmol), and carbon tetrachloride (145 µL, 1.50 mmol) was formed 4-{7-chloro-2-[2-(cyclopentylamino)-4-pyridinyl]pyrazolo[1,5-a]pyridin-3-yl}-N-isopropyl-2-pyrimidinamine. Flash chromatography (1:1 hexanes:ethyl acetate to 1:2 hexanes:ethyl acetate) provided sample (65 mg, 39%). $R_f$ 0.20 (1:1 hexanes:ethyl acetate); $^1$H NMR (CDCl$_3$) δ 8.40 (d, 1H), 8.14–8.11 (m, 2H), 7.27 (m, 1H), 7.07 (d, 1H), 6.82 (d, 1H), 6.66 (s, 1H), 6.46 (d, 1H), 5.11 (d, 1H), 4.79 (d, 1H), 4.21 (m, 1H), 3.98 (m, 1H), 1.98 (m, 2H), 1.74–1.44 (m, 6H), 1.30 (d, 6H); MS m/z 448 (M+1).

d) N-Cyclopentyl-2-[2-(cyclopentylamino)-4-pyridinyl]-3-[2-(isopropylamino)-4-pyrimidinyl]pyrazolo[1,5-a]pyridin-7-amine In a similar manner as described in Example 17 from 4-{7-chloro-2-[2-(cyclopentylamino)-4-pyridinyl]pyrazolo[1,5-a]pyridin-3-yl}-N-isopropyl-2-pyrimidinamine (30 mg, 0.067 mmol) and cyclopentylamine (1 mL, 10 mmol) was formed N-cyclopentyl-2-[2-(cyclopentylamino)-4-pyridinyl]-3-[2-(isopropylamino)-4-pyrimidinyl]pyrazolo[1,5-a]pyridin-7-amine (2 mg, 6%) as a yellow solid. $R_f$ 0.22 (1:1 hexanes:ethyl acetate); $^1$H NMR (CDCl$_3$) δ 8.09–8.05 (m, 2H), 7.70 (d, 1H), 7.34 (t, 1H), 6.86 (m, 1H), 6.69 (s, 1H), 6.44 (d, 1H), 6.07 (d, 1H), 6.01 (d, 1H), 5.85 (br, 1H), 5.20 (br, 1H), 4.21 (m, 1H), 4.02 (m, 1H), 3.93 (m, 1H), 2.15 (m, 2H), 1.97 (m, 2H), 1.84–1.51 (m, 12H), 1.29 (d, 6H); MS m/z 497 (M+1).

EXAMPLE 19

3-[2-(Cyclopentylamino)-4-pyrimidinyl]-N-isopropyl-2-[2-(isopropylamino)-4-pyridinyl]pyrazolo[1,5-a]pyridin-7-amine

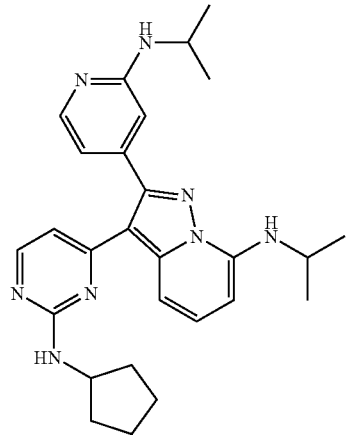

a) N-Cyclopentyl-4-{2-[2-(isopropylamino)-4-pyridinyl]pyrazolo[1,5-a]pyridin-3-yl}-2-pyrimidinamine.

In a similar manner as described in example 17 from 2-(2-fluoro-4-pyridinyl)-3-[2-(methylsulfinyl)-4-pyrimidinyl]pyrazolo[1,5-a]pyridine (410 mg, 1.16 mmol) and cyclopentylamine (4 mL, 40.5 mmol) was formed crude N-cyclopentyl-4-[2-(2-fluoro-4-pyridinyl)pyrazolo[1,5-a]pyridin-3-yl]-2-pyrimidinamine (385 mg), of which 260 mg (0.694 mmol) was dissolved in isopropylamine (3 mL, 35.2 mmol) and heated at 150° C. in a steel bomb for 16 hours. The reaction mixture was cooled and the excess isopropylamine was removed under a stream of nitrogen to provide N-cyclopentyl-4-{2-[2-(isopropylamino)-4-pyridinyl]pyrazolo[1,5-a]pyridin-3-yl}-2-pyrimidinamine (170 mg, 52% for 2 step procedure) as a beige solid. $^1$H NMR (CDCl$_3$) δ 8.50 (d, 1H), 8.41 (d, 1H), 8.13–8.08 (m, 2H), 7.32 (t, 1H), 6.92 (t, 1H), 6.80 (d, 1H), 6.62 (s, 1H), 6.47 (d, 1H), 5.26 (d, 1H), 4.63 (d, 1H), 4.34 (m, 1H), 3.85 (m, 1H), 2.11–2.04 (m, 2H), 1.79–1.51 (m, 6H), 1.22 (d, 6H); MS m/z 414 (M+1).

b) 4-{7-Chloro-2-[2-(isopropylamino)-4-pyridinyl]pyrazolo[1,5-a]pyridin-3-yl}-N-cyclopentyl-2-pyrimidinamine In a similar manner as described in Example 17 from N-cyclopentyl-4-{2-[2-(isopropylamino)-4-pyridinyl]pyrazolo[1,5-a]pyridin-3-yl}-2-pyrimidinamine (166 mg, 0.401 mmol), n-butyllithium (753 µL, 1.6 M in hexanes, 1.20 mmol) and carbon tetrachloride (155 µL, 1.60 mmol) was formed 4-{7-chloro-2-[2-(isopropylamino)-4-pyridinyl]pyrazolo[1,5-a]pyridin-3-yl}-N-cyclopentyl-2-pyrimidinamine (140 mg, 78%). $R_f$ 0.21 (1:1 hexanes:ethyl acetate); $^1$H NMR (CDCl$_3$) δ 8.36 (d, 1H), 8.19 (d, 1H), 8.07 (d, 1H), 7.36 (m, 1H), 7.13 (d, 1H), 6.90 (d, 1H), 6.81 (s, 1H), 6.52 (d, 1H), 5.25–5.21 (br, 2H), 4.35 (m, 1H), 3.89 (m, 1H), 2.18–2.04 (m, 2H), 1.80–1.50 (m, 6H), 1.22 (d, 6H).

c) 3-[2-(Cyclopentylamino)-4-pyrimidinyl]-N-isopropyl-2-[2-(isopropylamino)-4-pyridinyl]pyrazolo[1,5-a]pyridin-7-amine In a similar manner as described in Example 17 from 4-{7-chloro-2-[2-(isopropylamino)-4-pyridinyl]pyrazolo[1,5-a]pyridin-3-yl}-N-cyclopentyl-2-pyrimidinamine (35 mg, 0.0781 mmol) and isopropylamine (2 mL, 23.5 mmol) was formed 3-[2-(cyclopentylamino)-4-pyrimidinyl]-N-isopropyl-2-[2-(isopropylamino)-4-pyridinyl]pyrazolo[1,5-a]pyridin-7-amine (5 mg, 14%) as a yellow solid. $R_f$ 0.22 (1:1 hexanes:ethyl acetate); $^1$H NMR (CDCl$_3$) δ 8.48 (s, 1H), 7.99 (s, 1H), 7.94 (d, 1H), 7.65 (d, 1H), 7.36 (t, 1H), 6.84 (d, 1H), 6.75 (s, 1H), 6.45 (d, 1H), 6.07 (d, 1H), 5.92 (d, 1H), 4.61 (br, 1H), 4.29 (m, 1H), 3.87 (m, 1H), 3.74 (m, 1H), 2.04 (m, 2H), 1.76–1.55 (m, 6H), 1.39 (d, 6H), 1.25 (d. 6H); MS m/z 471 (M+1).

EXAMPLE 20

N-Cyclopentyl-3-[2-(cyclopentylamino)-4-pyrimidinyl]-2-[2-(isopropylamino)-4-pyridinyl]pyrazolo[1,5-a]pyridin-7-amine

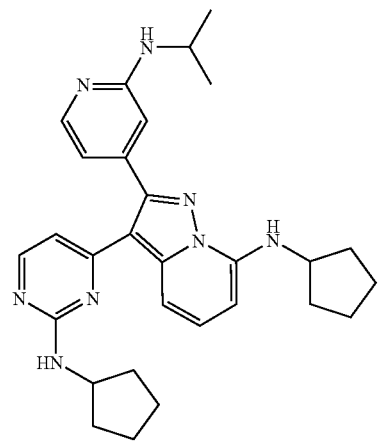

In a similar manner as described in Example 17 from 4-{7-chloro-2-[2-(isopropylamino)-4-pyridinyl]pyrazolo[1,5-a]pyridin-3-yl}-N-cyclopentyl-2-pyrimidinamine (35 mg, 0.0781 mmol) and cyclopentylamine (2 mL) was formed N-cyclopentyl-3-[2-(cyclopentylamino)-4-pyrimidinyl]-2-[2-(isopropylamino)-4-pyridinyl]pyrazolo[1,5-a]pyridin-7-amine (15 mg, 38%). $R_f$ 0.20 (39:1 dichloromethane:methanol); $^1$H NMR (CDCl$_3$) δ 8.13 (d, 1H), 8.03 (d, 1H), 7.72 (d, 1H), 7.30 (t, 1H), 6.80 (d, 1H), 6.60 (s, 1H), 6.42 (d, 1H), 6.03, (d, 1H), 5.99 (d, 1H), 5.13 (d, 1H), 4.51 (d, 1H), 4.32 (m, 1H), 3.99 (m, 1H), 3.85 (m, 1H), 2.15–1.91 (m, 4H), 1.81–1.50 (m, 12H), 1.21 (d, 6H); MS m/z 497 (M+1).

EXAMPLE 21

N-Cyclopentyl-3-[2-(cyclopentylamino)-4-pyridinyl]-2-(2-furyl)pyrazolo[1,5-a]pyridin-7-amine

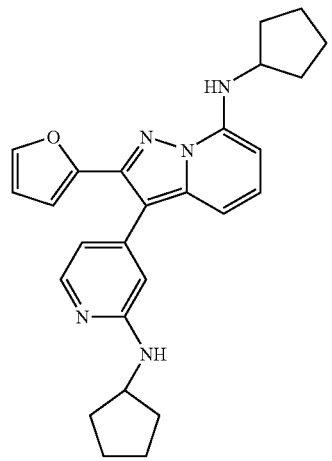

a) 2-(6-Chloro-2-pyridinyl)-1-(2-furyl)ethanone

The title compound was prepared from ethyl 2-furonate (6.3 g, 45 mmol) and 6-chloropicoline (5.7 g, 45 mmol) as a mixture of ketone and enol tautomers in a similar manner as described in Example 1. The product was purified by silica gel chromatography (3:1 hexane:ethyl acetate) to give 2-(6-chloro-2-pyridinyl)-1-(2-furyl)ethanone (4.7 g, 47%) as a solid. $^1$H NMR (CDCl$_3$) δ 8.02 (s, 1H), 7.82 (t, 1H), 7.57 (d, 1H), 7.39 (d, 2H), 6.73 (m, 1H), 4.35 (s, 2H); MS m/z 222 (M+1).

b) 2-(6-Chloro-2-pyridinyl)-1-(2-furyl)ethanone oxime

The title compound was prepared from 2-(6-chloro-2-pyridinyl)-1-(2-furyl)ethanone (4.5 g, 20 mmol) in a similar manner as described in example 1. The product was purified by silica gel chromatography (4:1 hexane:ethyl acetate) to give 2-(6-chloro-2-pyridinyl)-1-(2-furyl)ethanone oxime (2.7 g, 56%) as a solid. $^1$H NMR (DMSO-d$_6$) δ 11.4 (s, 1H), 7.76–7.70 (m, 2H), 7.31 (d, 1H), 7.19 (d, 1H), 6.75 (m, 1H), 6.52 (m, 1H), 4.1 (s, 2H); MS m/z 237 (M+1).

c) 7-Chloro-2-(2-furyl)pyrazolo[1,5-a]pyridine

The title compound was prepared from 2-(6-chloro-2-pyridinyl)-1-(2-furyl)ethanone oxime (2.7 g, 11 mmol) in a similar manner as described in example 1. The product was purified by silica gel chromatography (6:1 hexane:ethyl acetate) to give 1 g (40%) of 7-chloro-2-(2-furyl)pyrazolo[1,5-a]pyridine as a solid. $^1$H NMR (CDCl$_3$) δ 7.55 (broad s, 1H), 7.49 (d, 1H), 7.08 (dd, 1H), 6.95 (d, 1H), 6.90 (d, 1H), 6.86 (s, 1H), 6.51 (dd, 1H); MS m/z 219 (M+1).

d) 3-Bromo-7-chloro-2-(2-furyl)pyrazolo[1,5-a]pyridine

7-Chloro-2-(2-furyl)-pyrazolo[1,5-a]pyridine (0.23 g, 1.05 mmol) was dissolved in tetrahydrofuran (5 mL) and cooled to 0° C. N-Bromosuccinimide (0.19 g, 1.05 mmol) was added. The reaction was stirred for 1 hour. The reaction solution was poured into equal volumes (10 mL) of saturated aqueous ammonium chloride and ether. The ether layer was collected and the solvent removed in vacuo to give the crude product The product was purified by silica gel chromatography (6:1 hexane:ethyl acetate) to give 0.3 g (96%) of 3-bromo-7-chloro-2-(2-furyl)pyrazolo[1,5-a]pyridine as a solid. $^1$H NMR (CDCl$_3$) δ 7.63 (d, 1H), 7.51 (d, 1H), 7.29 (d, 1H), 7.21 (dd, 1H), 6.98 (d, 1H), 6.58 (dd, 1H); MS m/z 298 (M+1).

e) N-[3-Bromo-2-(2-furyl)pyrazolo[1,5-a]pyridin-7-yl]-N-cyclopentylamine

3-Bromo-7-chloro-2-(2-furyl)pyrazolo[1,5-a]pyridine (0.3 g, 1 mmol) was dissolved in toluene (10 mL). 2,2'-Bis(diphenylphosphino)-1,1'-binaphthyl (0.048 g, 0.06 mmol), palladium(II)acetate (0.01 g, 0.04 mmol) and cesium carbonate (0.82 g, 2.6 mmol) was added. Cyclopropylamine (0.5 mL) was added and the reaction was heated in an 85° C. oil bath for 4 hours. 2,2'-Bis(diphenylphosphino)-1,1'-binaphthyl (0.048 g, 0.06 mmol), and palladium(II)acetate (0.01 g, 0.04 mmol) were added again and the reaction heated in a 105° C. oil bath for 4 hours. The reaction mixture was poured into equal volumes (10 mL) of saturated aqueous ammonium chloride and ether. The ether layer was collected and the solvent removed in vacuo to give the crude product. The product was purified by silica gel chromatography (6:1 hexane:ethyl acetate) to give 0.25 g (72%) of N-[3-bromo-2-(2-furyl)pyrazolo[1,5-a]pyridin-7-yl]-N-cyclopentylamine as a solid. $^1$H NMR (CDCl$_3$) δ 7.6 (broad s, 1H), 7.24 (1H), 7.10 (m, 1H), 6.86 (m, 1H), 6.57 (m, 1H), 5.94 (m, 1H), 4.0 (m, 1H), 2.19–2.09 (m, 2H); 1.88–1.77 (m, 4H), 1.77–1.64 (m, 2H); MS m/z 345, 348 (M+1).

f) 2-Fluoropyridin-4-ylboronic acid

To a stirred solution of n-butyl lithium (3.2 mL 2.5M, 8.0 mmol) in dry diethyl ether (20 mL) at −78° C. was added a solution of 2-fluoro-4-iodopyridine (1.5 g, 6.7 mmol) in dry ether (10 mL) and the reaction mixture was stirred at −78° C. for 10 minutes. Tributyl borate (2.4 mL, 2.01 g, 8.7 mmol) was added and the reaction mixture was allowed to warm to room temperature over 2 hours. Water (5 mL) was added followed by 2N aqueous sodium hydroxide solution (10 mL) to dissolve the solids. The organic phase was separated. The aqueous phase was acidified to pH 3 using 6N hydrochloric acid and the resulting white solid was collected by filtration and dried under vacuum to give the title compound, 0.74 g (78%). $^1$H NMR (DMSO-d$_6$) δ 8.65 (broad s, 2H), 8.21 (d, 1H), 7.59 (t, 1H), 7.37 (d, 1H).

g) N-Cyclopentyl-3-(2-fluoro-4-pyridinyl)-2-(2-furyl)pyrazolo[1,5-a]pyridin-7-amine N-[3-Bromo-2-(2-furyl)pyrazolo[1,5-a]pyridin-7-yl]-N-cyclopentylamine (0.2 g, 0.6 mmol) was dissolved in N,N-dimethylformamide (8 mL). To this solution was added 2-fluoro-4-pyridinylboronic acid (0.09 g, 0.64 mmol), dichlorobis(triphenylphosphine)-palladium (II) (0.020 g, 0.03 mmol) and saturated aqueous sodium carbonate (580 μl). The resulting solution was heated in a 75° C. oil bath overnight. Water was added to the reaction mixture and the product was extracted with ethyl acetate. The organic phase was dried (magnesium sulfate), filtered and concentrated to a solid. The product was purified by silica gel chromatography (7:1 hexane:ethyl acetate) to give 50 mg (24%) of N-cyclopentyl-3-(2-fluoro-4-pyridinyl)-2-(2-furyl)pyrazolo [1,5-a]pyridin-7-amine as a solid. $^1$H NMR (CDCl$_3$) δ 8.1 (d, 1H), 7.5 (s, 1H), 7.24 (1H), 7.03(s, 1H), 6.96 (d, 1H), 6.75 (d, 1H), 6.5 (m, 1H), 6.01 (m, 2H), 4.0 (m, 1H), 2.19–2.09 (m, 2H); 1.88–1.77 (m, 4H), 1.77–1.64 (m, 2H); MS m/363 (M+1).

h) N-Cyclopentyl-3-[2-(cyclopentylamino)-4-pyridinyl]-2-(2-furyl)pyrazolo[1,5-a]pyridin-7-amine N-Cyclopentyl-3-(2-fluoro-4-pyridinyl)-2-(2-furyl)pyrazolo[1,5-a]pyridin-7-amine (0.05 g, 0.02 mmol) was dissolved in cyclopentylamine (1 mL and heated) in a 135° C. oil bath for 4 days. The amine was removed in vacuo. The product was purified by silica gel chromatography (7:1 hexane:ethyl acetate) to give 25 mg (42%) of N-cyclopentyl-3-[2-(cyclopentylamino)-4-pyridinyl]-2-(2-furyl)pyrazolo [1,5-a]pyridin-7-amine. $^1$H NMR (CDCl$_3$) δ 8.1 (d, 1H), 7.51 (s, 1H), 7.17 (t, 1H), 6.94 (d, 1H), 6.69 (m, 2H), 6.5 (s, 1H), 6.45 (m, 1H), 6.00 (d, 1H). 5.95 (d, 1H), 4.6 (br d, 1H), 4.0 (m, 1H), 3.92 (m, 1H), 2.19–2.09 (m, 2H), 2.03–1.95 (m, 2H), 1.88–1.43 (m, 8H), 1.32–1.22 (m, 2H);MS m/z 428 (M+1).

EXAMPLE 22

N-Cyclopentyl-3-[2-(cyclopentylamino)-4-pyrimidinyl]-2-(3-methyl-2-furyl)pyrazolo[1,5-a]pyridin-7-amine

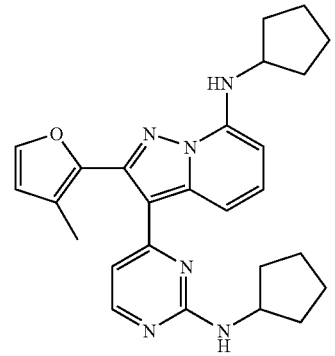

a) 2-(6-Chloro-2-pyridinyl)-1-(3-methyl-2-furyl)ethanone

To a cold (0° C.) solution of 6-chloro-2-picoline (25.8 mL 236 mmol) and methyl 3-methyl-2-furoate (33.08 g, 236 mmol) in tetrahydrofuran (300 mL) was added lithium bis(trimethylsilyl)amide (472 mL, 1.0 M in tetrahydrofuran, 472 mmol) dropwise via a pressure equalizing funnel over 1 hour. Upon complete addition, the cold bath was removed and the resultant solution was stirred at room temperature for 15 hours. The solution was concentrated. Methanol was added to quench the reaction resulting in a yellow solid precipitating. The precipitate was collected by filtration and washed with a small amount of cold methanol. 2-(6-Chloro-2-pyridinyl)-1-(3-methyl-2-furyl)ethanone (52.2 g, 94%)

was obtained as a yellow solid. ¹H NMR (CDCl₃): δ 7.61 (t, 1H), 7.43 (s, 1H), 7.23 (m, 2H), 6.40 (s, 1H), 4.36 (s, 2H), 2.37 (s, 3H). MS m/z 236 (M+1).

b) 2-(6-Chloro-2-pyridinyl)-1-(3-methyl-2-furyl) ethanone oxime

To a solution of 2-(6-chloro-2-pyridinyl)-1-(3-methyl-2-furyl)ethanone (52.2 g, 221 mmol) in methanol (500 mL) was added hydroxylamine hydrochloride (76.96 g, 1.11 mol) followed by an aqueous solution of sodium hydroxide (44.3 g, 1.11 mol). The resultant suspension was heated at reflux for 2 hours and then cooled to room temperature. The mixture was concentrated and water was added to the residue while stirring. After stirring for 20 minutes, a white solid precipitated. This solid was collected by filtration and washed with water to give 2-(6-chloro-2-pyridinyl)-1-(3-methyl-2-furyl)ethanone oxime (29.0 g, 52%) as a white solid. ¹H NMR (CDCl₃): δ 7.54 (t, 1H), 7.31 (s, 1H), 7.15 (d, 1H), 7.10 (d, 1H), 6.28 (s, 1H), 4.34 (s, 2H), 2.22 (S 3H). MS m/z 273 (M+1).

c) 7-Chloro-2-(3-methyl-2-furyl)pyrazolo[1,5-a] pyridine

To a solution of 2-(6-chloro-2-pyridinyl)-1-(3-methyl-2-furyl)ethanone oxime (24.5 g, 97.7 mmol) in 1,2-dimethoxyethane (200 mL) at 0° C. was added trifluoroacetic anhydride (14.5 mL, 103 mmol), while keeping the temperature below 10° C. After the addition was complete, the reaction was warmed to 15° C. The solution was then cooled to 0–5° C. and a solution of triethylamine (28.6 mL, 205 mmol) in 1,2-dimethoxyethane (30 mL) was added over 0.5 hours. The reaction mixture was allowed to warm to room temperature and was stirred for 2 hours. To this mixture was added iron(II) chloride (0.62 g, 4.9 mmol) and the reaction was heated at 75° C. for 15 hours. The reaction was concentrated, then ethyl acetate and water were added. The organic phase was separated, washed with water, dried (magnesium sulfate), filtered and concentrated. Purification by silica gel chromatography (9:1 hexanes:ethyl acetate) gave 7-chloro-2-(3-methyl-2-furyl)pyrazolo[1,5-a]pyridine (14.6 g, 640%) as yellow oil. ¹H NMR (CDCl₃): δ 7.52 (d, 1H), 7.48 (d, 1H), 7.10 (t, 1H), 6.92 (d, 1H), 6.86 (s, 1H), 6.42 (d, 1H), 2.49 (s, 3H). MS m/233 (M+1).

d) 7-Chloro-2-(3-methyl-2-furyl)pyrazolo[1,5-a] pyridine-3-carbaldehyde

A dry flask charged with dry N,N-dimethylformamide (100 mL) was treated with phosphorous oxychloride (8.8 mL, 94 mmol). The resultant solution was stirred at room temperature for 1 hour. 7-Chloro-2-(3-methyl-2-furyl)pyrazolo[1,5-a]pyridine (14.6 g, 63 mmol) was added and the reaction mixture was stirred for 2.5 hours. Water and dichloromethane were added to quench the reaction. The aqueous phase and organic phase were separated. The aqueous phase was extracted with dichloromethane. The organics were combined and washed with water, dried over magnesium sulfate, filtered and the filtrate was concentrated. Crystallization from a small amount of methanol gave 7-chloro-2-(3-methyl-2-furyl)pyrazolo[1,5-a]pyridine-3-carbaldehyde (12.4 g, 760%) as a peach color crystalline compound. ¹H NMR (CDCl₃): δ 10.58 (s, 1H), 8.43 (d, 1H), 7.58 (d, 1H), 7.48 (t, 1H), 7.21 (d, 1H), 6.51 (d, 1H), 2.56 (s, 3H). MS m/261 (M+1).

e) 1-[7-Chloro-2-(3-methyl-2-furyl)pyrazolo[1,5-a] pyridin-3-yl]-2-propyn-1-ol To a solution of 7-chloro-2-(3-methyl-2-furyl)pyrazolo[1,5-a]pyridine-3-carbaldehyde (11.56 g, 44.3 mmol) in tetrahydrofuran (200 mL) at −78° C. was added ethynylmagnesium bromide (133 mL, 0.5 M in tetrahydrofuran, 66.5 mmol). The mixture was allowed to warm to room temperature and stirred for 1 hour. Water was added to the reaction and the resulting mixture was extracted with ethyl acetate. The ethyl acetate phase was dried over magnesium sulfate, filtered and concentrated to a solid residue, 1-[7-chloro-2-(3-methyl-2-furyl)pyrazolo[1,5-a]pyridin-3-yl]-2-propyn-1-ol (12.29 g, 97%). ¹H-NMR (CDCl₃): δ 7.97 (d, 1H), 7.48 (d, 1H), 7.16 (t, 1H), 6.96 (d, 1H), 6.42 (d, 1H), 6.18 (m, 1H), 2.78 (m, 1H), 2.6 (d, 1H), 2.46 (s, 3H). MS m/z 287 (M+1).

f) 1-[7-Chloro-2-(3-methyl-2-furyl)pyrazolo[1,5-a] pyridin-3-yl]-2-propyn-1-one 1-[7-Chloro-2-(3-methyl-2-furyl)pyrazolo[1,5-a]pyridin-3-yl]-2-propyn-1-ol (12.29 g, 42.9 mmol) was dissolved in dichloromethane (200 mL) and manganese dioxide (112 g, 1.29 mol) was added. This slurry was stirred at room temperature for 2 hours. The manganese dioxide was removed by filtration and the filtrate was concentrated to a solid. This solid was purified by flash chromatography (dichloromethane) to give 1-[7-chloro-2-(3-methyl-2-furyl) pyrazolo[1,5-a]pyridin-3-yl]-2-propyn-1-one (7.53 g, 62%) as a white solid. ¹H-NMR (CDCl₃): δ 8.37 (d, 1H), 7.48 (m, 2H), 7.19 (d, 1H), 6.41 (d, 1H), 3.12 (s, 1H), 2.20 (s, 3H). MS m/z 285 (M+1).

g) 4-[7-Chloro-2-(3-methyl-2-furyl)pyrazolo[1,5-a] pyridin-3-yl]-N-cyclopentyl-2-pyrimidinamine Sodium ethylate solution (21% T, 0.5 mL, 1.43 mmol) was added to ethanol followed by cyclopentylguanidine hydrochloride (323 mg, 1.98 mmol). The mixture was stirred at room temperature for 30 minutes. 1-[7-Chloro-2-(3-methyl-2-furyl)pyrazolo[1,5-a]pyridin-3-yl]-2-propyn-1-one (313 mg, 1.10 mmol) was added to the resultant solution and stirred at room temperature for 15 hours. The reaction mixture was concentrated. Ethyl acetate and water were added to the residue. The phases were separated, the organic phase dried (magnesium sulfate), filtered and concentrated. The residue was recrystallized from ethyl acetate. 4-[7-Chloro-2-(3-methyl-2-furyl)pyrazolo[1,5-a]pyridin-3-yl]-N-cyclopentyl-2-pyrimidinamine (280 mg, 65%) was obtained as a yellow solid. ¹H-NMR (CDCl₃): δ 8.50 (d, 1H), 8.15 (d, 1H), 7.49 (d, 1H), 7.27 (t, 1H), 7.06 (d, 1H), 6.41 (d, 1H), 6.36 (d, 1H), 5.10 (d, 1H), 4.35 (m, 1H), 2.12 (s, 3H), 2.08 (m, 2H), 1.78–1.53 (m, 6H). MS m/z 394 (M+1).

h) N-Cyclopentyl-3-[2-(cyclopentylamino)-4-pyrimidinyl]-2-(3-methyl-2-furyl)pyrazolo[1,5-a]pyridin-7-amine To a solution of 4-[7-chloro-2-(3-methyl-2-furyl)pyrazolo[1,5-a]pyridin-3-yl]-N-cyclopentyl-2-pyrimidinamine (150 mg, 0.38 mmol) in cyclopentylamine (10 mL) was added racemic-2,2'-bis(diphenylphosphino)-1,1'-binaphthyl (76 mg, 0.12 mmol), cesium carbonate (247 mg, 0.76 mmol) and palladium (II) acetate (17 mg, 0.076 mmol). The resulting mixture was stirred at 100° C. for 3 hours. Water was added and the mixture was extracted with ethyl acetate. The ethyl acetate phase was washed with brine, dried over magnesium sulfate, filtered and concentrated in vacuo. The resulting residue was purified by flash chromatography (3:7 ethyl acetate:hexane) to give 147 mg (87%) of N-cyclopentyl-3-[2-(cyclopentylamino)-4-pyrimidinyl]-2-(3-methyl-2-furyl)pyrazolo[1,5-a]pyridin-7-amine as a yellow solid. $^1$H-NMR (CDCl$_3$): δ 8.07 (d, 1H), 7.85 (d, 1H), 7.50 (d, 1H), 7.31 (t, 1H), 6.42 (d, 1H), 6.25 (d, 1H), 6.04 (d, 1H), 6.00 (d, 1H), 5.06 (d, 1H), 4.36 (m, 1H), 3.98 (m, 1H), 2.08 (m, 4H), 2.05 (s, 3H), 1.81–1.52 (m, 12H). MS m/z 443 (M+1).

EXAMPLE 23

N-Cyclopentyl-3-[2-(cyclopropylamino)-4-pyrimidinyl]-2-(3-methyl-2-furyl)pyrazolo[1,5-a]pyridin-7-amine

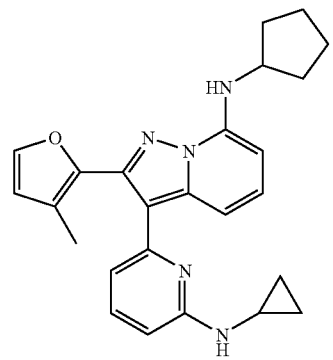

a) 4-[7-Chloro-2-(3-methyl-2-furyl)pyrazolo[1,5-a]pyridin-3-yl]-N-cyclopropyl-2-pyrimidinamine. In a similar manner described in Example 22 from 1-[7-chloro-2-(3-methyl-2-furyl)pyrazolo[1,5-a]pyridin-3-yl]-2-propyn-1-one (500 mg, 1.76 mmol) was obtained 4-[7-chloro-2-(3-methyl-2-furyl)pyrazolo[1,5-a]pyridin-3-yl]-N-cyclopropyl-2-pyrimidinamine (182 mg, 28%) as a pale yellow solid. $^1$H-NMR (CDCl$_3$): δ 8.66 (broad d, 1H), 8.18 (d, 1H), 7.48 (d, 1H), 7.22 (t, 1H), 7.03 (d, 1H), 6.41 (m, 2H), 5.75 (s, 1H), 2.81 (m, 1H), 2.12 (s, 3H), 0.80 (m, 2H), 0.59 (m, 2H). MS m/z 366 (M+1).

b) N-Cyclopentyl-3-[2-(cyclopropylamino)-4-pyrimidinyl]-2-(3-methyl-2-furyl)pyrazolo[1,5-a]pyridin-7-amine In the similar manner as described in Example 22 from 4-[7-chloro-2-(3-methyl-2-furyl)pyrazolo[1,5-a]pyridin-3-yl]-N-cyclopropyl-2-pyrimidinamine (80 mg, 0.22 mmol) was obtained N-cyclopentyl-3-[2-(cyclopropylamino)-4-pyrimidinyl]-2-(3-methyl-2-furyl)pyrazolo[1,5-a]pyridin-7-amine (20 mg, 21%) as a yellow foam. $^1$H-NMR (CDCl$_3$): δ 8.12 (d, 1H), 8.01 (d, 1H), 7.51 (d, 1H), 7.31 (t, 1H), 6.43 (d, 1H), 6.32 (d, 1H), 6.05 (d, 1H), 6.00 (d, 1H), 5.35 (s, 1H), 4.00 (m, 1H), 2.87 (m, 1H), 2.13 (m, 2H), 2.06 (s, 3H), 1.81–1.66 (m, 6H), 0.86 (m, 2H), 0.62 (m, 2H). MS m/z 415 (M+1).

EXAMPLE 24

N-Cyclopropyl-3-[2-(cyclopropylamino)-4-pyrimidinyl]-2-(3-methyl-2-furyl)pyrazolo[1,5-a]pyridin-7-amine

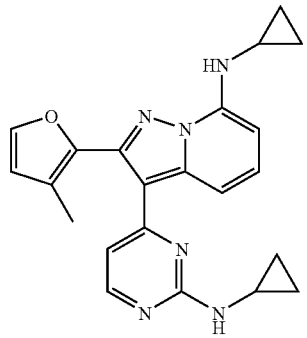

In a similar manner as described in Example 22 from 4-[7-chloro-2-(3-methyl-2-furyl)pyrazolo[1,5-a]pyridin-3-yl]-N-cyclopropyl-2-pyrimidinamine (92 mg, 0.25 mmol) was obtained N-cyclopropyl-3-[2-(cyclopropylamino)-4-pyrimidinyl]-2-(3-methyl-2-furyl)pyrazolo[1,5-a]pyridin-7-amine (75 mg, 77%) as a yellow solid. $^1$H-NMR (CDCl$_3$): δ 8.17 (d, 1H), 8.12 (d, 1H), 7.54 (d, 1H), 7.38 (t, 1H), 6.46–6.36 (m, 4H), 5.44 (s, 1H), 2.89 (m, 1H), 2.70 (m, 1H), 2.09 (s, 3H), 0.91 (m, 4H), 0.77 (m, 2H), 0.66 (m, 2H). MS m/z 387 (M+1).

EXAMPLE 25

N-Cyclopentyl-3-[2-(cyclopentylamino)-4-pyrimidinyl]-2-(2-furyl)pyrazolo[1,5-a]pyridin-7-amine

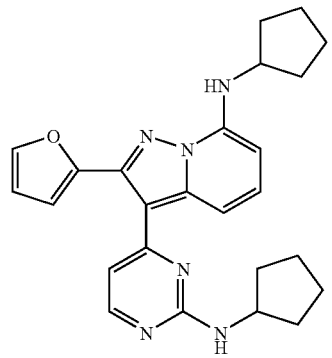

a) 7-Chloro-2-(2-furyl)pyrazolo[1,5-a]pyridine-3-carbaldehyde

A dry flask charged with dry N,N-dimethylformamide (100 mL) was treated with phosphorous oxychloride (6.0 mL 64.5 mmol). The resultant solution was stirred at room temperature for 1 hour. 7-Chloro-2-(2-furyl)pyrazolo[1,5-a]pyridine (9.4 g, 43 mmol, example 21) was added to the previous solution and stirred for 2.5 hours. Water and dichloromethane were added to quench the reaction. The aqueous phase and organic phase were separated. The aqueous phase was extracted with dichloromethane. The organics were combined and washed with water, dried over magnesium sulfate, filtered and concentrated. Crystallization from a small amount of methanol gave 7-chloro-2-(2-furyl)pyrazolo[1,5-a]pyridine-3-carbaldehyde (8.4 g, 79%) as pale yellow crystalline compound. $^1$H NMR (CDCl$_3$): δ 10.57 (s, 1H), 8.41 (d, 1H), 7.71 (d, 1H), 7.51 (t, 1H), 7.27 (d, 1H), 7.22 (d, 1H), 6.66 (m, 1H). MS m/247 (M+1).

b) 1-[7-Chloro-2-(2-furyl)pyrazolo[1,5-a]pyridin-3-yl]-2-propyn-1-ol

To a solution of 7-chloro-2-(2-furyl)pyrazolo[1,5-a]pyridine-3-carbaldehyde (3.36 g, 13.6 mmol) in tetrahydrofuran (100 mL) at −78° C. was added ethynylmagnesium bromide (32.7 mL, 0.5 M in tetrahydrofuran, 16.3 mmol). The mixture was allowed to warm to room temperature and stirred for 1 hour. Water was added to the reaction and the resulting mixture was extracted with ethyl acetate. The ethyl acetate phase was dried over magnesium sulfate, filtered and concentrated to a solid residue, 1-[(7-chloro-2-(2-furyl)pyrazolo[1,5-a]pyridin-3-yl]-2-propyn-1-ol (3.63 g, 98%). $^1$H NMR (CDCl$_3$): δ 7.98 (d, 1H), 7.59 (d, 1H), 7.16 (t, 1H), 7.03 (d, 1H), 6.95 (d, 1H), 6.55 (m, 1H), 6.16 (m, 1H), 2.76 (m, 1H), 2.63 (s, 1H). MS m/z 273 (M+1).

c) 1-[7-Chloro-2-(2-furyl)pyrazolo[1,5-a]pyridin-3-yl]-2-propyn-1-one

1-[7-Chloro-2-(2-furyl)pyrazolo[1,5-a]pyridin-3-yl]-2-propyn-1-ol (3.63 g, 13.3 mmol) was dissolved in dichloromethane (200 mL) and manganese dioxide (34.7 g, 399 mmol) was added. This slurry was stirred at room temperature for 2 hours. The manganese dioxide was removed by filtration and the filtrate was concentrated to a solid, 1-[7-chloro-2-(3-methyl-2-furyl)pyrazolo[1,5-a]pyridin-3-yl]-2-propyn-1-one (1.99 g, 55%). $^1$H NMR (CDCl$_3$): δ 8.54 (d, 1H), 7.65 (d, 1H), 7.62 (d, 1H), 7.49 (t, 1H), 7.21 (d, 1H), 6.58 (m, 1H), 3.35 (s, 1H). MS m/z 271 (M+1).

d) 4-[7-Chloro-2-(2-furyl) pyrazolo[1,5-a]pyridin-3-yl]-N-cyclopentyl-2-pyrimidinamine Cyclopentylguanidine hydrochloride (1.53 g, 9.38 mmol) and potassium carbonate (0.78 g. 5.63 mmol) were added to 80 mL of ethanol. The suspension was stirred at room temperature for 1 hour. 1-[7-Chloro-2-(2-furyl)pyrazolo[1,5-a]pyridin-3-yl]-2-propyn-1-one (1.27 g, 4.69 mmol) was added to the resultant solution and stirred at room temperature for 24 hours. The reaction mixture was concentrated and ethyl acetate and water were added. The phases were separated, the organic phase was dried over magnesium sulfate, filtered and concentrated. Purification by flash chromatography (3:7 ethyl acetatehexanes). gave 4-[7-Chloro-2-(2-furyl)pyrazolo[1,5-a]pyridin-3-yl]-N-cyclopentyl-2-pyrimidinamine (520 mg, 30%) as a yellow solid. $^1$H NMR (CDCl$_3$): δ 8.28 (d, 1H), 8.22 (d, 1H), 7.58 (d, 1H), 7.23 (m, 1H), 7.04 (d, 1H), 6.92 (d, 1H), 6.62 (d, 1H), 6.53 (m, 1H), 5.16 (d, 1H), 4.35 (m, 1H), 2.07 (m, 2H), 1.77–1.52 (m, 6H). MS m/z 380 (M+1).

e) N-Cyclopentyl-3-[2-(cyclopentylamino)-4-pyrimidinyl]-2-(2-furyl) pyrazolo[1,5-a]pyridin-7-amine 4-[7-Chloro-2-(2-furyl)pyrazolo[1,5-a]pyridin-3-yl]-N-cyclopentyl-2-pyrimidinamine (200 mg, 0.53 mmol) was dissolved in 5 mL of cyclopentylamine. The solution was heated at 100° C. overnight, then cooled to room temperature. Ethyl acetate was added to dilute the reaction mixture, the organic phase was washed with water and brine and dried over magnesium sulfate. Filtration and concentration followed by purification with flash chromatography (1:4 ethyl acetate:hexanes) gave N-cyclopentyl-3-[2-(cyclopentylamino)-4-pyrimidinyl]-2-(2-furyl)pyrazolo[1,5-a]pyridin-7-amine (206 mg, 91%) as a yellow solid. $^1$H NMR (CDCl$_3$): δ 8.20 (d, 1H), 7.68 (d, 1H), 7.62 (d, 1H), 7.32 (t, 1H), 6.92 (d, 1H), 6.59 (m, 2H), 6.05 (m, 2H), 5.11 (d, 1H), 4.43 (m, 1H), 4.04 (m, 1H), 2.14 (m, 4H), 1.87–1.56 (m, 12H). MS m/z 429 (M+1).

EXAMPLE 26

3-[2-(Cyclopentylamino)-4-pyrimidinyl]-N-cyclopropyl-2-(2-furyl)pyrazolo[1,5-a]pyridin-7-amine

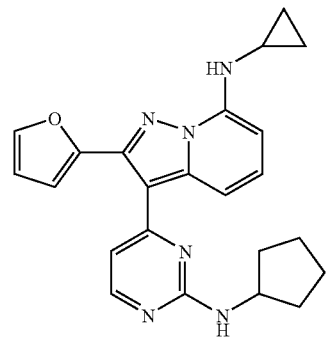

4-[7-Chloro-2-(2-furyl)pyrazolo[1,5-a]pyridin-3-yl]-N-cyclopentyl-2-pyrimidinamine (100 mg, 0.26 mmol) and cyclopropylamine (5 mL) were put in a steel bomb. After heating at 100° C. for 3 days, the reaction was allowed to cool to room temperature. The reaction mixture was diluted with ethyl acetate, washed with water and brine, then dried over magnesium sulfate. Filtration and concentration followed by purification with flash chromatography (3:7 ethyl acetate:hexanes) gave 3-[2-(cyclopentylamino)-4-pyrimidinyl]-N-cyclopropyl-2-(2-furyl)pyrazolo[1,5-a]pyridin-7-amine (34 mg, 32%) as a yellow foam. $^1$H NMR (CDCl$_3$): δ 8.15 (d, 1H), 7.67 (d, 1H), 7.56 (d, 1H), 7.30 (t, 1H), 6.86 (d, 1H), 6.57 (d, 1H), 6.52 (m, 1H), 6.36 (d, 1H), 6.32 (s, 1H), 5.14 (d, 1H), 4.36 (m, 1H), 2.63 (m, 1H), 2.08 (m, 2H), 1.76–1.52 (m, 6H), 0.86 (m, 2H), 0.75 (m, 2H). MS m/401 (M+1).

EXAMPLE 27

2-(5-Bromo-2-furyl)-N-cyclopentyl-3-[2-(cyclopentylamino)-4-pyrimidinyl]pyrazolo[1,5-a]pyridin-7-amine

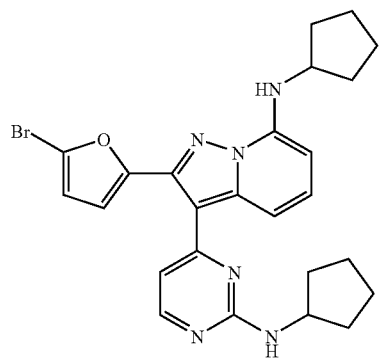

a) 2-(5-Bromo-2-furyl)-7-chloropyrazolo[1,5-a]pyridine-3-carbaldehyde

To a solution of 7-chloro-2-(2-furyl)pyrazolo[1,5-a]pyridine-3-carbaldehyde (2.0 g, 8.06 mmol) in dichloromethane was added N-bromosuccinimide (2.01 g, 11.28 mmol). After stirring at room temperature for 2 hours, the reaction mixture was diluted with dichloromethane, washed with water and brine and dried over magnesium sulfate. Filtration and concentration followed by recrystallization with ethyl acetate gave 2-(5-bromo-2-furyl)-7-chloropyrazolo[1,5-a]pyridine-3-carbaldehyde (2.1 g, 80%) as a white solid. $^1$H NMR (CDCl$_3$): δ 10.50 (s, 1H), 8.37 (dd, 1H), 7.47 (t, 1H), 7.20–7.18 (m, 2H), 6.54 (d, 1H). MS m/z 325 (M+1).

b) 1-[2-(5-Bromo-2-furyl)-7-chloropyrazolo[1,5-a]pyridin-3-yl]-2-propyn-1-one In a similar manner as described in Example 25 from 2-(5-bromo-2-furyl)-7-chloropyrazolo[1,5-a]pyridine-3-carbaldehyde (2.54 g, 7.8 mmol) was obtained 1-[2-(5-bromo-2-furyl)-7-chloropyrazolo[1,5-a]pyridin-3-yl]-2-propyn-1-ol. To the solution of 1-[2-(5-bromo-2-furyl)-7-chloropyrazolo[1,5-a]pyridin-3-yl]-2-propyn-1-ol in dichloromethane was added manganese dioxide as described in example 25. 1-[2-(5-Bromo-2-furyl)-7-chloropyrazolo[1,5-a]pyridin-3-yl]-2-propyn-1-one (0.86 g, two steps 32%) was obtained as a yellow solid. $^1$H NMR (CDCl$_3$): δ 8.53 (d, 1H), 7.52–7.48 (m, 2H), 7.22 (d, 1H), 6.51 (d, 1H), 3.36 (s, 1H). MS m/z 349 (M+1).

c) 4-[2-(5-Bromo-2-furyl)-7-chloropyrazolo[1,5-a]pyridin-3-yl]-N-cyclopentyl-2-pyrimidinamine.

In a similar manner as described in example 25 from 1-[2-(5-bromo-2-furyl)-7-chloropyrazolo[1,5-a]pyridin-3-yl]-2-propyn-1-one (0.85 g, 2.43 mmol) was obtained 4-[2-(5-bromo-2-furyl)-7-chloropyrazolo[1,5-a]pyridin-3-yl]-N-cyclopentyl-2-pyrimidinamine (0.81 g, 73%) as a pale yellow solid. $^1$H NMR (CDCl$_3$): δ 8.24 (m, 2H), 7.25 (t, 1H), 7.05 (dd, 1H), 6.88 (d, 1H), 6.66 (d, 1H), 6.46 (d, 1H), 5.15 (d, 1H), 4.35 (m, 1H), 2.07 (m, 2H), 1.77–1.52 (m, 6H). MS m/z 458 (M+1).

d) 2-(5-Bromo-2-furyl)-N-cyclopentyl-3-[2-(cyclopentylamino)-4-pyrimidinyl]pyrazolo[1,5-a]pyridin-7-amine.

In a similar manner as described in example 25 from 4-[2-(5-bromo-2-furyl)-7-chloropyrazolo[1,5-a]pyridin-3-yl]-N-cyclopentyl-2-pyrimidinamine (200 mg, 0.56 mmol) was obtained 2-(5-bromo-2-furyl)-N-cyclopentyl-3-[2-(cyclopentylamino)-4-pyrimidinyl]pyrazolo[1,5-a]pyridin-7-amine (190 mg, 86%) as a yellow foam. $^1$H NMR (CDCl$_3$): δ 8.16 (d, 1H), 7.56 (d, 1H), 7.28 (t, 1H), 6.83 (d, 1H), 6.62 (d, 1H), 6.45 (d, 1H), 6.04 (d, 1H), 6.01 (d, 1H), 5.20 (b, 1H), 4.37 (m, 1H), 4.00 (m, 1H), 2.18–2.04 (m, 4H), 1.84–1.55 (m, 12H). MS m/z 507 (M+1).

EXAMPLE 28

N-Cyclopentyl-3-[2-(cyclopentylamino)-4-pyridinyl]-2-(2-methyl-1,3-thiazol-4-yl)pyrazolo[1,5-a]pyridin-7-amine

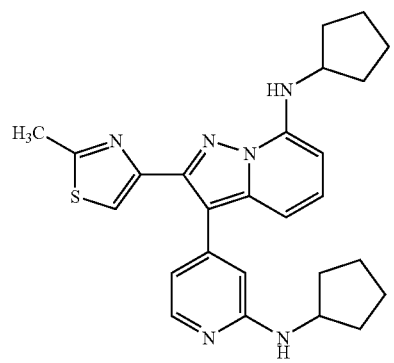

a) 4-(2-Fluoro-4-pyridinyl)-3-butyn-2-ol

A solution of 2-fluoro-4-iodopyridine (3.0 g, 13 mmol), 3-butyn-2-ol (2.1 mL, 26 mmol), dichlorobis(triphenylphosphine) palladium (II) (0.9 g, 1.3 mmol), copper (I) iodide (0.5 g, 2.6 mmol), triethylamine (5.4 mL 39 mmol), and anhydrous N,N-dimethylformamide (20 mL) were heated to 75° C. for 4 hours. When judged to be complete, the mixture was partitioned between ethyl acetate and water, the organics were washed with brine, dried over magnesium sulfate, filtered and concentrated. The crude mixture was purified using flash chromatography (4:1 hexanes:ethyl acetate) to provide 4-(2-fluoro-4-pyridinyl)-3-butyn-2-ol (1.4 g, 66%) as an orange oil. $^1$H NMR (DMSO-d$_6$): δ 8.21 (d, 1H), 7.32 (d, 1H), 7.20 (s, 1H), 5.62 (d, 1H), 4.61 (m, 1H), 1.36 (d, 3H).

b) 1-[3-(2-Fluoro-4-pyridinyl)pyrazolo[1,5-a]pyridin-2-yl]ethanol

A solution of 4-(2-fluoro-4-pyridinyl)-3-butyn-2-ol (1.4 g, 8.5 mmol), aminopyridinium iodide (2.2 g, 9.8 mmol), 1,8-diazobicyclo[5.4.0]undec-7-ene (1.9 mL, 12.7 mmol), and acetonitrile (20 mL) were allowed to stir for 12–16 hours at room temperature. When judged to be complete, the mixture was partitioned between ethyl acetate and water, the organics were washed with brine, dried over magnesium sulfate, filtered and suspended onto silica gel. The crude material was purified by flash chromatography (1:1 hexanes:ethyl acetate) to provide 1-[3-(2-fluoro-4-pyridinyl)pyrazolo[1,5-a]pyridin-2-yl]ethanol (1.0 g, 460%) as a beige solid. $^1$H NMR (DMSO-d$_6$): δ 8.79 (d, 1H), 8.30 (d, 1H), 7.87 (d, 1H), 7.67 (d, 1H), 7.50 (s, 1H), 7.41 (m, 1H), 7.04 (m, 1H), 5.57 (m, 1H), 5.03 (m, 1H), 1.56 (d, 3H).

c) 1-[3-(2-Fluoro-4-pyridinyl)pyrazolo[1,5-a]pyridin-2-yl]ethanone

A solution of 1-[3-(2-fluoro-4-pyridinyl)pyrazolo[1,5-a]pyridin-2-yl]ethanol (0.1 g, 0.4 mmol), manganese(IV)oxide (0.17 g. 1.95 mmol), and methylene chloride (10 mL) were allowed to stir at room temperature for 72 hours. When judged to be complete, the mixture was filtered through a plug of Celite, and the filtrate was concentrated to provide 1-[3-(2-fluoro-4-pyridinyl)pyrazolo[1,5-a]pyridin-2-yl]ethanone (97 mg, 98%) as a pale yellow solid. $^1$H NMR (DMSO-$d_6$): δ 8.92 (d. 1H), 8.30 (d, 1H), 7.82 (d, 1H), 7.46 (m, 2H), 7.34 (s, 1H), 7.23 (m, 1H), 2.71 (s, 3H).

d) 2-Bromo-1-[3-(2-fluoro-4-pyridinyl)pyrazolo[1,5-a]pyridin-2-yl]ethanone

To a solution of 1-[3-(2-fluoro-4-pyridinyl)pyrazolo[1,5-a]pyridin-2-yl]ethanone (580 mg, 2.27 mmol) in acetic acid (20 mL) was added bromine (0.12 mL, 2.27 mmol). After heating at 80° C. for 30 minutes, the solution was cooled to room temperature. Ethyl acetate was added to dilute the reaction mixture. The mixture was washed with water (×3), brine and dried over magnesium sulfate. Filtration and concentration, followed by recrystallization from ethyl acetate gave 2-bromo-1-[3-(2-fluoro-4-pyridinyl)pyrazolo[1,5-a]pyridin-2-yl]ethanone (478 mg, 64%) as a yellow solid. $^1$H NMR (CDCl$_3$): δ 8.51 (d, 1H), 8.27 (d, 1H), 7.65 (d, 1H), 7.33 (m, 2H), 7.10 (s, 1H), 7.06 (t, 1H), 4.76 (s, 2H). MS m/334 (M+1).

e) 3-(2-Fluoro-4-pyridinyl)-2-(2-methyl-1,3-thiazol-4-yl)pyrazolo[1,5-a]pyridine To a solution of 2-bromo-1-[3-(2-fluoro-4-pyridinyl)pyrazolo[1,5-a]pyridin-2-yl]ethanone (250 mg, 0.75 mmol) in N,N-dimethylformamide (15 mL) was added thioacetamide (67 mg, 0.90 mmol). After heating at 60° C. for 3 hours, the reaction was cooled to room temperature. An ammonium hydroxide solution was used to adjust the pH to 9. The resultant solution was extracted with ethyl acetate. The organics were combined and washed with water, brine and dried over magnesium sulfate. Filtration and concentration gave 3-(2-fluoro-4-pyridinyl)-2-(2-methyl-1,3-thiazol-4-yl)pyrazolo[1,5-a]pyridine (220 mg, 95%) as a pale yellow solid. $^1$H NMR (CDCl$_3$): δ 8.56 (d, 1H), 8.23 (d, 1H), 7.61 (d, 1H), 7.30 (s, 1H), 7.27 (m, 2H), 7.05 (s, 1H), 6.89 (m, 1H), 2.76 (s, 3H). MS m/z 311 (M+1).

f) N-Cyclopentyl-4-[2-(2-methyl-1,3-thiazol-4-yl)pyrazolo[1,5-a]pyridin-3-yl]-2-pyridinamine A solution of 3-(2-fluoro-4-pyridinyl)-2-(2-methyl-1,3-thiazol-4-yl)pyrazolo[1,5-a]pyridine (220 mg, 0.71 mmol) and potassium carbonate (98 mg, 0.71 mmol) in cyclopentylamine (5 mL) was heated at 100° C. for 12 days. After cooling to room temperature, the solution was diluted with ethyl acetate and the organic phase was washed with water and brine, then dried over magnesium sulfate. Filtration and concentration, followed by flash chromatography (1:9 methanol/chloroform) gave N-cyclopentyl-4-[2-(2-methyl-1,3-thiazol-4-yl)pyrazolo[1,5-a]pyridin-3-yl]-2-pyridinamine (265 mg, 100%) as an oil. $^1$H NMR (CDCl$_3$): δ 8.49 (d, 1H), 8.04 (d, 1H), 7.49 (d, 1H), 7.08 (d, 1H), 6.74 (t, 1H), 6.59 (d, 1H), 6.43 (s, 1H), 5.44 (d, 1H), 3.79 (m, 1H), 2.73 (s, 3H), 1.92–1.42 (m, 8H). MS m/z 376 (M+1).

g) 4-[7-Chloro-2-(2-methyl-1,3-thiazol-4-yl)pyrazolo[1,5-a]pyridin-3-yl]-N-cyclopentyl-2-pyridinamine A solution of N-cyclopentyl-4-[2-(2-methyl-1,3-thiazol-4-yl)pyrazolo[1,5-a]pyridin-3-yl]-2-pyridinamine (138 mg, 0.37 mmol) in tetrahydrofuran (10 mL) was cooled to −78° C. n-Butyl lithium (1.6M in hexanes, 0.75 mL, 1.22 mmol) was added dropwise. After stirring at −78° C. for 20 minutes, carbon tetrachloride (1 mL) was added to the solution. The reaction was stirred for another 20 minutes at −78° C. and subsequently quenched with water. The reaction mixture was warmed to room temperature and extracted with ethyl acetate. The organics were combined and washed with water, brine and dried over magnesium sulfate. Filtration and concentration, followed by flash chromatography (1:19 methanol/dichloromethane) gave 4-[7-chloro-2-(2-methyl-1,3-thiazol-4-yl)pyrazolo[1,5-a]pyridin-3-yl]-N-cyclopentyl-2-pyridinamine as a brown oil.

h) N-Cyclopentyl-3-[2-(cyclopentylamino)-4-pyridinyl]-2-(2-methyl-1,3-thiazol-4-yl)pyrazolo[1,5-a]pyridin-7-amine To 4-[7-chloro-2-(2-methyl-1,3-thiazol-4-yl)pyrazolo[1,5-a]pyridin-3-yl]-N-cyclopentyl-2-pyridinamine from previous reaction was added cyclopentylamine and the resulting mixture heated to 80° C. for 3 days. The resultant solution was cooled to room temperature, diluted with ethyl acetate and washed with water, brine and dried over magnesium sulfate. Filtration and concentration followed by flash chromatography (1:19 methanol/dichloromethane) gave N-cyclopentyl-3-[2-(cyclopentylamino)-4-pyridinyl]-2-(2-methyl-1,3-thiazol-4-yl)pyrazolo[1,5-a]pyridin-7-amine (20 mg, 120% for two steps) as a brown foam. $^1$H NMR (CDCl$_3$): δ 8.09 (d, 1H), 7.56 (d, 1H), 7.34 (s, 1H), 7.15 (t, 1H), 6.98 (d, 1H), 6.64 (d, 1H), 6.45 (s, 1H), 5.60 (d, 1H), 4.80 (b, 1H), 3.94 (m, 1H), 3.87 (m, 1H), 2.76 (s, 3H), 1.98–1.45 (m, 16H). MS m/z 459 (M+1).

EXAMPLE 29

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; UdATP means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; SCC means sodium chloride/sodium citrate; "APE" means a solution of ammonia acetate, ammonia phosphate, EDTA; "PBSU" means phosphate buffered saline; and "HRP" means horseradish peroxidase.

a) Tissue Culture and HSV infection.

Vero 76 cells were maintained in MEM with Earle's salts, L-glutamine, 8% FBS (Hyclone, A-1111-L) and 100 units/mL Penicillin-100 µg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180 μM dTTP, 20 μM dUTP-digoxigenin (Boehringer Mannheim 1558706), 200 μM each of dATP, dCTP, and dGTP, 1×PCR Buffer II (Perkin Elmer), 2.5 mM $MgCl_2$, 0.025 units/μL of AmpliTaq Gold polymerase (Perkin Elmer), and 5 ng of gel-purified HSV DNA per 100 μL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5× Denhardt's solution, 0.25×APE, and 5 ng of the digoxigenin-labeled detection probe). APE is 1.5 M $NH_4$-acetate, 0.15 M ammonium phosphate monobasic, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μl/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 mL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | $IC_{50}$ (μM) |
|---|---|
| 1 | 1.5 |
| 3 | 0.6 |

-continued

| Example No. | $IC_{50}$ (μM) |
|---|---|
| 4 | 3.1 |
| 6 | 0.4 |
| 8 | 0.8 |
| 9 | 23 |
| 10 | 33 |
| 11 | 1.6 |
| 12 | 36 |

| Example No. | $IC_{50}$ (μM) |
|---|---|
| 13 | 3.3 |
| 17 | 2.9 |
| 18 | 1 |
| 19 | 0.7 |
| 20 | 0.5 |
| 21 | 0.5 |
| 22 | 0.2 |
| 23 | 0.8 |
| 24 | 5 |
| 25 | 0.5 |
| 26 | 1.4 |
| 27 | 0.5 |
| 28 | 1.7 |

The results demonstrate that the compounds of the present invention are useful for the treatment and prophylaxis of herpes viral infections.

The invention claimed is:

1. A compound of formula (I):

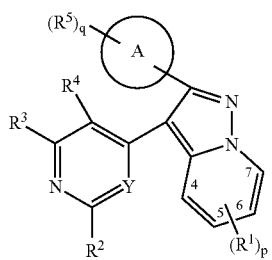

wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)NR$^7$R$^8$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$—S(O)$_n$Ay, —S(O)$_n$Het, —S(O)$_2$NR$^7$R$^8$, S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$O—C(O)R$^9$, —R$^{10}$O—C(O)Ay, —R$^{10}$O—C(O)Het, —R$^{10}$O—S(O)$_n$R$^9$, —R$^{10}$OR$^9$, —R$^{10}$C(O)R$^9$, —R$^{10}$CO$_2$R$^9$, —R$^{10}$C(O)NR$^7$Ay, —R$^{10}$C(O)NR$^9$R$^{11}$, —ROC(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido;

or two adjacent R¹ groups together with the carbon atoms to which they are bonded form a cycloalkyl or a 5- or 6-membered heterocyclic group containing 1 or 2 heteroatoms;

each $R^7$ and $R^8$ are the same or different and are independently selected from the group consisting of H, alkyl, alkenyl, cycloalkyl, cycloalkenyl, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹;

each $R^9$ and $R^{11}$ are the same or different and are independently selected from the group consisting of H, alkyl, cycloalkyl —R¹⁰cycloalkyl, —R¹⁰OH, —R¹⁰(OR¹⁰)_w wherein w is 1–10, and —R¹⁰NR¹⁰R¹⁰;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

Y is N;

R² is selected from the group consisting of halo, alkyl, alkenyl, cycloalkyl, cycloalkenyl, Ay, Het, —OR⁷, —OAy, —OHet, —OR¹⁰Het, —S(O)_nR⁹, —S(O)_nAy, —S(O)_nHet, —S(O)_nNR⁷R⁸—NR⁷R⁸, —NHHet, —NHR¹⁰Ay, —NHR¹⁰Het, —R¹⁰NR⁷R⁸ and —R¹⁰NR⁷Ay;

n is 0, 1 or 2;

R³ and R⁴ are the same or different and are each independently selected from the group consisting of H, halo, alkyl, alkenyl, cycloalkyl, Ay, Het, —OR⁷, —OAy, —(O)R⁷, C(O)Ay, —CO₂R⁷, —CO₂Ay, —SO₂NHR⁹, —NR⁷R⁸, —NR⁷Ay, —NHet, —NHR¹⁰Het,—R¹⁰cycloalkyl,—R¹⁰OR⁷,—R¹⁰OAy, —R¹⁰NR⁷R⁸ and —R¹⁰NR⁷Ay;

Ring A is a 5–10 membered heterocyclic or heteroaryl group;

q is 0, 12, 3, 4 or 5; and each $R^5$ is the same or different and is independently selected from the group consisting of halo, alkyl, alkenyl, alkynyl, cycloalkyl, cycloalkenyl, Ay, Het, —OR⁷, —OAy, —OR¹⁰Ay, —OHet, —OR¹⁰Het, , —C(O)R¹¹, —C(O)Ay, —C(O)Het, —CO₂R⁹, —C(O)NR⁷R⁸, —C(O)NR⁷Ay, —C(O)NHR¹⁰Het, —C(S)NR⁹R¹¹—C(NH)NR⁷R⁸,—C(NH)NR⁷Ay,—S(O)_nR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl,—R¹⁰Het,—R¹⁰OR⁹,—R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido;

or a pharmaceutically acceptable salt thereof.

2. The compound according to claim 1 wherein p is 0, 1 or 2.

3. The compound according to claim 1 wherein p is 1.

4. The compound according to claim 1 wherein each $R^1$ is the same or different and is independently selected from the group consisting of halo, alkyl, Ay, Het, —OR⁷, —OAy, —C(O)Het, —CO₂R⁹, —C(O)NR⁷R⁸, —C(O)NR⁷Ay, —C(O)NHR¹⁰Het, —S(O)_nR⁹, —NR⁷R⁸, —NR⁷Ay, —NHHet, —NHR¹⁰Ay, —NHR¹⁰Het, —R¹⁰OR⁹, cyano, nitro and azido.

5. The compound according to claim 1 wherein each $R^1$ is the same or different and is independently selected from the group consisting of halo, alkyl, Het, —OR⁷, —C(O)NR⁷R⁸, —S(O)_nR⁹, —NR⁷R⁸, —NR⁷Ay and —NHHet.

6. The compound according to claim 1 wherein $R^2$ is selected from the group consisting of Ay, Het, —OR⁷, —OHet, —OR¹⁰Het, —S(O)_nR⁹, —NR⁷R⁸, —NHHet, —NHR¹⁰Het and —R¹⁰NR⁷R⁸.

7. The compound according to claim 1 wherein $R^2$ is selected from the group consisting of —NR⁷R⁸ and Het.

8. The compound according to claim 1 wherein $R^3$ and $R^4$ are the same or different and are each independently selected from the group consisting of H, halo, alkyl, Ay, —OR⁷, —CO₂R⁷, —NR⁷R⁸, —R¹⁰OR⁷ and —R¹⁰NR⁷R⁸.

9. The compound according to claim 1 wherein $R^3$ and $R^4$ are each H.

10. The compound according to claim 1 wherein Ring A is selected from the group consisting of furan, pyridine, pyrimidine, thiazol, pyrazine, pyrrole, imidazole, oxazole, benzimidazole, quinoline, isoquinoline and quinoxoline.

11. The compound according to claim 1 wherein Ring A is selected from the group consisting of furan, thiazole, pyridine and pyrimidine.

12. The compound according to claim 1 wherein q is selected from the group consisting of 0, 1 and 2.

13. The compound according to claim 1 wherein q is 1.

14. The compound according to claim 1 wherein each $R^5$ is the same or different and is independently selected from the group consisting of halo, alkyl, alkenyl, Ay, Het, —OR⁷, —OAy, —CO₂R⁹, —C(O)NR⁷R⁸, —C(O)NR⁷Ay, —S(O)₂NR⁷R⁸, —NR⁷R⁸, —NR⁷Ay, —NHR¹⁰Ay, cyano, nitro and azido.

15. The compound according to claim 1, wherein each $R^5$ is the same or different and is independently selected from the group consisting of halo, alkyl, —OR⁷, —NR⁷R⁸, cyano, nitro and azido.

16. A compound selected from the group consisting of:
N-Cyclopentyl-3-[2-(cyclopentylamino)-4-pyrimidinyl]-2-(4-pyridinyl)pyrazolo[1,5-a]pyridin-7-amine;
N-Cyclopentyl-3-[2-(methylamino)-4-pyrimidinyl]-2-(4-pyridinyl)pyrazolo[1,5-a]pyridin-7-amine;
N-cyclopentyl-3-[2-(cyclopentylamino)-4-pyrimidinyl]-2-(3-pyridinyl)pyrazolo[1,5-a]pyridin-7-amine;
N-Cyclopentyl-N-(4-{2-[2-(cyclopentylamino)-4-pyrimidinyl]pyrazolo[1,5-a]pyridin-3-yl}-2-pyrimidinyl) amine;
N-(4-{7-Chloro-2-[2-(cyclopentylamino)-4-pyrimidinyl]pyrazolo[1,5-a]pyridin-3-yl}-2-pyrimidinyl)-N-cyclopentylamine;
N-Cyclopentyl-2,3-bis[2-(cyclopentylamino)-4-pyrimidinyl]pyrazolo[1,5-a]pyridin-7-amine;
N-(2-Methoxyethyl)-2,3-bis{2-[(2-methoxyethyl)amino]pyrimidin-4-yl}pyrazolo[1,5-a]pyridin-7-amine;
N-Butyl-2,3-bis[2-(butylamino)pyrimidin-4-yl-]pyrazolo[1,5-a]pyridin-7-amine;
N-Cyclopropyl-2,3-bis[2-(cyclopropylamino)pyrimidin-4-yl]pyrazolo[1,5-a]pyridin-7-amine;
7-Morpholin-4-yl-2,3-bis(2-morpholin-4-yl-pyrimidin-4-yl)pyrazolo[1,5-a]pyridine;
N-Isobutyl-2,3-bis[2-(isobutylamino)pyrimidin-4-yl] pyrazolo[1,5-a]pyridin-7-amine;
N-Benzyl-2,3-bis[2-(benzylamino)pyrimidin-4-yl]pyrazolo[1,5-a]pyridin-7-amine;

N-Isopropyl-2,3-bis[2-(isopropylamino)pyrimidin-4-yl]
    pyrazolo[1,5-a]pyridin-7-amine;
2-(2-Fluoro-4-pyridinyl)-3-[2-(methylsulfanyl)-4-pyrimidinyl]pyrazolo[1,5-a]pyridine;
4-[2-(2-Fluoro-4-pyridinyl)pyrazolo[1,5-a]pyridin-3-yl]-
    N-isopropyl-2-pyrimidinamine;
N-Isopropyl-4-{2-[2-(isopropylamino)-4-pyridinyl]pyrazolo[1,5-a]pyridin-3-yl}-2-pyrimidinamine;
3-[2(Cyclopropylamino)-4-pyrimidinyl]-N-isopropyl-2-
    [2-(isopropylamino)-4-pyridinyl]pyrazolo[1,5-a]pyridin-7-amine;
N-Cyclopentyl-2-[2-(cyclopentylamino)-4-pyridinyl]-3-
    [2-(isopropylamino)-4-pyridinyl]pyrazolo[1,5-a]pyridin-7-amine;
3-[2-(Cyclopentylamino)-4-pyrimidinyl]-N-isopropyl-2-
    [2-(isopropylamino) pyridinyl]pyrazolo[1,5-a]pyridin-
    7-amine;
N-Cyclopentyl-3-[2-(cyclopentylamino)-4-pyrimidinyl]-
    2-[2-(isopropylamino)-4-pyridinyl]pyrazolo[1,5-a]pyridin-7-amine;
N-Cyclopentyl-3-[2-(cyclopentylamino)-4-pyrimidinyl]-
    2-(3-methyl-2-furyl)pyrazolo[1,5-a]pyridin-7-amine;
N-Cyclopentyl-3-[2-(cyclopropylamino)-4-pyrimidinyl]-
    2-(3-methyl-2-furyl)pyrazolo[1,5-a]pyridin-7-amine;
N-Cyclopropyl-3-[2-(cyclopropylamino)-4-pyrimidinyl]-
    2-(3-methyl-2-furyl)pyrazolo[1,5-a]pyridin-7-amine;
N-Cyclopentyl-3-[2-(cyclopentylamino)-4-pyrimidinyl]-
    2-(2-furyl)pyrazolo[1,5-a]pyridin-7-amine;
3-[2-(Cyclopentylamino)-4-pyrimidinyl]-N-cyclopropyl-
    2-(2-furyl)pyrazolo[1,5-a]pyridin-7-amine;
2-(5-Bromo-2-furyl)-N-cyclopentyl-3-[2-(cyclopentylamino)-4-pyrimidinyl]pyrazolo[1,5-a]pyridin-7-
    amine; and
or a pharmaceutically acceptable salt thereof.

17. A process for preparing the compound according to claim 1 wherein $R^3$ and $R^4$ are H; said process comprising reacting a compound of formula (IX);

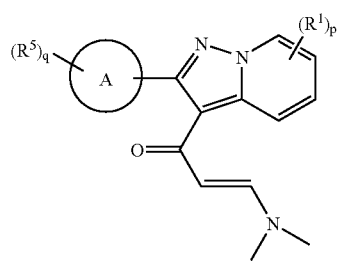

IX with a compound of formula (X);

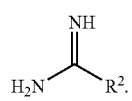

X

18. A process for preparing the compound according to claim 1, wherein $R^3$ is selected from the group consisting of of H, alkyl, cycloalkyl, alkenyl, Ay, Het, —$OR^7$, —OAy, —$C(O)R^7$, $C(O)$Ay, —$CO_2R^7$, —$CO_2$Ay, —$SO_2NHR^9$, —$NR^7R^8$ (where $R^7$ and $R^8$ are not H), —$NR^7$Ay (where $R^7$ is not H), —$R^{10}$cycloalkyl, —$R^{10}OR^7$, —$R^{10}$OAy, —$R^{10}NR^7R^8$ and —$R^{10}NR^7$Ay, and $R^4$ is H, said process comprising reacting a compound of formula (XVI):

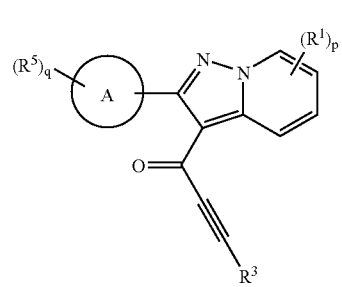

XVI with a compound of formula (X):

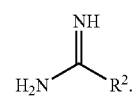

X

19. A process for preparing the compound according to claim 1, said process comprising reacting a compound of formula (XX):

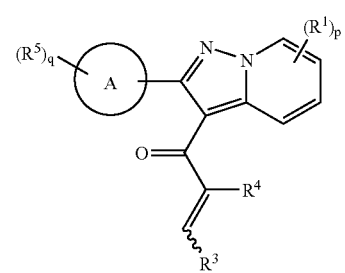

XX with a compound of formula (X):

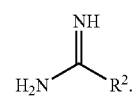

X followed by oxidative aromatization.

20. A process for preparing the compound according to claim 1, said process comprising reacting a compound of formula (XXII):

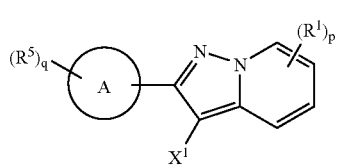

XXII wherein $X^1$ is chloro, bromo or iodo;

with a compound of formula (XXIV):

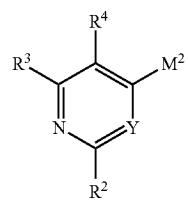

XXIV wherein M² is selected from the group consisting of —B(OH)₂, —B(ORa)₂, —B(Ra)₂, —Sn(Ra)₃, Zn-halide, ZnRa, and Mg-halide, where Ra is alkyl or cycloalkyl and halide is halo.

21. A process for preparing the compound according to claim 1, said process comprising reacting a compound of formula (XXIX):

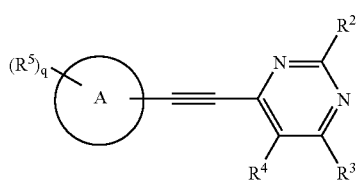

XXIX with a 1-aminopyridinium salt of formula (XXX):

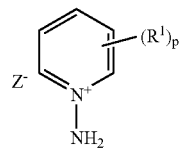

XXX wherein Z- is a counter ion.

22. A process for preparing the compound according to claim 1, said process comprising reacting a compound of formula (XXXVI):

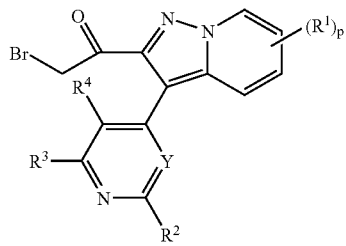

XXXVI with a suitable ring forming reagent.

23. A pharmaceutical composition comprising a compound according to claim 1.

24. A pharmaceutical composition according to claim 23 further comprising a pharmaceutically acceptable carrier or diluent.

25. A pharmaceutical composition according to claim 23 further comprising an antiviral agent selected from the group consisting of aciclovir and valaciclovir.

26. A method for the treatment of a herpes viral infection selected from herpes simplex virus 1 and herpes simplex virus 2 in an animal, said method comprising administering to the animal a therapeutically effective amount of a compound according to claim 1.

27. A method for the treatment of a condition or disease associated with a herpes viral infection selected from herpes simplex virus 1 and herpes simplex virus 2 in an animal, comprising administering to the animal a therapeutically effective amount of a compound according to claim 1.

* * * * *

UNITED STATES PATENT AND TRADEMARK OFFICE
CERTIFICATE OF CORRECTION

| | | |
|---|---|---|
| PATENT NO. | : 7,199,120 B2 | Page 1 of 2 |
| APPLICATION NO. | : 10/496358 | |
| DATED | : April 3, 2007 | |
| INVENTOR(S) | : Gudmundsson et al. | |

It is certified that error appears in the above-identified patent and that said Letters Patent is hereby corrected as shown below:

Title Page – item 56 Foreign Documents reads: WO EP 0 364 204 A1
Should read:
-- EP 0364 204 A1 --

Title Page – item 56 Foreign Documents reads: WO 02 18382 3/2000
Should read:
-- WO 02 18382 3/2002 --

Column 96, Claim 1, line 63 should read:
-- -$R^{10}C(O)NR^9R^{11}$, -$R^{10}C(O)NR^7Ay$, -$R^{10}C(O)$ --

Column 97, Claim 1, line 38 should read:
-- -OAy, -$C(O)R^7$, C(O)Ay, -$CO_2R^7$, -$CO_2Ay$, --

Column 97, Claim 1, line 39 should read:
-- $SO_2NHR^9$, -$NR^7R^8$, -$NR^7Ay$, -NHHet, --

Column 97, Claim 1, line 44 should read:
-- q is 0, 1, 2, 3, 4 or 5; and --

Column 97, Claim 1, line 49 should read:
-- -$C(O)R^9$, -C(O)Ay, -C(O)Het, -$CO_2R^9$, -C(O) --

Column 98, Claim 16, line 58 should read:
-- N-Butyl-2,3-bis[2-butylamino)pyrimidin-4-yl]pyrazolo --

Column 99, Claim 16, line 9 should read:
-- 3-[2-Cyclopropylamino)-4-pyrimidinyl]-N-isopropyl-2- --

Column 99, Claim 16, line 13 should read:
-- [2-(isopropylamino)-4-pyrimidinyl)pyrazolo[1,5-a]pyri- --

Column 99, Claim 16, line 16 should read:
-- [2-isopropylamino)-4-pyridinyl]pyrazolo[1,5-a]pyridin- --

UNITED STATES PATENT AND TRADEMARK OFFICE
CERTIFICATE OF CORRECTION

PATENT NO. : 7,199,120 B2
APPLICATION NO. : 10/496358
DATED : April 3, 2007
INVENTOR(S) : Gudmundsson et al.

It is certified that error appears in the above-identified patent and that said Letters Patent is hereby corrected as shown below:

Column 99, Claim 18, line 64 should read:
-- H, alkyl, cycloalkyl, alkenyl, Ay, Het, $-OR^7$, -OAy, --

Signed and Sealed this

Twenty-ninth Day of April, 2008

JON W. DUDAS
*Director of the United States Patent and Trademark Office*